United States Patent
You et al.

(10) Patent No.: US 11,725,058 B2
(45) Date of Patent: Aug. 15, 2023

(54) CD137 ANTIBODIES FOR T-CELL ACTIVATION

(71) Applicant: AP Biosciences, Inc., Taipei (TW)

(72) Inventors: Jhong-Jhe You, Taipei (TW);
Ching-Hsuan Hsu, Taoyaun (TW);
Po-Lin Huang, Taipei (TW);
Jeng-Horng Her, San Jose, CA (US)

(73) Assignee: AP Biosciences, Inc., Taipei (TW)

( * ) Notice: Subject to any disclaimer, the term of this patent is extended or adjusted under 35 U.S.C. 154(b) by 221 days.

(21) Appl. No.: 16/911,052

(22) Filed: Jun. 24, 2020

(65) Prior Publication Data

US 2020/0407456 A1 Dec. 31, 2020

Related U.S. Application Data

(60) Provisional application No. 62/953,302, filed on Dec. 24, 2019, provisional application No. 62/866,699, filed on Jun. 26, 2019.

(51) Int. Cl.
*C07K 16/28* (2006.01)
*A61K 39/00* (2006.01)

(52) U.S. Cl.
CPC ...... *C07K 16/2878* (2013.01); *C07K 16/2827* (2013.01); *A61K 2039/505* (2013.01); *C07K 2317/31* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/622* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| 8,629,250 B2* | 1/2014 | Sasu ............... A61K 38/1816 424/130.1 |
|---|---|---|
| 10,131,704 B2* | 11/2018 | Marasco ......... G01N 33/56983 |
| 10,906,983 B2* | 2/2021 | Frye ..................... A61P 35/00 |
| 2006/0246071 A1 | 11/2006 | Green et al. |
| 2014/0065166 A1 | 3/2014 | Broder et al. |

(Continued)

FOREIGN PATENT DOCUMENTS

| WO | WO 2017/220988 | 12/2017 |
|---|---|---|
| WO | WO 2019/027754 | 2/2019 |

OTHER PUBLICATIONS

Kranz et al., Restricted reassociation of heavy and light chains from hapten-specific monoclonal antibodies, Proc. Natl. Acad. Sci. USA, 78(9):5807-5811, Sep. 1981.*

(Continued)

*Primary Examiner* — Claire Kaufman
(74) *Attorney, Agent, or Firm* — DLA Piper LLP (US)

(57) ABSTRACT

Antibodies that include an antigen binding region that binds to CD137 are provided herein. Also provided herein are bispecific antibodies that include a first antigen binding region that binds to CD137 and a second antigen binding region that binds to an immune checkpoint molecule, an immune stimulatory molecule, or a tumor antigen. Pharmaceutical compositions that include the antibodies and methods of treating cancer are provided.

12 Claims, 35 Drawing Sheets

Specification includes a Sequence Listing.

(56) References Cited

U.S. PATENT DOCUMENTS

| | | | |
|---|---|---|---|
| 2014/0113831 A1 | 4/2014 | Chen et al. | |
| 2016/0244528 A1* | 8/2016 | Gray | A61P 37/04 |
| 2019/0161554 A1 | 5/2019 | Gray et al. | |
| 2020/0017595 A1* | 1/2020 | Geuijen | C07K 16/2875 |

OTHER PUBLICATIONS

Nezlin, RS, Biochemistry of Antibodies, Plenum Press:New York, p. 160, 1970.*
MacCallum et al.,Antibody-antigen interactions: contact analysis and binding site topography, J. Mol. Biol. 262:732-745, 1996.*
Lamminmaki et al., Chrystal structure of a recombinant anti-estradiol Fab fragment in complex with the 17beta-estradiol, J. Biol. Chem. 276:36687-94, 2001.*
Chen et al., Enhancement and destruction of antibody function by somatic mutation: unequal occurrence is controlled by V gene combinatorial associations, EMBO J. 14(12):2784-2794, 1995.*
Herold et al., Determinants of the assembly and function of antibody variable domains, Sci. Rep. 7:12276, DOI:10.1038/s41598-017-12519-9, Sep. 2017.*
PCT International Search Report and Written Opinion in International Application No. PCT/US2020/039218, dated Nov. 24, 2020, 19 pages.
Su et al., "immunoglobulin lambda variable region, partial [*Homo sapiens*]" GenBank: CAP74504.1, Jul. 26, 2016, 1 page.
Titani et al., "The Amino Acid Sequence of a λ Type Bence-Jones Protein", the Journal of Biological Chemistry, Apr. 1970, 245(8):2171-2176.

* cited by examiner

| PARAMETER | UNIT | VALUE | |
|---|---|---|---|
| | | #31 | #54 |
| $C_{MAX}$ | µg/ml | 142.5 | 129.2 |
| $T_{MAX}$ | H | 0.5 | 0.5 |
| $T_{1/2}$ | H | 396.7 | 335.5 |
| AUC 0-T | µg/ml*h | 17294.3 | 19934.9 |
| AUC 0-INF_OBS | µg/ml*h | 36734.3 | 39964.2 |

| | UNIT | 25 mg/kg FEMALE | 25 mg/kg MALE | 5 mg/kg FEMALE | 5 mg/kg MALE |
|---|---|---|---|---|---|
| CMAX | µg/ml | 507.88 | 403.85 | 96.24 | 95.78 |
| T1/2 | h | 91.03 | 82.43 | 45.31 | 51.83 |
| AUC 0-T | µG/ML*H | 35414.62 | 32919.44 | 4837.25 | 4647.08 |
| Cl_OBS | (mg/kg)/(µg/ml)h | 0.0004748 | 0.0005284 | 0.0046397 | 0.0046334 |
| VSS_OBS | (mg/kg)/(µg/ml) | 0.0607443 | 0.0631104 | 0.2785128 | 0.3257398 |

SEQUENCE LISTING

```
<160> NUMBER OF SEQ ID NOS: 46

<210> SEQ ID NO 1
<211> LENGTH: 124
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-CD137 clone 15 heavy chain

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Leu Tyr Gln Leu Leu Phe Pro Tyr Tyr Gly Met Asp
            100                 105                 110

Val Trp Gly Gln Gly Thr Thr Val Thr Val Ser Ser
        115                 120

<210> SEQ ID NO 2
<211> LENGTH: 222
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-CD137 clone 15 light chain

<400> SEQUENCE: 2

Gln Leu Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80
```

```
Lys Asn Ile Gln Glu Glu Asp Glu Ser Asp Tyr His Cys Gly Ala Asp
                85                  90                  95

His Gly Ser Gly Ser Asn Leu Phe Trp Val Phe Gly Gly Gly Thr Lys
            100                 105                 110

Leu Thr Val Leu Gly Gln Pro Lys Ala Ala Pro Ser Val Thr Leu Phe
        115                 120                 125

Pro Pro Ser Ser Glu Glu Leu Gln Ala Asn Lys Ala Thr Leu Val Cys
    130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Cys Ser
    210                 215                 220

<210> SEQ ID NO 3
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H1 of anti-CD137 clone 15

<400> SEQUENCE: 3

Gly Gly Thr Phe Ser Ser Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H2 of anti-CD137 clone 15

<400> SEQUENCE: 4

Ile Pro Ile Leu Gly Ile
1               5

<210> SEQ ID NO 5
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H3 of anti-CD137 clone 15

<400> SEQUENCE: 5

Asp Leu Tyr Gln Leu Leu Phe Pro Tyr Tyr Tyr Gly Met Asp Val
1               5                   10                  15

<210> SEQ ID NO 6
<211> LENGTH: 12
<212> TYPE: PRT
```

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L1 of anti-CD137 clone 15

<400> SEQUENCE: 6

Thr Leu Ser Ser Gly Tyr Ser Asn Tyr Lys Val Asp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L2 of anti-CD137 clone 15

<400> SEQUENCE: 7

Val Gly Thr Gly Gly Ile Val Gly Ser Lys Gly Asp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L3 of anti-CD137 clone 15

<400> SEQUENCE: 8

Gly Ala Asp His Gly Ser Gly Ser Asn Leu Phe Trp Val
1               5                   10

<210> SEQ ID NO 9
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-CD137 clone 31 heavy chain

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Arg Gly Ala Phe Asp Pro Trp Gly Gln Gly Thr Thr
            100                 105                 110

Val Thr Val Ser Ser

-continued

115

<210> SEQ ID NO 10
<211> LENGTH: 217
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-CD137 clone 31 light chain

<400> SEQUENCE: 10

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Phe Val Ser Trp Tyr Gln Gln Arg Pro Gly Lys Ala Pro Glu Leu
        35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Ser
                85                  90                  95

Ile Thr Arg Tyr Val Phe Gly Thr Gly Thr Lys Val Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 11
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H1 of anti-CD137 clone 31

<400> SEQUENCE: 11

```
Gly Tyr Thr Phe Thr Gly Tyr
1               5
```

<210> SEQ ID NO 12
<211> LENGTH: 6
<212> TYPE: PRT
<213> ORGANISM: Artificial Sequence
<220> FEATURE:

```
<223> OTHER INFORMATION: Synthetic
<220> FEATURE:
<221> NAME/KEY: misc_feature
<223> OTHER INFORMATION: CDR-H2 of anti-CD137 clone 31

<400> SEQUENCE: 12

Asn Pro Asn Ser Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H3 of anti-CD137 clone 31

<400> SEQUENCE: 13

Asp Leu Arg Gly Ala Phe Asp Pro
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L1 of anti-CD137 clone 31

<400> SEQUENCE: 14

Thr Gly Thr Ser Ser Asp Val Gly Ala Tyr Asn Phe Val Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L2 of anti-CD137 clone 31

<400> SEQUENCE: 15

Asp Val Ser Asp Arg Pro Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L3 of anti-CD137 clone 31

<400> SEQUENCE: 16

Ser Ser Tyr Thr Ser Ser Ile Thr Arg Tyr Val
1               5                   10

<210> SEQ ID NO 17
<211> LENGTH: 126
<212> TYPE: PRT
<213> ORGANISM: Artificial Sequence
```

```
<220> FEATURE:
<223> OTHER INFORMATION: Synthetic
<220> FEATURE:
<221> NAME/KEY: misc_feature
<223> OTHER INFORMATION: Anti-CD137 clone 54 heavy chain

<400> SEQUENCE: 17

Gln Val Gln Leu Val Gln Ser Gly Ala Glu Val Lys Lys Pro Gly Ser
1               5                   10                  15

Thr Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Pro Tyr Tyr Asp Ser Ser Gly Tyr Tyr Pro Leu Gly Ala
            100                 105                 110

Phe Asp Ile Trp Gly Gln Gly Thr Met Val Thr Val Ser Ser
        115                 120                 125

<210> SEQ ID NO 18
<211> LENGTH: 213
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-CD137 clone 54 light chain

<400> SEQUENCE: 18

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Glu Lys Tyr Ala
            20                  25                  30

Ser Trp Tyr Gln Gln Lys Ala Gly Gln Ser Pro Ile Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Leu Gln Ala Gly
65                  70                  75                  80

Asp Glu Ala Asp Tyr Tyr Cys Gln Ala Trp Asp Gly Ser Ser Thr Tyr
                85                  90                  95

Val Phe Gly Thr Gly Thr Lys Val Thr Val Phe Gly Gln Pro Lys Ala
            100                 105                 110

Asn Pro Thr Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
    130                 135                 140

Val Thr Val Ala Trp Lys Ala Asp Gly Ser Pro Val Lys Ala Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
```

Ser Cys Gln Val Thr His Glu Gly Ser Thr Val Glu Lys Thr Val Ala
            195                 200                 205

Pro Thr Glu Cys Ser
    210

<210> SEQ ID NO 19
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H1 of anti-CD137 clone 54

<400> SEQUENCE: 19

Gly Gly Thr Phe Ser Ser Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H2 of anti-CD137 clone 54

<400> SEQUENCE: 20

Ile Pro Ile Leu Gly Ile
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H3 of anti-CD137 clone 54

<400> SEQUENCE: 21

Pro Pro Tyr Tyr Asp Ser Ser Gly Tyr Tyr Pro Leu Gly Ala Phe Asp
1               5                   10                  15

Ile

<210> SEQ ID NO 22
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L1 of anti-CD137 clone 54

<400> SEQUENCE: 22

Ser Gly Asp Lys Leu Gly Glu Lys Tyr Ala Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L2 of anti-CD137 clone 54

<400> SEQUENCE: 23

Gln Asp Ser Lys Arg Pro Ser
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L3 of anti-CD137 clone 54

<400> SEQUENCE: 24

Gln Ala Trp Asp Gly Ser Ser Thr Tyr Val
1               5                   10

<210> SEQ ID NO 25
<211> LENGTH: 327
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: constant domain in heavy chain (IgG4)

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 26
<211> LENGTH: 329
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: constant domain in heavy chain (engineered
      IgG1)

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 27
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SP1

<400> SEQUENCE: 27

Met Glu Thr Asp Thr Leu Leu Leu Trp Val Leu Leu Leu Trp Val Pro
1               5                   10                  15

Gly Ser Thr Gly
            20

<210> SEQ ID NO 28
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: GS linker

<400> SEQUENCE: 28

Gly Gly Gly Gly Ser
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: (G4S)2 linker

<400> SEQUENCE: 29

Gly Gly Gly Gly Ser Gly Gly Gly Gly Ser
1               5                   10

<210> SEQ ID NO 30
<211> LENGTH: 217
<212> TYPE: PRT
<213> ORGANISM: Artificial Sequence
<220> FEATURE:
```

<223> OTHER INFORMATION: Synthetic
<220> FEATURE:
<221> NAME/KEY: misc_feature
<223> OTHER INFORMATION: Anti-PD-L1#6 Light Chain

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Leu Ser Leu
                85                  90                  95

Asn Ala Trp Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 31
<211> LENGTH: 700
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-PD-L1 #6-CD137 #31 bsAb Heavy Chain

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

```
Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
            435                 440                 445

Gly Gly Gly Ser Gly Gly Gly Gly Gln Ser Ala Leu Thr Gln Pro Ala
        450                 455                 460

Ser Val Ser Gly Ser Pro Gly Gln Ser Ile Thr Ile Ser Cys Thr Gly
465                 470                 475                 480

Thr Ser Ser Asp Val Gly Ala Tyr Asn Phe Val Ser Trp Tyr Gln Gln
                485                 490                 495

Arg Pro Gly Lys Ala Pro Glu Leu Met Ile Tyr Asp Val Ser Asp Arg
            500                 505                 510
```

Pro Ser Gly Val Ser Asn Arg Phe Ser Gly Ser Lys Gly Asn Thr
            515                 520                 525

Ala Ser Leu Thr Ile Ser Gly Leu Gln Thr Glu Asp Glu Ala Asp Tyr
530                 535                 540

Tyr Cys Ser Ser Tyr Thr Ser Ser Ile Thr Arg Tyr Val Phe Gly Thr
545                 550                 555                 560

Gly Thr Lys Val Thr Val Leu Gly Gly Gly Ser Gly Gly Gly
            565                 570                 575

Ser Gly Gly Gly Ser Gln Val Gln Leu Val Gln Ser Gly Ala Glu
            580                 585                 590

Val Lys Lys Pro Gly Ala Ser Val Lys Val Ser Cys Lys Ala Ser Gly
            595                 600                 605

Tyr Thr Phe Thr Gly Tyr Tyr Met His Trp Val Arg Gln Ala Pro Gly
610                 615                 620

Gln Gly Leu Glu Trp Met Gly Trp Ile Asn Pro Asn Ser Gly Gly Thr
625                 630                 635                 640

Asn Tyr Ala Gln Lys Phe Gln Gly Arg Val Thr Met Thr Arg Asp Thr
            645                 650                 655

Ser Ile Ser Thr Ala Tyr Met Glu Leu Ser Arg Leu Arg Ser Asp Asp
            660                 665                 670

Thr Ala Val Tyr Tyr Cys Ala Arg Asp Leu Arg Gly Ala Phe Asp Pro
            675                 680                 685

Trp Gly Gln Gly Thr Thr Val Thr Val Ser Ser Ala
            690                 695                 700

<210> SEQ ID NO 32
<211> LENGTH: 712
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-PD-L1#6-CD137 #54 bsAb Heavy Chain

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Arg Tyr
            20                  25                  30

Ser Ile Ser Trp Val Arg Gln Ala Pro Gly Gln Gly Leu Glu Trp Met
        35                  40                  45

Gly Gly Ile Ile Pro Val Phe Gly Ala Ala Lys Tyr Ala Gln Lys Phe
    50                  55                  60

Gln Gly Arg Val Thr Ile Thr Ala Asp Glu Phe Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Leu Ser Gly Asp Ser Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

-continued

```
Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
            245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Ala Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Ala Val Ser Asn Lys Ala Leu Pro Ala Pro Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Gly
            435                 440                 445
Gly Gly Gly Ser Gly Gly Gly Gly Ser Gln Val Gln Leu Val Gln Ser
            450                 455                 460
Gly Ala Glu Val Lys Lys Pro Gly Ser Thr Val Lys Val Ser Cys Lys
465                 470                 475                 480
Ala Ser Gly Gly Thr Phe Ser Ser Tyr Ala Ile Ser Trp Val Arg Gln
            485                 490                 495
Ala Pro Gly Gln Gly Leu Glu Trp Met Gly Arg Ile Ile Pro Ile Leu
            500                 505                 510
Gly Ile Ala Asn Tyr Ala Gln Lys Phe Gln Gly Arg Val Thr Ile Thr
            515                 520                 525
Ala Asp Lys Ser Thr Ser Thr Ala Tyr Met Glu Leu Ser Ser Leu Arg
            530                 535                 540
Ser Glu Asp Thr Ala Val Tyr Tyr Cys Ala Ser Pro Pro Tyr Tyr Asp
545                 550                 555                 560
Ser Ser Gly Tyr Tyr Pro Leu Gly Ala Phe Asp Ile Trp Gly Gln Gly
            565                 570                 575
Thr Met Val Thr Val Ser Ser Ala Gly Gly Gly Gly Ser Gly Gly Gly
```

```
                    580                 585                 590
Gly Ser Gly Gly Gly Ser Gly Gly Gly Ser Ser Tyr Glu Leu
            595                 600                 605

Thr Gln Pro Pro Ser Val Ser Val Ser Pro Gly Gln Thr Ala Ser Ile
        610                 615                 620

Thr Cys Ser Gly Asp Lys Leu Gly Glu Lys Tyr Ala Ser Trp Tyr Gln
625                 630                 635                 640

Gln Lys Ala Gly Gln Ser Pro Ile Leu Val Ile Tyr Gln Asp Ser Lys
                645                 650                 655

Arg Pro Ser Gly Ile Pro Glu Arg Phe Ser Gly Ser Asn Ser Gly Asn
            660                 665                 670

Thr Ala Thr Leu Thr Ile Ser Gly Leu Gln Ala Gly Asp Glu Ala Asp
        675                 680                 685

Tyr Tyr Cys Gln Ala Trp Asp Gly Ser Ser Thr Tyr Val Phe Gly Thr
690                 695                 700

Gly Thr Lys Val Thr Val Leu Gly
705                 710

<210> SEQ ID NO 33
<211> LENGTH: 244
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CD137#31-scFv

<400> SEQUENCE: 33

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Phe Val Ser Trp Tyr Gln Gln Arg Pro Gly Lys Ala Pro Glu Leu
        35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Thr Glu Asp Glu Ala Asp Tyr Tyr Cys Ser Ser Tyr Thr Ser Ser
                85                  90                  95

Ile Thr Arg Tyr Val Phe Gly Thr Gly Thr Lys Val Thr Val Leu Gly
            100                 105                 110

Gly Gly Gly Ser Gly Gly Gly Gly Ser Gly Gly Gly Gly Ser Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Gly Tyr Tyr Met
145                 150                 155                 160

His Trp Val Arg Gln Ala Pro Gly Gln Gly Leu Glu Trp Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Val Tyr Tyr Cys Ala Arg
```

Asp Leu Arg Gly Ala Phe Asp Pro Trp Gly Gln Gly Thr Thr Val Thr
225                 230                 235                 240

Val Ser Ser Ala

<210> SEQ ID NO 34
<211> LENGTH: 255
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CD137#54-scFv

<400> SEQUENCE: 34

Gln Val Gln Leu Val Gln Ser Gly Ala Glu Val Lys Lys Pro Gly Ser
1               5                   10                  15

Thr Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Pro Tyr Tyr Asp Ser Ser Gly Tyr Tyr Pro Leu Gly Ala
            100                 105                 110

Phe Asp Ile Trp Gly Gln Gly Thr Met Val Thr Val Ser Ser Ala Gly
        115                 120                 125

Gly Gly Gly Ser Gly Gly Gly Gly Ser Gly Gly Gly Gly Ser Gly Gly
    130                 135                 140

Gly Gly Ser Ser Tyr Glu Leu Thr Gln Pro Pro Ser Val Ser Val Ser
145                 150                 155                 160

Pro Gly Gln Thr Ala Ser Ile Thr Cys Ser Gly Asp Lys Leu Gly Glu
                165                 170                 175

Lys Tyr Ala Ser Trp Tyr Gln Gln Lys Ala Gly Gln Ser Pro Ile Leu
            180                 185                 190

Val Ile Tyr Gln Asp Ser Lys Arg Pro Ser Gly Ile Pro Glu Arg Phe
        195                 200                 205

Ser Gly Ser Asn Ser Gly Asn Thr Ala Thr Leu Thr Ile Ser Gly Leu
    210                 215                 220

Gln Ala Gly Asp Glu Ala Asp Tyr Tyr Cys Gln Ala Trp Asp Gly Ser
225                 230                 235                 240

Ser Thr Tyr Val Phe Gly Thr Gly Thr Lys Val Thr Val Leu Gly
                245                 250                 255

<210> SEQ ID NO 35
<211> LENGTH: 214
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Trastuzumab Light Chain

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 714
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Trastuzumab-CD137 #54 bsAb Heavy Chain

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val

```
            115                 120                 125
Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Gly Gly Gly Ser Gly Gly Gly Ser Gln Val Gln Leu Val
                450                 455                 460

Gln Ser Gly Ala Glu Val Lys Lys Pro Gly Ser Thr Val Lys Val Ser
465                 470                 475                 480

Cys Lys Ala Ser Gly Gly Thr Phe Ser Ser Tyr Ala Ile Ser Trp Val
                485                 490                 495

Arg Gln Ala Pro Gly Gln Gly Leu Glu Trp Met Gly Arg Ile Ile Pro
                500                 505                 510

Ile Leu Gly Ile Ala Asn Tyr Ala Gln Lys Phe Gln Gly Arg Val Thr
                515                 520                 525

Ile Thr Ala Asp Lys Ser Thr Ser Thr Ala Tyr Met Glu Leu Ser Ser
                530                 535                 540
```

```
Leu Arg Ser Glu Asp Thr Ala Val Tyr Tyr Cys Ala Ser Pro Pro Tyr
545                 550                 555                 560

Tyr Asp Ser Ser Gly Tyr Tyr Pro Leu Gly Ala Phe Asp Ile Trp Gly
                565                 570                 575

Gln Gly Thr Met Val Thr Val Ser Ser Ala Gly Gly Gly Gly Ser Gly
            580                 585                 590

Gly Gly Gly Ser Gly Gly Gly Ser Gly Gly Gly Ser Ser Tyr
        595                 600                 605

Glu Leu Thr Gln Pro Pro Ser Val Ser Val Ser Pro Gly Gln Thr Ala
        610                 615                 620

Ser Ile Thr Cys Ser Gly Asp Lys Leu Gly Glu Lys Tyr Ala Ser Trp
625                 630                 635                 640

Tyr Gln Gln Lys Ala Gly Gln Ser Pro Ile Leu Val Ile Tyr Gln Asp
                645                 650                 655

Ser Lys Arg Pro Ser Gly Ile Pro Glu Arg Phe Ser Gly Ser Asn Ser
            660                 665                 670

Gly Asn Thr Ala Thr Leu Thr Ile Ser Gly Leu Gln Ala Gly Asp Glu
        675                 680                 685

Ala Asp Tyr Tyr Cys Gln Ala Trp Asp Gly Ser Ser Thr Tyr Val Phe
690                 695                 700

Gly Thr Gly Thr Lys Val Thr Val Leu Gly
705                 710
```

<210> SEQ ID NO 37
<211> LENGTH: 216
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-Her2 #3-7 Light Chain

<400> SEQUENCE: 37

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 38
<211> LENGTH: 717
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-Her2 #3-7-CD137 #54 bsAb Heavy Chain

<400> SEQUENCE: 38

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Asp Asn Trp Asn His Gly Pro Tyr Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300
```

-continued

Thr Tyr Arg Val Val Ser Val Leu Thr Val Leu His Gln Asp Trp Leu
305                 310                 315                 320

Asn Gly Lys Glu Tyr Lys Cys Ala Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Gly Gly Gly Ser Gly Gly Gly Gly Ser Gln Val
450                 455                 460

Gln Leu Val Gln Ser Gly Ala Glu Val Lys Lys Pro Gly Ser Thr Val
465                 470                 475                 480

Lys Val Ser Cys Lys Ala Ser Gly Gly Thr Phe Ser Ser Tyr Ala Ile
            485                 490                 495

Ser Trp Val Arg Gln Ala Pro Gly Gln Gly Leu Glu Trp Met Gly Arg
            500                 505                 510

Ile Ile Pro Ile Leu Gly Ile Ala Asn Tyr Ala Gln Lys Phe Gln Gly
            515                 520                 525

Arg Val Thr Ile Thr Ala Asp Lys Ser Thr Ser Thr Ala Tyr Met Glu
            530                 535                 540

Leu Ser Ser Leu Arg Ser Glu Asp Thr Ala Val Tyr Tyr Cys Ala Ser
545                 550                 555                 560

Pro Pro Tyr Tyr Asp Ser Ser Gly Tyr Tyr Pro Leu Gly Ala Phe Asp
            565                 570                 575

Ile Trp Gly Gln Gly Thr Met Val Thr Val Ser Ser Ala Gly Gly Gly
            580                 585                 590

Gly Ser Gly Gly Gly Gly Ser Gly Gly Gly Gly Ser Gly Gly Gly Gly
            595                 600                 605

Ser Ser Tyr Glu Leu Thr Gln Pro Pro Ser Val Ser Val Ser Pro Gly
            610                 615                 620

Gln Thr Ala Ser Ile Thr Cys Ser Gly Asp Lys Leu Gly Glu Lys Tyr
625                 630                 635                 640

Ala Ser Trp Tyr Gln Gln Lys Ala Gly Gln Ser Pro Ile Leu Val Ile
            645                 650                 655

Tyr Gln Asp Ser Lys Arg Pro Ser Gly Ile Pro Glu Arg Phe Ser Gly
            660                 665                 670

Ser Asn Ser Gly Asn Thr Ala Thr Leu Thr Ile Ser Gly Leu Gln Ala
            675                 680                 685

Gly Asp Glu Ala Asp Tyr Tyr Cys Gln Ala Trp Asp Gly Ser Ser Thr
            690                 695                 700

Tyr Val Phe Gly Thr Gly Thr Lys Val Thr Val Leu Gly
705                 710                 715

<210> SEQ ID NO 39
<211> LENGTH: 213
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-Glycan Light Chain

<400> SEQUENCE: 39

```
Glu Ile Val Leu Thr Gln Ser Pro Ser Thr Leu Ser Leu Ser Pro Gly
1               5                   10                  15

Glu Arg Ala Thr Leu Ser Cys Gln Ala Ser Glu Asp Val Ser Tyr Met
            20                  25                  30

His Trp Tyr Gln Gln Lys Pro Gly Gln Ala Pro Gln Pro Trp Ile Tyr
        35                  40                  45

Gly Thr Ser Asn Lys Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Gln Trp Ser Arg Arg Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 40
<211> LENGTH: 717
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Anti-Glycan-CD137 #54 bsAb Heavy Chain

<400> SEQUENCE: 40

```
Gln Ile Thr Leu Gln Glu Ser Gly Pro Thr Leu Val Lys Pro Thr Gln
1               5                   10                  15

Thr Leu Thr Leu Thr Cys Thr Phe Ser Gly Phe Ser Leu Tyr Arg Phe
            20                  25                  30

Asp Met Gly Val Gly Trp Ile Arg Gln Pro Pro Gly Gln Gly Leu Glu
        35                  40                  45

Trp Leu Ala His Ile Trp Trp Asp Asp Asp Lys Tyr Tyr Asn Pro Ala
    50                  55                  60
```

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Val Arg Gly Leu His Asp Tyr Tyr Tyr Phe Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Ala Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Ala Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Gly Gly Gly Ser Gly Gly Gly Ser Gln Val
            450                 455                 460

Gln Leu Val Gln Ser Gly Ala Glu Val Lys Lys Pro Gly Ser Thr Val
465                 470                 475                 480
```

```
Lys Val Ser Cys Lys Ala Ser Gly Gly Thr Phe Ser Ser Tyr Ala Ile
                485                 490                 495

Ser Trp Val Arg Gln Ala Pro Gly Gln Gly Leu Glu Trp Met Gly Arg
            500                 505                 510

Ile Ile Pro Ile Leu Gly Ile Ala Asn Tyr Ala Gln Lys Phe Gln Gly
        515                 520                 525

Arg Val Thr Ile Thr Ala Asp Lys Ser Thr Ser Thr Ala Tyr Met Glu
    530                 535                 540

Leu Ser Ser Leu Arg Ser Glu Asp Thr Ala Val Tyr Tyr Cys Ala Ser
545                 550                 555                 560

Pro Pro Tyr Tyr Asp Ser Ser Gly Tyr Tyr Pro Leu Gly Ala Phe Asp
                565                 570                 575

Ile Trp Gly Gln Gly Thr Met Val Thr Val Ser Ser Ala Gly Gly Gly
            580                 585                 590

Gly Ser Gly Gly Gly Gly Ser Gly Gly Gly Gly Ser Gly Gly Gly Gly
        595                 600                 605

Ser Ser Tyr Glu Leu Thr Gln Pro Pro Ser Val Ser Val Ser Pro Gly
    610                 615                 620

Gln Thr Ala Ser Ile Thr Cys Ser Gly Asp Lys Leu Gly Glu Lys Tyr
625                 630                 635                 640

Ala Ser Trp Tyr Gln Gln Lys Ala Gly Gln Ser Pro Ile Leu Val Ile
                645                 650                 655

Tyr Gln Asp Ser Lys Arg Pro Ser Gly Ile Pro Glu Arg Phe Ser Gly
            660                 665                 670

Ser Asn Ser Gly Asn Thr Ala Thr Leu Thr Ile Ser Gly Leu Gln Ala
        675                 680                 685

Gly Asp Glu Ala Asp Tyr Tyr Cys Gln Ala Trp Asp Gly Ser Ser Thr
    690                 695                 700

Tyr Val Phe Gly Thr Gly Thr Lys Val Thr Val Leu Gly
705                 710                 715

<210> SEQ ID NO 41
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H1 of anti-Her2#3-7

<400> SEQUENCE: 41

Gly Tyr Ser Phe Thr Ser Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H2 of anti-Her2#3-7

<400> SEQUENCE: 42

Tyr Pro Gly Asp Ser Asp
1               5

<210> SEQ ID NO 43
```

```
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-H3 of anti-Her2#3-7

<400> SEQUENCE: 43

Gln Asp Asn Trp Asn His Gly Pro Tyr Asp Ala Phe Asp Ile
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L1 of anti-Her2#3-7

<400> SEQUENCE: 44

Gly Leu Ser Ser Gly Ser Val Ser Thr Ser Tyr Tyr Pro Ser
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L2 of anti-Her2#3-7

<400> SEQUENCE: 45

Ser Thr Asn Thr Arg Ser Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: CDR-L3 of anti-Her2#3-7

<400> SEQUENCE: 46

Val Leu Tyr Met Gly Ser Gly Ile Trp Val
1               5                   10
```

CD137 ANTIBODIES FOR T-CELL ACTIVATION

CROSS-REFERENCE TO RELATED APPLICATIONS

This application claims the benefit of priority under 35 U.S.C. § 119(e) to U.S. Ser. No. 62/866,699 filed Jun. 26, 2019, and to U.S. Ser. No. 62/953,302 filed Dec. 24, 2019, both of which are herein incorporated by reference in their entirety.

INCORPORATION OF SEQUENCE LISTING

The material in the accompanying sequence listing is hereby incorporated by reference into this application. The accompanying sequence listing text file, name AP1100_2_Sequence_Listing. txt, was created on Jun. 24, 2020, and is 65,200 bytes. The file can be accessed using Microsoft Word on a computer that uses Windows OS.

BACKGROUND OF THE INVENTION

Field of the Invention

The present invention relates generally to antibodies and antigen binding fragments thereof and more specifically to antibodies and antigen binding fragments for enhancing T-cell function.

Background Information

Immunoregulation of the adaptive immune system has been an attractive field in cancer immunotherapy because of fewer side effects and long-term protection from cancer relapse. Two signals are generally required to fully activate T cells, an antigen-specific signal from the T-cell receptor (TCR), and a signal from a costimulatory molecule, such as CD28. In the past decade, additional co-stimulatory as well as co-inhibitory molecules were discovered on T cells that can positively or negatively modulate TCR signaling.

CD137 (4-1BB), a costimulatory molecule that belongs to the TNF receptor superfamily, was cloned from activated T cells in 1989 (Kwon & Weissman, 1989). The 4-1BB:4-1BBL pathway appears to amplify existing costimulatory signals, although engagement of 4-1BB in the presence of strong TCR signaling can induce IL-2 production in a CD28-independent manner. CD137 signaling has been demonstrated to boost TCR signaling, induce cytokine synthesis and T-cell proliferation, and inhibit activation-induced apoptosis. CD137 stimulation on T cells induces the NF-κB and PI3K/ERK signaling pathways responsible for preventing T-cell activation-induced apoptosis and inducing T-cell proliferation, respectively. Both CD4 and CD8 T cells respond to CD137 stimulation that results in enhanced expansion and effector function, while CD8 T cells preferentially respond to CD137 signaling by inducing greater cytokine production. In addition to expression on activated T cells, CD137 is expressed on multiple lineages of hematopoietic cells, including regulatory T cells, B cells, natural killer cells (NKs), monocytes, and dendritic cells (DCs). In DCs, stimulation of CD137 increases the secretion of IL-6 and IL-12, and more importantly it enhances the ability of DCs to stimulate T cell proliferation in response to alloantigens and nominal antigens. In NKs, CD137 stimulation promotes proliferation and IFN-γ production, but not cytolytic activity. Nevertheless, CD137-stimulated NK cells show a helper role in promoting the expansion of activated T cells.

In the clinic, the anti-CD137 agonist antibody Urelumab (BMS-663513) showed partial remission and some stabilization of disease. However, fatal hepatotoxicity resulted in termination of most trials. Trials of another anti-CD137 antibody, Utomilumab (PF-05082566), achieved an objective response rate of 3.8% in patients with solid tumors and 13.3% in patients with Merkel cell carcinoma, including complete and partial responses, without causing hepatotoxicity. Urelumab and Utomilumab show distinct properties. For agonist activity, Urelumab is strong and crosslinking-independent, whereas Utomilumab is weak and crosslinking-dependent. Crystal structures of Urelumab and Utomilumab with CD137 reveal distinct binding epitopes that affect the CD137-CD137L interaction. Distinct epitope recognition and CD137-CD137L binding blockade may result in the distinct potency and toxicity of these two anti-CD137 antibodies. However, ligand engagement does not determine CD137-mediated toxicity since the anti-4-1BB monoclonal antibodies (mAbs) 3H3 and 2A have opposing effects on CD137L binding, but show similar hepatotoxicity profiles. Recently, the engineered Fc region of a weak agonistic antibody has been shown to preferentially bind to FcγRIIB (at a low A/I FcγR-binding ratio), resulting in potent agonistic activity comparable to Urelumab without inducing hepatotoxicity. Agonistic anti-CD137 antibodies have been shown to have anticancer activities through potentiating T-cell cytotoxicity in a CD40-dependent manner. Moreover, antigen expression is required for anti-CD137 antibodies to regress established poorly antigenic tumors. Furthermore, the combination of anti-PD-1 and anti-CD137 antibodies showed enhanced antitumor activity in mouse tumor models through enhancing T-cell effector function and tumor infiltration compared to mono-treatment with each antibody. In addition to anti-cancer treatment, anti-CD137 agonist antibodies have also been shown to ameliorate experimental autoimmune encephalomyelitis and enhance antiviral immunity, depending on the timing of treatment.

PD-1 was first isolated from T cells undergoing apoptosis. Its ligand PD-L1 was later identified, and interaction between PD-1 and PD-L1 has been demonstrated to block T cell activation. PD-1 is not expressed on resting T cells, but is induced upon activation. Sustained expression of PD-1 is found on exhausted T cells in chronic infections and cancer. Under normal conditions, the PD-1/PD-L1 pathway is important for maintaining peripheral tolerance to prevent autoimmunity. However, the self-protective function of PD-L1 is hijacked in cancer, with PD-L1 expressed by various cancer cell types to evade immune system surveillance. Antibodies targeting PD-1/PD-L1 block inhibitory signaling and restore anti-cancer activities of T cells. The PD-1/PD-L1 pathway has been regarded as a dominant-negative regulator of effector function of anti-tumor T cells. In the clinic, blockade of this pathway has achieved a high objective response rate ranging from 35% to 87% in some cancer types, such as Hodgkin's lymphoma, Merkel cell carcinoma, and melanoma. Other cancer types, such as NSCLC, head and neck cancer, and renal cell carcinoma, achieved lower objective response rates in the range of 15% to 25%.

The combination of anti-PD-1 and anti-CD137 antibodies showed enhanced anti-tumor activity in mouse tumor models through enhancing T-cell effector function and tumor infiltration compared to mono-treatment with each antibody. In the clinic, the combination of Utomilumab (0.45-5.0 mg/kg) and Pembrolizumab showed a synergistic anti-tumor effect in patients with advanced solid tumors with no dose-limiting toxicity.

Based on the immune modulating roles of CD137, anti-human 4-1BB agonist antibodies could be used for the treatment of cancer and autoimmune and infectious diseases. However, the use of anti-human-4-1BB agonist antibodies is limited due to liver toxicity. Moreover, no effective treatments have been described that combine activation of the 4-1BB:4-1BBL pathway in the absence of liver toxicity with blocking immune inhibitory or tumor signaling pathways. Thus, there exists a need for effective engagement of the 4-1BB:4-1BBL pathway in combination with relieving inhibition of immune activation or in combination with inhibiting tumor cell signaling.

SUMMARY OF THE INVENTION

The present invention is based on the seminal discovery that anti-CD137 antibodies can be generated that possess potent cross-linking dependent agonist activity and that might circumvent liver toxicity seen in clinical trials. The present invention is further based on the discovery that bispecific antibodies targeting PD-L1 and CD137 possess extraordinary activity to boost T-cell effector function and inhibit tumor growth in vivo better than mono-treatment or combination treatment with each antibody. Bispecific antibodies may have a unique anti-CD137 single chain variable fragment (scFv) that activates T cells upon crosslinking via the other arm of the bispecific antibody that binds to PD-L1, for example. The bispecific antibody may also be targeted to non-PD-L1-expressing tumors by changing the anti-PD-L1 arm to other tumor-specific binders, such as anti-Her2 or an anti-tumor-specific glycan, as provided herein. A bispecific antibody that induces target-dependent T-cell activation may avoid hepatotoxicity while maintaining the anti-tumor potency of anti-CD137 monoclonal antibodies.

In some embodiments, the present invention provides three agonist antibodies or antigen binding fragments thereof: anti-CD137 antibody clone 15 (CD137 #15), anti-CD137 antibody clone 31 (CD137 #31), and anti-CD137 antibody clone 54 (CD137 #54). In one aspect, anti-CD137 antibodies provided herein include a heavy chain variable ($V_H$) region including an amino acid sequence with at least 80% sequence identity to a sequence selected from SEQ ID NO:1, SEQ ID NO:9, or SEQ ID NO:17; and a light chain variable ($V_L$) region including an amino acid sequence with at least 80% sequence identity to a sequence selected from SEQ ID NO:2, SEQ ID NO:10, or SEQ ID NO:18. In another aspect, the antibody or antigen binding fragment having a $V_H$ region that includes an amino acid sequence having at least 80% identity to SEQ ID NO:1 and a $V_L$ region that includes an amino acid sequence having at least 80% identity to SEQ ID NO:2 includes (a) $V_H$ CDR-H1, CDR-H2, and CDR-H3, wherein CDR-H1 includes an amino acid sequence having at least 80% identity to SEQ ID NO:3, wherein CDR-H2 includes an amino acid sequence having at least 80% identity to SEQ ID NO:4, and wherein CDR-H3 includes an amino acid sequence having at least 80% identity to SEQ ID NO:5; and (b) $V_L$ CDR-L1, CDR-L2, and CDR-L3, wherein CDR-L1 includes an amino acid sequence having at least 80% identity to SEQ ID NO:6, wherein CDR-L2 includes an amino acid sequence having at least 80% identity to SEQ ID NO:7, and wherein CDR-L3 includes an amino acid sequence having at least 80% identity to SEQ ID NO:8.

In another aspect, the antibody or antigen binding fragment thereof having a $V_H$ region that includes an amino acid sequence having at least 80% identity to SEQ ID NO:9 and a $V_L$ region that includes an amino acid sequence having at least 80% identity to SEQ ID NO:10 includes (a) $V_H$ CDR-H1, CDR-H2, and CDR-H3, wherein CDR-H1 includes an amino acid sequence having at least 80% identity to SEQ ID NO:11, wherein CDR-H2 includes an amino acid sequence having at least 80% identity to SEQ ID NO:12, and wherein CDR-H3 includes an amino acid sequence having at least 80% identity to SEQ ID NO:13; and (b) $V_L$ CDR-L1, CDR-L2, and CDR-L3, wherein CDR-L1 includes an amino acid sequence having at least 80% identity to SEQ ID NO:14, wherein CDR-L2 includes an amino acid sequence having at least 80% identity to SEQ ID NO:15, and wherein CDR-L3 includes an amino acid sequence having at least 80% identity to SEQ ID NO:16.

In yet another aspect, the antibody or antigen binding fragment thereof having a $V_H$ region that includes an amino acid sequence having at least 80% identity to SEQ ID NO:17 and a $V_L$ region that includes an amino acid sequence having at least 80% identity to SEQ ID NO:18 includes (a) $V_H$ CDR-H1, CDR-H2, and CDR-H3, wherein CDR-H1 includes an amino acid sequence having at least 80% identity to SEQ ID NO:19, wherein CDR-H2 includes an amino acid sequence having at least 80% identity to SEQ ID NO:20, and wherein CDR-H3 includes an amino acid sequence having at least 80% identity to SEQ ID NO:21; and (b) $V_L$ CDR-L1, CDR-L2, and CDR-L3, wherein CDR-L1 includes an amino acid sequence having at least 80% identity to SEQ ID NO:22, wherein CDR-L2 includes an amino acid sequence having at least 80% identity to SEQ ID NO:23, and wherein CDR-L3 includes an amino acid sequence having at least 80% identity to SEQ ID NO:24.

In one aspect, antibodies or antigen binding fragments thereof provided herein include an Fc domain. In another aspect, the Fc domain is an IgG, IgE, IgM, IgD, IgA, or IgY domain. In yet another aspect, the IgG domain is an IgG1, IgG2, IgG3, or IgG4 domain. In an additional aspect, the IgG1 domain includes an amino acid sequence of SEQ ID NO:26. In certain aspects, IgG1 includes point mutations compared to wild-type IgG1 that modify or reduce antibody-dependent cellular cytotoxicity (ADCC) and/or complement-dependent cytotoxicity (CDC). Exemplary point mutations include K297A and K322A mutations. In yet another aspect, the IgG4 domain includes an amino acid sequence of SEQ ID NO:25. In a further aspect, antigen fragments provided herein include an scFv, an F(ab)2, or an Fab.

In an embodiment, the present disclosure also provides a pharmaceutical composition that includes any one of the antibodies or an antigen binding fragment thereof provided herein. In one aspect, antibodies or antigen binding fragments of pharmaceutical compositions provided herein include a pharmaceutically acceptable carrier conjugated to the C-terminus of one or more polypeptides of the antibody or antigen binding fragment thereof. In another aspect, pharmaceutical compositions provided herein include a bispecific antibody.

In one embodiment, the present disclosure also provides a method of treating cancer that includes administering to a subject in need thereof an effective amount of an antibody or antigen binding fragment thereof provided herein, or an effective amount of a bispecific antibody provided herein. In one aspect, the cancer is selected from prostate cancer, lung cancer, Non-Small Cell Lung Cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, or leukemia.

In one embodiment, provided herein are bispecific antibodies that include a first antigen binding region and a second antigen binding region, wherein the first antigen binding region binds to CD137. In one aspect, bispecific antibodies provided herein include (i) a $V_H$ region including an amino acid sequence having at least 80% identity to a sequence selected from SEQ ID NO:1; SEQ ID NO:9; and SEQ ID NO:17; and (ii) a $V_L$ region including an amino acid sequence having at least 80% identity to an N-terminal sequence of about 100 to 120 amino acids of a sequence selected from SEQ ID NO:2; SEQ ID NO:10; and SEQ ID NO:18, wherein the second antigen binding region binds to an immune checkpoint molecule, an immune stimulatory molecule, or a tumor antigen.

In one aspect, bispecific antibodies provided herein include a heavy chain sequence of SEQ ID NO:31 or SEQ ID NO:32. In another aspect, bispecific antibodies provided herein further include a light chain sequence of SEQ ID NO:30. In one aspect, bispecific antibodies provided herein include a heavy chain sequence of SEQ ID NO:36. In another aspect, bispecific antibodies provided herein further include a light chain sequence of SEQ ID NO:35. In one aspect, bispecific antibodies provided herein include a heavy chain sequence of SEQ ID NO:38. In another aspect, bispecific antibodies provided herein further include a light chain sequence of SEQ ID NO:37. In one aspect, bispecific antibodies provided herein include a heavy chain sequence of SEQ ID NO:40. In another aspect, bispecific antibodies provided herein further include a light chain sequence of SEQ ID NO:39.

In one aspect, bispecific antibodies provided herein include a first antigen binding region having (a) a $V_H$ region including an amino acid sequence of SEQ ID NO:9 and a $V_L$ region including an amino acid sequence of about 100 to 120 amino acids of an N-terminal sequence of SEQ ID NO:10; or (b) a $V_H$ region including an amino acid sequence of SEQ ID NO:17 and a $V_L$ region including an amino acid sequence of about 100 to 120 amino acids of an N-terminal sequence of SEQ ID NO:18. In another aspect, the second antigen binding region binds to an antigen selected from PD-L1, PD-1, CTLA-4, LAG3, CD28, CD40, CD137, CD27, ICOS, Her2, or a glycan. In yet another aspect, the second antigen binding region binds to PD-L1, Her2, or a glycan.

In one aspect, the present invention discloses that anti-PD-L1 #6-CD137 #54 bispecific antibody (bsAb) could act as a platform to exert target-dependent T cell activation through the crosslinking-dependent agonist activity of an anti-CD137 #54 single chain.

In another aspect, bispecific antibodies that bind to CD137 and PD-L1 are modified to bind to CD137 and other targets expressed on tumors, including immune regulatory molecules and tumor-specific markers, such as Her2 or a tumor-specific glycan.

In one aspect, the first antigen binding region and the second antigen binding region of bispecific antibodies provided herein include an Fc domain, an Fab fragment, a single chain variable fragment (scFv), or any combination thereof. In yet another aspect, the scFv includes (i) a $V_H$ region that includes an amino acid sequence of SEQ ID NO:9 and a $V_L$ region that includes an amino acid sequence of about 100 to 120 amino acids of an N-terminal sequence of SEQ ID NO:10; or (ii) a $V_H$ region that includes an amino acid sequence of SEQ ID NO:17 and a $V_L$ region that includes an amino acid sequence of about 100 to 120 amino acids of an N-terminal sequence of SEQ ID NO:18. In a further aspect, bispecific antibodies provided herein include a linker between the $V_H$ region and the $V_L$ region of the scFv. In an additional aspect, the scFv includes an amino acid sequence SEQ ID NO:33 or SEQ ID NO:34.

In one aspect, bispecific antibodies provided herein include an Fc domain. In another aspect, the Fc domain is an IgG domain, an IgE domain, an IgM domain, and IgD domain, an IgA domain, or an IgY domain. In yet another aspect, the Fc domain is an IgG domain. In a further aspect, the IgG domain is an IgG1 domain, an IgG2 domain, an IgG3 domain, or an IgG4 domain.

In one aspect, the scFv is linked to the C-terminus of the Fc domain. In another aspect, bispecific antibodies provided herein include a linker between the Fab domain and the scFv domain. In a further aspect, the Fab fragment is linked to the N-terminus of the Fc domain. In yet a further aspect, the Fab includes a PD-L1 binding site, a Her2 binding site, or a glycan binding site and the scFv includes a CD137 binding site.

In one embodiment, the invention provides an antibody-drug conjugate that includes a therapeutic agent and an antibody, including any bispecific antibody, provided herein or an antigen binding fragment thereof. In one aspect, the therapeutic agent is covalently linked to the antibody or the antigen binding fragment via a linker.

In one embodiment, provided herein are pharmaceutical compositions that include any bispecific antibody provided herein and at least one pharmaceutically acceptable carrier.

In one embodiment, the invention provides an isolated amino acid sequence as set forth in SEQ ID NOs:1-26. In another embodiment, the invention provides an isolated amino acid sequence as set forth in SEQ ID NOs:30-40.

In one embodiment, the present disclosure also provides an isolated nucleic acid sequence encoding the antibody, an antigen-binding fragment thereof, or the bispecific antibody of the invention. In another embodiment, the invention provides an isolated nucleic acid encoding any one of SEQ ID NOs:1-26. In another embodiment, the invention provides an isolated nucleic acid sequence encoding any one of SEQ ID NOs:30-40.

DETAILED DESCRIPTION OF THE INVENTION

Figure 1:
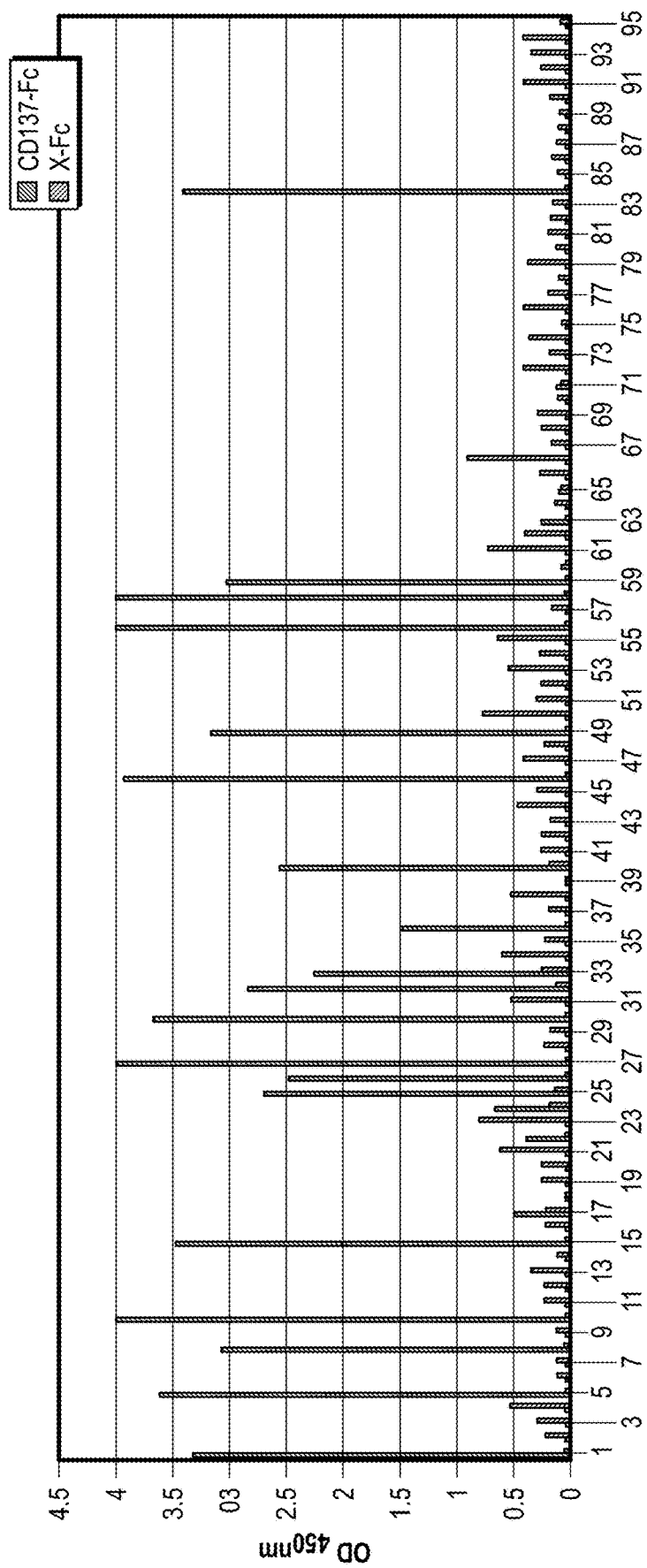
FIG. 1 shows the screening for phage clones targeted to CD137 by direct ELISA.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Provided herein, in some embodiments, are antibodies and antigen binding fragments thereof that bind CD137. Also provided herein are amino sequences of antibodies that bind CD137. As used herein, the term "antibody" refers to an immunoglobulin molecule that has the ability to specifically bind to an antigen. The term "antibody" includes, but is not limited to, monoclonal antibodies, polyclonal antibodies, human antibodies, humanized antibodies, chimeric antibodies, bispecific antibodies, and anti-idiotypic antibodies, unless context clearly indicates otherwise. In one aspect, antibodies provided herein include monoclonal antibodies. Antibodies provided herein include any isotype and class (e.g., IgG, IgE, IgM, IgD, IgA and IgY), or subclass (e.g., IgG1, IgG2, IgG3, IgG4, IgA1 and IgA2). As used herein, "antigen binding fragment" means a fragment or portion of an immunoglobulin molecule or antibody that has the ability to specifically bind to the same antigen as the immunoglobulin molecule or antibody. Exemplary antigen binding fragments include scFv, Fab, or F(ab)2 fragments. As used herein, "antigen binding region" means the part of an antibody or immunoglobulin molecule that binds to antigens or proteins by contacting the antigen or protein, for example. An antigen binding region generally includes heavy chain variable ($V_H$) regions and light chain variable ($V_L$) regions. An antigen binding region generally includes one or more antigen binding sites or paratopes.

Antibodies provided herein have a $V_H$ region including an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to a sequence of SEQ ID NO:1; SEQ ID NO:9; or SEQ ID NO:17. Antibodies provided herein also include an $V_L$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to a sequence of SEQ ID NO:2; SEQ ID NO:10; or SEQ ID NO:18.

In general, "sequence identity" or "sequence homology," which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby or the amino acid sequence of a polypeptide, and comparing these sequences to a second nucleotide or amino acid sequence. As used herein, the term "percent (%) sequence identity" or "percent (%) identity," also including "homology," refers to the percentage of amino acid residues or nucleotides in a sequence that are identical with the amino acid residues or nucleotides in a reference sequence after aligning the sequences and introducing gaps, if necessary, to achieve the maximum percent sequence identity, and not considering any conservative substitutions as part of the sequence identity. Thus, two or more sequences (polynucleotide or amino acid) can be compared by determining their "percent identity," also referred to as "percent homology." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values in between. Percent identities between a reference sequence and a claimed sequence can be at least 80%, at least 85%, at least 90%, at least 95%, at least 98%, at least 99%, at least 99.5%, or at least 99.9%. In general, an exact match indicates 100% identity over the length of the reference sequence. Additional programs and methods for comparing sequences and/or assessing sequence identity include the Needleman-Wunsch algorithm (see, e.g., the EMBOSS Needle aligner available at ebi.ac.uk/Tools/psa/emboss_needle/, optionally with default settings), the Smith-Waterman algorithm (see, e.g., the EMBOSS Needle alinger available at ebi.ac.uk/Tools/psa/emboss_water/, optionally with default settings), the similarity search method of Pearson and Lipman, 1988, Proc. Natl. Acad. Sci. USA 85, 2444, or computer programs which use these algorithms (GAP, BESTFIT, FASTA, BLAST P, BLAST N and TFASTA in Wisconsin Genetics Software Package, Genetics Computer Group, 575 Science Drive, Madison, Wis.). In some aspects, reference to percent sequence identity refers to sequence identity as measured using BLAST (Basic Local Alignment Search Tool). In other aspects, ClustalW is used for multiple sequence alignment. Optimal alignment may be assessed using any suitable parameters of a chosen algorithm, including default parameters.

In one aspect, the antibody or antigen binding fragment thereof has a $V_H$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:1 and a $V_L$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:2. SEQ ID NO:1 provides an amino acid sequence that includes the variable region of anti-CD137 antibody clone #15 heavy chain. SEQ ID NO: 2 provides an amino acid sequence that includes the variable region of anti-CD137 clone #15 light chain.

The antigen binding region of an antibody or antigen binding fragment thereof generally includes complementarity determining regions (CDRs). "Complementarity determining region (CDR)" refers to hypervariable regions of $V_H$ and $V_L$. CDRs include the target protein or antigen binding site of an antibody that confers specificity for protein or antigen binding. $V_H$ and $V_L$ generally include three sequentially numbered CDRs. As used herein, CDR-H1, CDR-H2, and CDR-H3 refer to three consecutively arranged CDRs of the heavy chain variable region ($V_H$), as numbered from the N-terminus of the heavy chain polypeptide. As used herein, CDR-L1, CDR-L2, and CDR-L3 refer to three consecutively arranged CDRs of the light chain variable region ($V_L$), as numbered from the N-terminus of the light chain polypeptide.

In one aspect, the antigen binding region of the antibody or antigen binding fragment thereof having a $V_H$ region that includes an amino acid sequence having at least about 80% identity to SEQ ID NO:1 and a $V_L$ region that includes an amino acid sequence having at least about 80% identity to SEQ ID NO:2 has a CDR-H1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:3, a CDR-H2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:4, and a CDR-H3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:5. In another aspect, the antigen binding region of the antibody or antigen binding fragment thereof having a $V_H$ region that includes an amino acid sequence having at least about 80% identity to SEQ ID NO:1 and a $V_L$ region that includes an amino acid sequence having at least about 80% identity to SEQ ID NO:2 has a CDR-L1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:6, a CDR-L2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:7, and a CDR-L3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:8.

In some aspects, the antibody or antigen binding fragment thereof includes a $V_H$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:9 and a $V_L$ region that includes an amino acid sequence having at least about 80%, identity at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:10. SEQ ID NO:9 provides an amino acid sequence that includes the variable region of anti-CD137 antibody clone #31 heavy chain. SEQ ID NO: 10 provides an amino acid sequence that includes the variable region of anti-CD137 clone #31 light chain.

In one aspect, the antigen binding region of the antibody or antigen binding fragment thereof that includes a $V_H$ region including an amino acid sequence having at least about 80% identity to SEQ ID NO:9 and a $V_L$ region including an amino acid sequence having at least about 80% identity to SEQ ID NO:10 has a CDR-H1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:11, a CDR-H2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:12, and a CDR-H3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:13. In another aspect, the antigen binding region of the antibody or antigen binding fragment thereof that includes a $V_H$ region including an amino acid sequence having at least about 80% identity to SEQ ID NO:9 and a $V_L$ region that includes an amino acid sequence having at least about 80%, identity to SEQ ID NO:10 has a CDR-L1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:14, a CDR-L2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:15, and a CDR-L3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:16.

In some aspects, the antibody or antigen binding fragment thereof has a $V_H$ region that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:17 and a $V_L$ region that includes an amino acid sequence having at least about 80%, identity at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:18. SEQ ID NO:17 provides an amino acid sequence that includes the variable region of anti-CD137 antibody clone #54 heavy chain. SEQ ID NO: 18 provides an amino acid sequence that includes the variable region of anti-CD137 clone #54 light chain.

In one aspect, the antigen binding region of the antibody or antigen binding fragment thereof that includes a $V_H$ region including an amino acid sequence having at least about 80% identity to SEQ ID NO:17 and a $V_L$ region including an amino acid sequence having at least about 80% identity to SEQ ID NO:18 has a CDR-H1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:19, a CDR-H2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:20, and a CDR-H3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:21. In another aspect, the antigen binding region of the antibody or antigen binding fragment thereof that includes a $V_H$ region including an amino acid sequence having at least about 80% identity to SEQ ID NO:17 and a $V_L$ region including an amino acid sequence having at least about 80%, identity to SEQ ID NO:18 has a CDR-L1 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:22, a CDR-L2 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:23, and a CDR-L3 that includes an amino acid sequence having at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, at least about 99% identity, at least about 99.5% identity, at least about 99.9% identity, and any number or range in between, to SEQ ID NO:24.

Antibodies or antigen binding fragments thereof provided herein further include an Fc domain. As used herein, the term Fc domain refers to an antibody region that includes at least a hinge region, a CH2 domain, and a CH3 domain, unless context clearly indicates otherwise. The terms Fc domain and Fc region may be used interchangeably, unless context clearly indicates otherwise. In certain aspects, the Fc domain is an IgG domain, an IgE domain, an IgM domain, and IgD domain, an IgA domain, or an IgY domain. Fc domains of any sequence and from any species can be used, including human, ape, monkey, mouse, rabbit, goat, sheep, guinea pig, horse, and others. In certain aspects, Fc domains are engineered, i.e. non-naturally occurring or recombinant Fc domains generated using techniques of molecular biology, for example. In some aspects, the IgG domain is an IgG1 domain, an IgG2 domain, an IgG3 domain, or an IgG4 domain. In one aspect, the IgG4 domain includes an amino acid sequence of SEQ ID NO:25. In another aspect, the IgG1 domain includes an amino acid sequence of SEQ ID NO:26. In one aspect, the Fc domain is human.

Also provided herein, in some embodiments, are pharmaceutical compositions including any of the antibodies or antigen binding fragments thereof provided herein and a pharmaceutically acceptable carrier. In some aspects, the pharmaceutically acceptable carrier is conjugated to the C-terminus of one or more polypeptides of the antibody or antigen binding fragment. Any suitable means of conjugating the pharmaceutically acceptable carrier can be used, including covalent conjugation and use of linkers, for example.

In some embodiments, provided herein are isolated amino acid sequences as set forth in SEQ ID NOs:1-26. Also provided herein, in some embodiments, are isolated nucleic acid sequences that encode any one of the amino acid sequences of SEQ ID NOs:1-26.

In some embodiments, methods of treating cancer in a subject are provided herein. In some aspects, methods of treating cancer include administering to a subject an amount of any of the antibodies or antigen binding fragments thereof provided herein that bind CD137, effective for treating the cancer. In some aspects, the cancer is prostate cancer, lung cancer, non-small cell lung cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, or leukemia.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, includes any treatment of a disease in a mammal, particularly in a human, and includes: (a) preventing the disease from occurring in a subject, including a subject which is predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some aspects, for prophylactic benefit, treatment or compositions for treatment are administered to a subject at risk of developing a particular disease, or to a subject reporting one or more of the physiological symptoms of a disease, even though a diagnosis of this disease may not have been made. The methods of the present disclosure may be used with any mammal or other animal. In some aspects, treatment results in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "subject" refers to any individual or patient on which the methods disclosed herein are performed. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, the term "effective amount" or "therapeutically effective amount" refers to that amount of an antibody, an antigen binding fragment thereof, or other composition described herein that is sufficient to effect the intended application, including but not limited to disease treatment, as defined herein. The therapeutically effective amount may vary depending upon the intended treatment application (e.g., in vivo), or the patient and disease condition being treated, e.g., the weight and age of the patient, the severity of the disease condition, the manner of administration and the like, which can readily be determined by one of ordinary skill in the art. The term also applies to a dose that will induce a particular response in a target cell. The specific dose will vary depending on the particular antibody, an antigen binding fragment thereof, or other composition chosen, the dosing regimen to be followed, whether it is administered in combination with other compounds, timing of administration, the tissue to which it is administered, and the physical delivery system in which it is carried.

In some aspects, antibodies of the invention or antigen binding fragments thereof are used as a monotherapy or combined with other therapeutic agents such as radiotherapy, cytotoxic chemotherapy, and other immunoregulatory agents, such as vaccines, interleukins, cytokines, chemokines, and biologics as a combination therapy. Exemplary interleukins for immune therapy include IL-1, IL-2, IL-3, IL-4, IL-5, IL-6, IL-7, IL-8, IL-10, IL-12, IL-15, IL-18, IL-21, and IL-23. Exemplary cytokines for immune therapy include interferons, TNF-α, TGF-β, G-CSF, and GM-CSF. Exemplary chemokines for immune therapy include CCL3, CCL26, and CXCL7. Exemplary biologics include CAR T-cell therapy, tumor-infiltrating lymphocyte (TIL) therapy, and monoclonal antibodies, such as alemtuzumab (CAMPATH), trastuzumab (HERCEPTIN), ibritumomab tiuxetan (ZEVALIN), brentuximab vedotin (ADCETRIS), ado-trastuzumab emtansine (KADCYLA), blinatumomab (BLINCYTO), bevacizumab (AVASTIN), and cetuximab (ERBITUX). Antibodies also include checkpoint inhibitors, including PD-1 inhibitors, such as pembrolizumab (KEYTRUDA), nivolumab (OPDIVO), and cemiplimab (LIBTAYO), for example, PD-L1 inhibitors, such as atezolizumab (TECENTRIQ), avelumab (BAVENCIO) and durvalumab (IMFINZI), for example, CTLA-4 inhibitors, such as iplimumab (YERVOY), for example, and other checkpoint inhibitors, such as an anti B7-H3 antibody (MGA271), an anti-KIR antibody (lirilumab) and an anti-LAG3 antibody (BMS-986016), for example.

In some embodiments, the invention further provides the expression, purification and characterization of anti-CD137 agonist antibodies, as detailed in the examples below. A signal sequence can be included in expression constructs for antibodies provided herein. Any suitable signal sequence can be used, such as a sequence of SEQ ID NO:27. In some aspects, T cells treated with anti-PD-L1 antibody together with anti-CD137 antibodies provided herein showed a further increase in T-cell effector function. Without being limited by theory, this indicates that combination treatment or treatment with bispecific antibodies targeting both CD137 and PD-L1 may overcome a lower response rate of monotherapy seen with each antibody alone in clinical trials. In addition to anti-PD-L1 antibody, a second antibody for combination treatment that targets other immune potentiating antigens, such as CD40 or CTLA-4, or treatment with a bispecific antibody targeting CD137 and a second antigen such as PD-L1, CD40, or CTLA-4, for example, can be used.

Bispecific molecules, such as bispecific antibodies (bs-Abs), provide a means for simultaneously targeting multiple epitopes on the same or different molecular targets with a single therapeutic agent. Without being limited by theory, bispecific molecules as cancer therapeutics have the potential to confer novel or more potent activities, lower the cost of goods, and facilitate the development of new therapeutic regimens as compared to a mixture of two monoclonal antibodies (mAbs), for example.

Accordingly, also provided herein is the expression, purification, and characterization of bi-functional proteins, including bispecific antibodies. As used herein, the term "bi-functional protein" refers to a protein that has at least two functions. A non-limiting example of a bi-functional protein includes a bispecific antibody that is capable of binding to two antigens. Bispecific antibodies provided herein can include isolated, functional scFv fragments that bind to CD137 and that are fused to the C-terminus of the Fc domain of an anti-PD-L1 antibody, for example. In some aspects, a C-terminally positioned scFv that binds CD137 in fusion constructs provided herein is fused to an Fc domain of an antibody that binds to other immunoregulatory molecules, such as CD40 or CTLA-4, for example. In other aspects, a C-terminally positioned scFv can bind to an immunoregulatory molecule, such as CD40 or CTLA-4, for example.

Provided herein, in some embodiments, are bispecific antibodies that include a first antigen binding region and a second antigen binding region. Generally, the first antigen binding region and the second antigen binding region specifically bind to different antigens or targets. In some aspects, the first antigen binding region and the second antigen binding region bind to different epitopes in the same antigen or target.

In an embodiment, bispecific antibodies provided herein include a first antigen binding region that binds to CD137. The first antigen binding region includes a $V_H$ region that includes an amino acid sequence having at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity, at least 99.5% identity, at least 99.9% identity, and any number or range in between, to a sequence selected from SEQ ID NO:1; SEQ ID NO:9; and SEQ ID NO:17 and a $V_L$ region that includes an amino acid sequence having at least 80% identity, at least 85% identity, at least 90% identity, at least 91% identity, at least 92% identity, at least 93% identity, at least 94% identity, at least 95% identity, at least 96% identity, at least 97% identity, at least 98% identity, at least 99% identity, at least 99.5% identity, at least 99.9% identity, and any number or range in between, to about 100 to 120 amino acids of an N-terminal sequence of a sequence selected from SEQ ID NO:2; SEQ ID NO:10; and SEQ ID NO:18. In some aspects, the second antigen binding region of bispecific antibodies provided herein binds to an immune checkpoint molecule, an immune stimulatory molecule, or a tumor antigen.

Any number of amino acids of sequences as set forth in SEQ ID NO:1, SEQ ID NO:9, and SEQ ID NO:17 that include a $V_H$ region or as set forth in SEQ ID NO:2, SEQ ID NO:10, or SEQ ID NO:18 that include a $V_L$ region can be included in bispecific antibodies. N-terminal or C-terminal sequences of sequences provided herein having a $V_H$ region or a $V_L$ region can be included in bispecific antibodies. In one aspect, about 100 to 105 amino acids, about 100 to 110 amino acids, about 100 to 115 amino acids, about 100 to 120 amino acids, about 100 to 125 amino acids, and any number or range in between, of an N-terminal or of a C-terminal sequence of SEQ ID NO:1, SEQ ID NO:2, SEQ ID NO:9, SEQ ID NO:10, SEQ ID NO:17, or SEQ ID NO:18 is included in bispecific antibodies provided herein. In another aspect, bispecific antibodies include a sequence of SEQ ID NO:1, SEQ ID NO:9, or SEQ ID NO:17. In yet another aspect, bispecific antibodies include about 100 to 120 amino acids of an N-terminal sequence of SEQ ID NO:2, SEQ ID NO:10, or SEQ ID NO:18. In yet a further aspect, bispecific antibodies include about 112 amino acids of an N-terminal sequence of SEQ ID NO:10 or about 108 amino acids of an N-terminal sequence of SEQ ID NO:18.

In one aspect, the first antigen binding region of bispecific antibodies provided herein includes a $V_H$ region having an amino acid sequence of SEQ ID NO:9 and a $V_L$ region having an amino acid sequence of about 100 to 120 amino acids of an N-terminal sequence of SEQ ID NO:10. In another aspect, the first antigen binding region of bispecific antibodies provided herein includes a $V_H$ region having an amino acid sequence of SEQ ID NO:17 and a $V_L$ region having an amino acid sequence of about 100 to 120 amino acids of an N-terminal sequence SEQ ID NO:18.

In some aspects, the second antigen binding region of bispecific antibodies provided herein binds to an immune checkpoint molecule, an immune stimulatory molecule, or a tumor antigen. As used herein, the term "immune checkpoint molecule" refers to any molecule that inhibits or negatively regulates immune responses. In one aspect, binding of the second antigen binding region to an immune checkpoint molecule inhibits the immune checkpoint molecule. Exemplary immune checkpoint molecules include PD-L1, PD-1, CTLA-4, and LAG3. As used herein, the term "immune stimulatory molecule" refers to any molecule that induces, enhances, or positively regulates immune responses. Exemplary immune stimulatory molecules include CD28, CD40, CD137, CD27, and ICOS. In some aspects, binding of the second antigen binding region to an immune stimulatory molecule activates the immune stimulatory molecule, resulting in increased signaling and increased immune activation, for example. As used herein, the term "tumor antigen" refers to any antigen that is present on the surface of a tumor cell or expressed in a tumor cell. Exemplary tumor antigens include products of mutated oncogenes, products or mutated tumor suppressor genes, products of mutated genes other than oncogenes or tumor suppressors, tumor antigens produced by oncogenic viruses, altered cell surface glycolipids and glycoproteins, oncofetal antigens, and others. Tumor antigens also include immune regulatory molecules, such as immune checkpoint inhibitors and immune stimulatory molecules. Accordingly, in some aspects, the tumor antigen the second antigen binding region of bispecific antibodies provided herein binds to functions as an immune regulatory molecule. In one aspect, binding of the second antigen binding region to a tumor antigen results in targeting an immune cell, such as a T cell, to a tumor cell, for example.

Any combination of first and second antigen binding regions can be included in bispecific antibodies provided herein, including first and second antigen binding regions that bind to any immune checkpoint molecule, any immune stimulatory molecule, or any tumor antigen, for example. Accordingly, in some aspects, the second antigen binding region of bispecific antibodies provided herein binds to any immune checkpoint molecule, any immune stimulatory molecule, or any tumor antigen. In some aspects, the first and second antigen binding regions bind to the same molecule. For example, the first and second antigen binding regions may bind to the same or to a different epitope of the same molecule. In other aspects, the first and second antigen binding regions bind to different molecules.

In some aspects, the second antigen binding region binds to an antigen selected from PD-L1, PD-1, CTLA-4, LAG3, CD28, CD40, CD137, CD27, ICOS, human epidermal growth factor receptor 2 (Her2), or a glycan. Exemplary glycans include N-glycans, O-glycans, and glycosphingolipids. A glycan may be expressed exclusively in cancer cells, such as GloboH, for example. In one aspect, the second antigen binding region binds to PD-L1. In another aspect, the second antigen binding region binds to Her2. In yet another aspect, the second antigen binding region binds to a glycan. In a further aspect, the glycan is GloboH. Expanding the repertoire of bispecific antibodies to bind to CD137 and antigens expressed on tumors in addition to or other than PD-L1 allows for targeting bispecific antibodies to cancer types that do not express PD-L1, for example.

Figure 16:
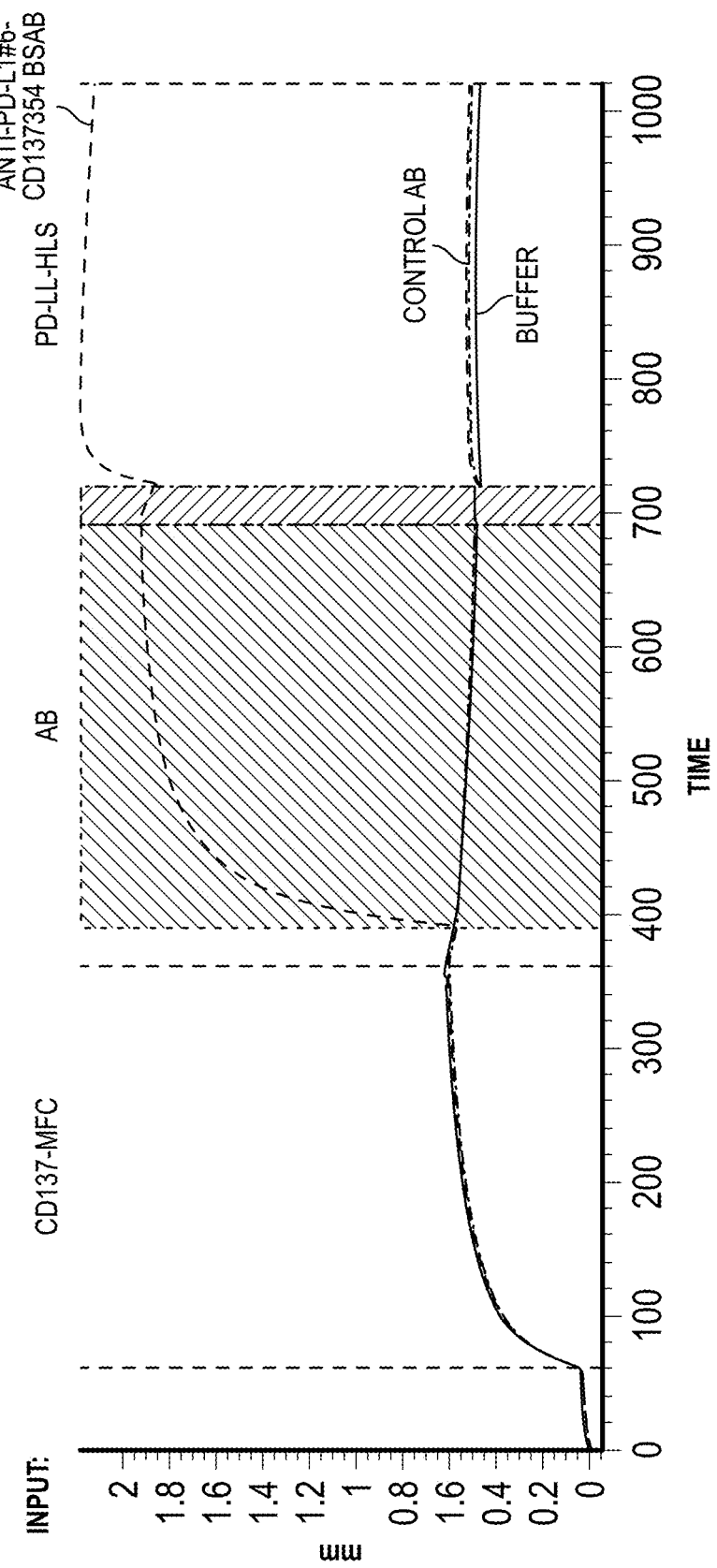
FIG. 16 shows that anti-PD-L1-CD137 bsAbs simultaneously recognize CD137 and PD-L1, as seen by ForteBio® biosensor analysis.
Figure 16:
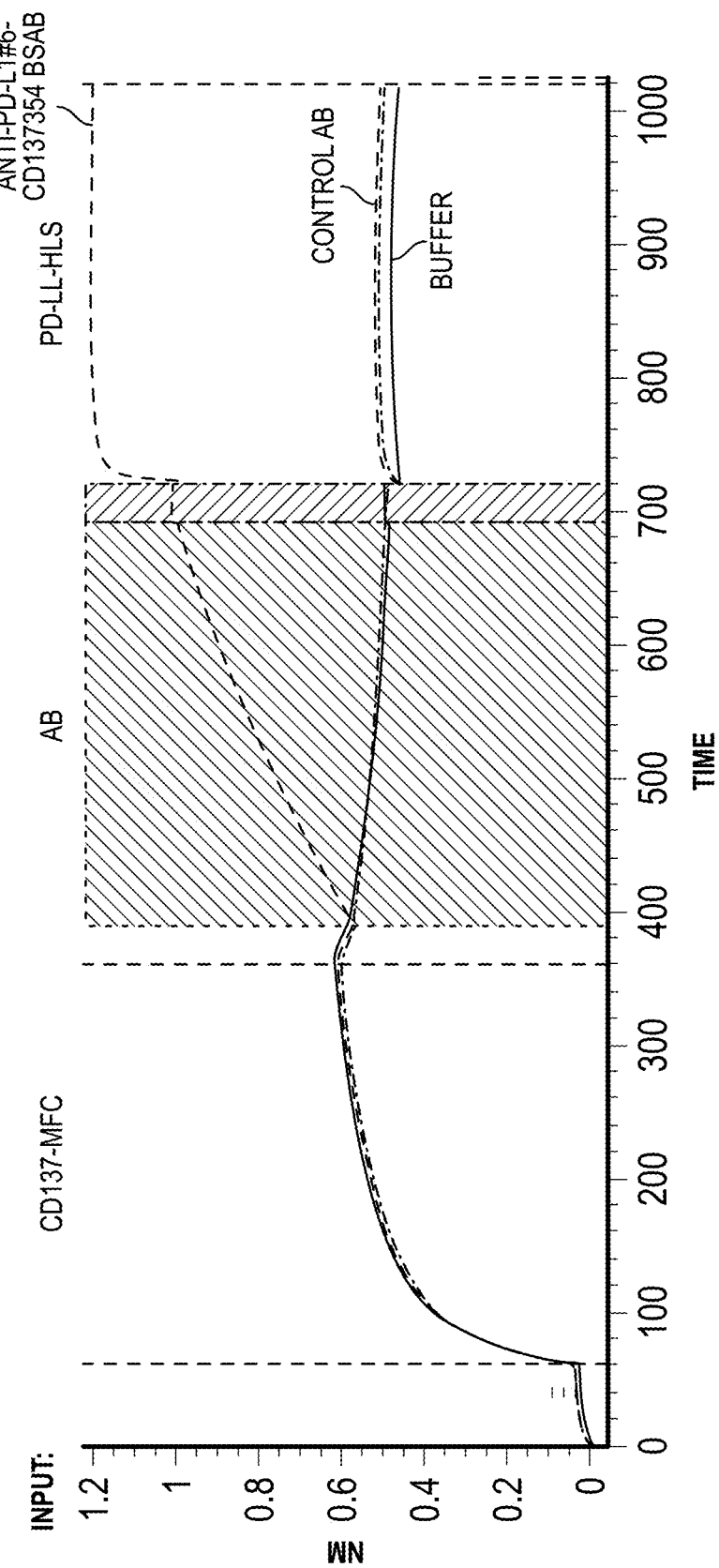
Figure 23:
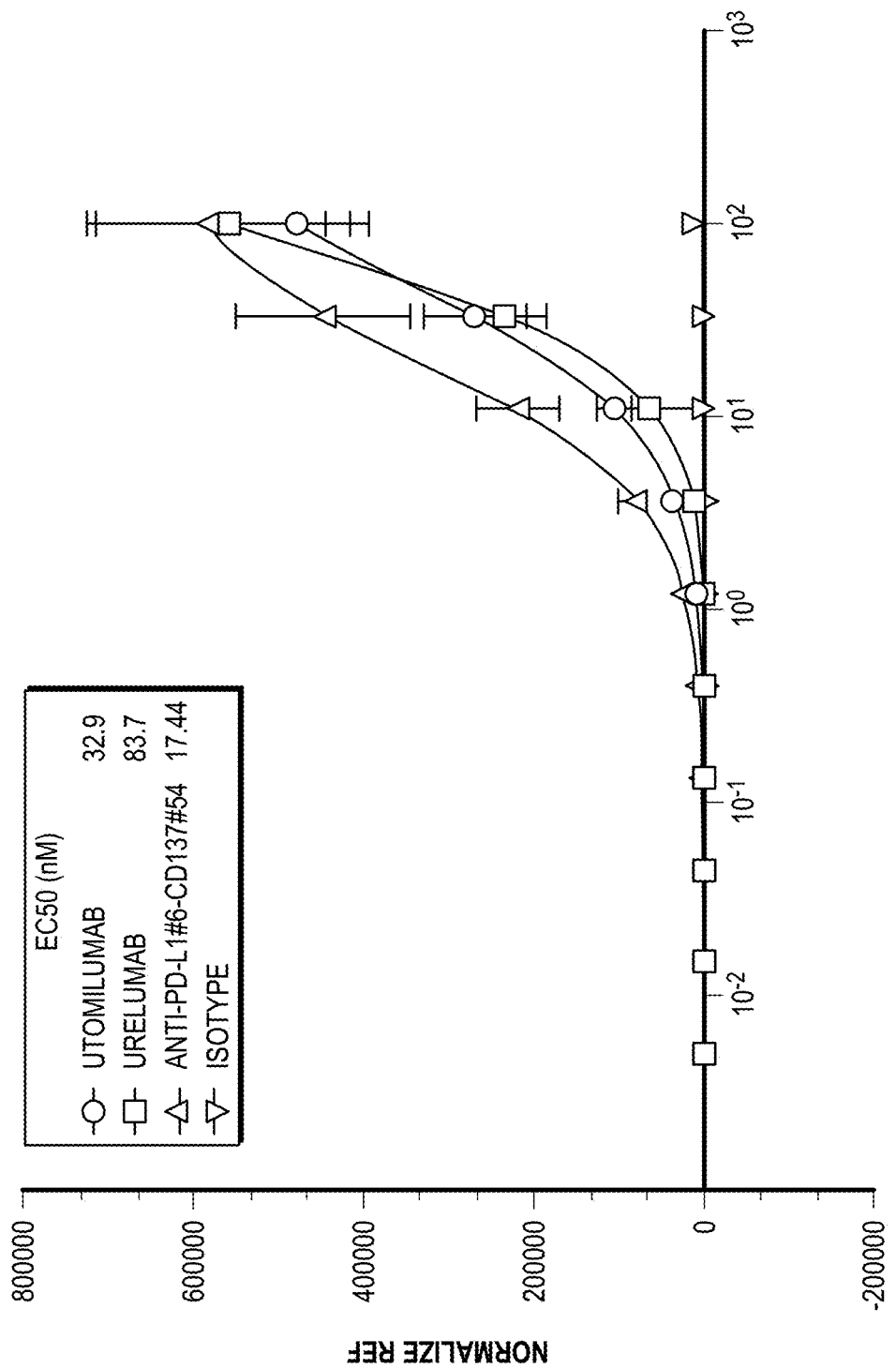
FIG. 23 shows that anti-PD-L1 #6-CD137 #54 bsAb induces internalization of CD137 expressed on HEK293 cells.

In one aspect, bispecific antibodies having a first antigen binding region that binds to CD137 and a second antigen binding region that binds to PD-L1 bind to CD137 and PD-L1 simultaneously (FIG. 16). Without being limited by theory, restricting anti-CD137 binding activity to tumor sites that express PD-L1 by designing bispecific antibodies that are able to bind to both CD137 and PD-L1 may reduce the risk of hepatotoxicity and its associated fatality seen in clinical trials with anti-CD137 antibodies such as Urelumab. In addition, it is believed that simultaneous binding to CD137 and PD-L1 may enhance T-cell activation as a result of cross-linking (see also Example 10 below). In another aspect, bispecific antibodies having a first antigen binding region that binds to CD137 and a second antigen binding region that binds to PD-L1 induce stronger CD137 internalization compared to reference antibodies such as Utomilumab and Urelumab (FIG. 23).

In some aspects, first antigen binding regions and second antigen binding regions include an scFv, an F(ab)2, an Fab, or any combination thereof. In one aspect, the first antigen binding region includes an scFv and the second antigen binding region includes an Fab. In another aspect, an scFv included in bispecific antibodies provided herein binds to an immune checkpoint molecule, an immune stimulatory molecule, or a tumor antigen. In yet another aspect, an scFv included in bispecific antibodies provided herein binds to a CD137. In some aspects, an Fab included in bispecific antibodies provided herein binds to an immune checkpoint molecule, an immune stimulatory molecule, or a tumor antigen. In one aspect, an Fab included in bispecific antibodies provided herein binds to PD-L1. In another aspect, the scFv of bispecific antibodies provided herein includes a $V_H$ region that includes an amino acid sequence of SEQ ID NO:9 and a $V_L$ region that includes an amino acid sequence of about 100 to 120 amino acids of an N-terminal sequence of SEQ ID NO:10. In yet another aspect, the scFv of bispecific antibodies provided herein includes a $V_H$ region that includes an amino acid sequence of SEQ ID NO:17 and a $V_L$ region that includes an amino acid sequence of about 100 to 120 amino acids of an N-terminal sequence of SEQ ID NO:18.

In one aspect, bispecific antibodies provided herein include a first antigen binding region that binds CD137 and a second antigen binding region that binds Her2. Bispecific antibodies that bind CD137 and Her2 include an scFv that binds CD137 fused to the C-terminus of the Fc domain of antibodies that bind to Her2, such as Trastuzumab (heavy chain SEQ ID NO:36) or anti-Her2 #3-7 (heavy chain SEQ ID NO:38). In certain aspects, bispecific antibodies that bind CD137 and Her2 further include a light chain of SEQ ID NO:35 (Trastuzumab) or SEQ ID NO:37 (anti-Her2 #3-7). In another aspect, bispecific antibodies provided herein include a first antigen binding region that binds CD137 and a second antigen binding region that binds a tumor-specific glycan. Bispecific antibodies that bind CD137 and a tumor-specific glycan include an scFv that binds CD137 fused to the C-terminus of the Fc domain of antibodies that bind to the tumor-specific glycan, such as anti-glycan provided herein (heavy chain SEQ ID NO:40). In certain aspects, bispecific antibodies that bind CD137 and a tumor-specific glycan further include a light chain of SEQ ID NO:39 (anti-glycan). In some aspects, bispecific antibodies that bind CD137 and Her2 or CD137 and a tumor-specific glycan further include a linker that links the anti-CD137 scFv to the Fc domain. Any linker can be used, such as GS linkers (SEQ ID NO:28), G4S linkers (SEQ ID NO:29), or multiples thereof. In one aspect, the linker is a G4S linker.

Figure 19:
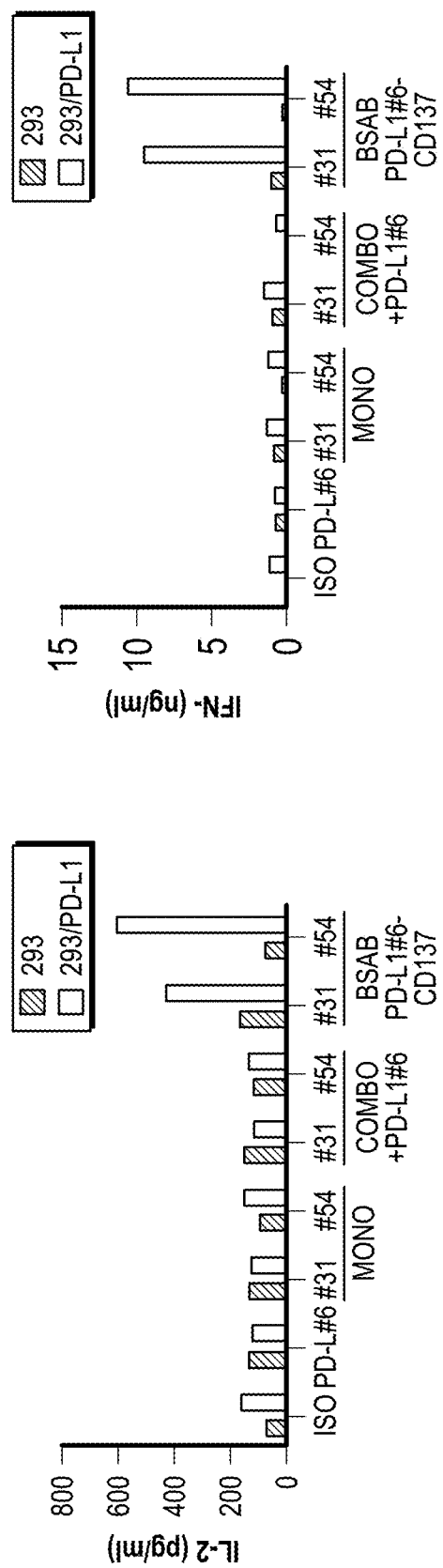
FIG. 19 shows that target-dependent T cell activation is induced by anti-PD-L1 #6-CD137 #31 or anti-PD-L1 #6-CD137 #54 bsAb while coculturing T cells with PD-L1-overexpressing HEK-293 cells.
Figure 20A:
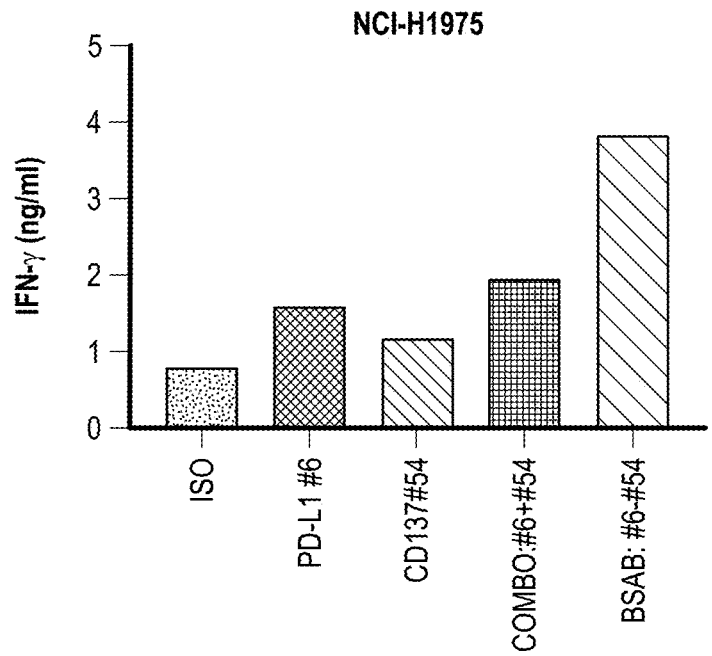
FIGS. 20A-20C show that anti-PD-L1 #6-CD137 #54 bsAb induces IFN-γ production (FIG. 20A, FIG. 20C and left panel of FIG. 20B) and cancer cell cytotoxicity (right panel of FIG. 20B) of T cells upon coculturing with PD-L1-positive cancer cells. (A) NCI-H1975, non-small cell lung cancer cells; (B) PC-3, prostate cancer cells; (C) MDA-MB-231, breast cancer cells.
Figure 20B:
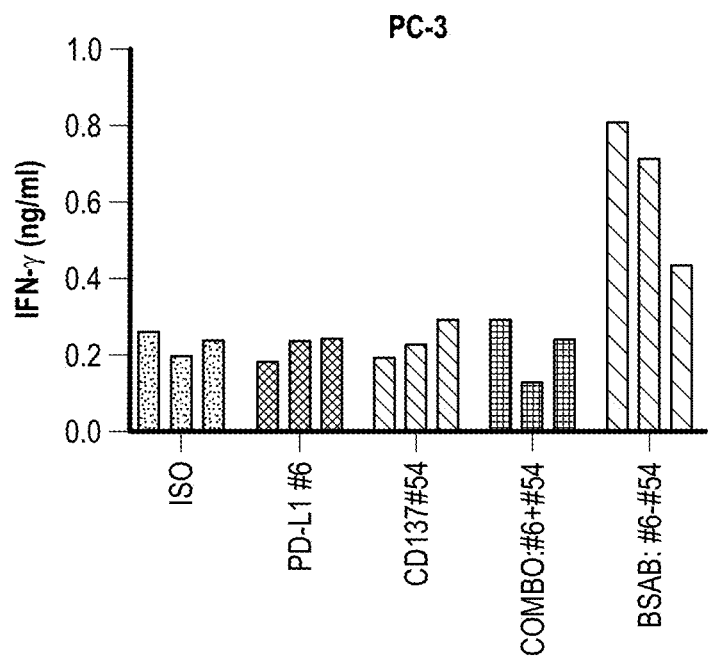
Figure 20B:
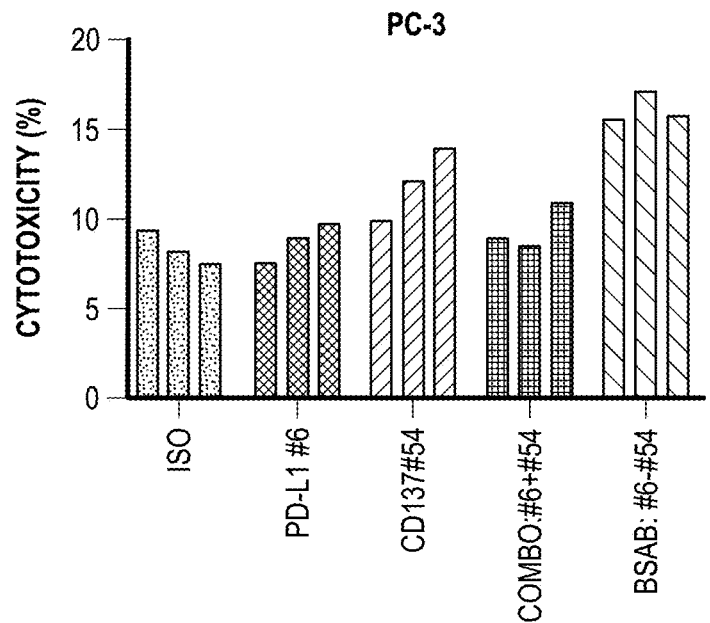
Figure 20C:
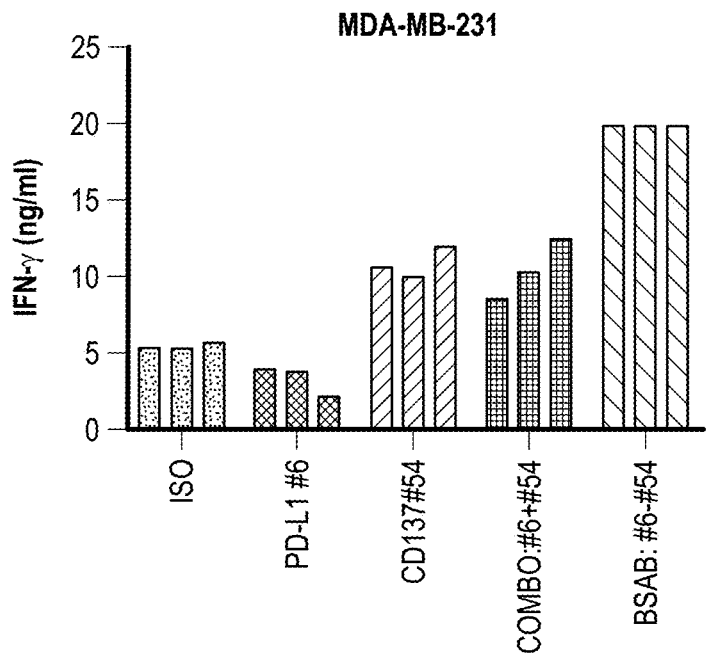
Figure 21A:
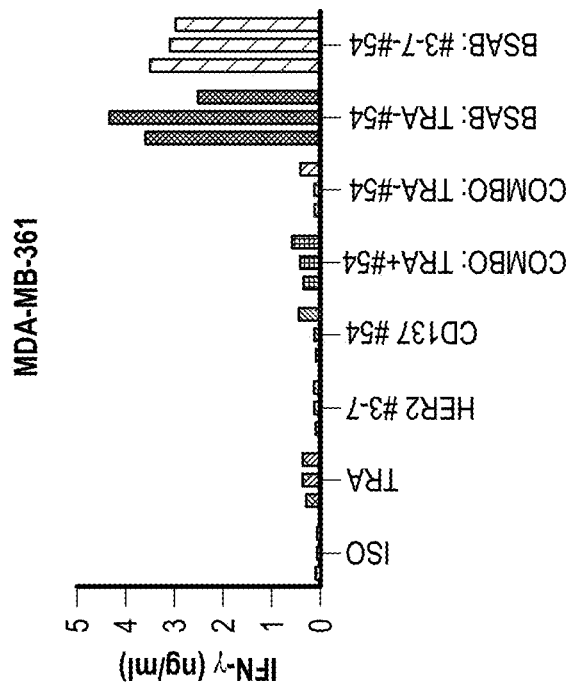
FIGS. 21A-21B show that Trastuzumab (Tra)-CD137 #54 or anti-Her2 #3-7-CD137 #54 bsAbs induce IFN-γ production of CD8 T cells upon coculturing with Her2-positive cancer cells. (A) SKBR-3, breast cancer cells; (B) MDA-MD-361, breast cancer cells.
Figure 21B:
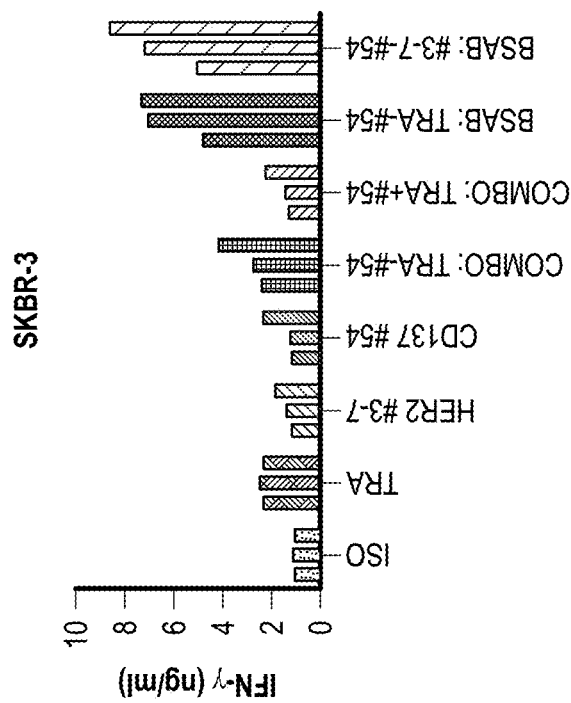
Figure 22A:
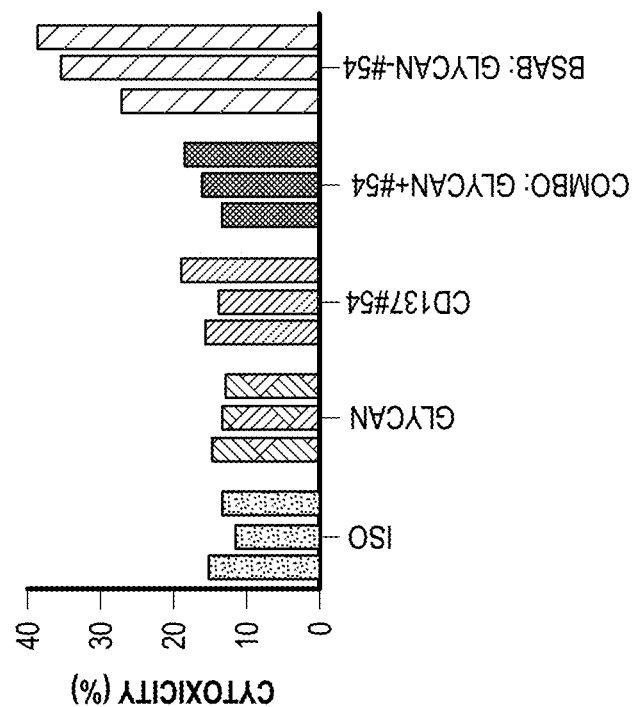
FIGS. 22A-22B show that anti-glycan-CD137 #54 bsAb induces IFN-γ production (left panel of FIG. 22A and FIG. 22B) and cancer cell cytotoxicity (right panel of FIG. 22A) of CD8 T cells upon coculturing with glycan-positive cancer cells. (A) MCF-7, breast cancer cells; (B) NCI-N87, gastric cancer cells.
Figure 22A:
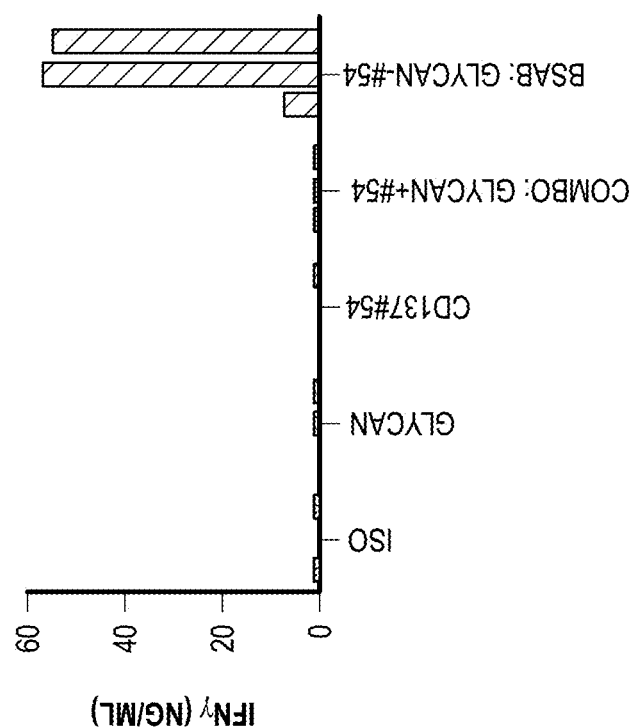
Figure 22B:
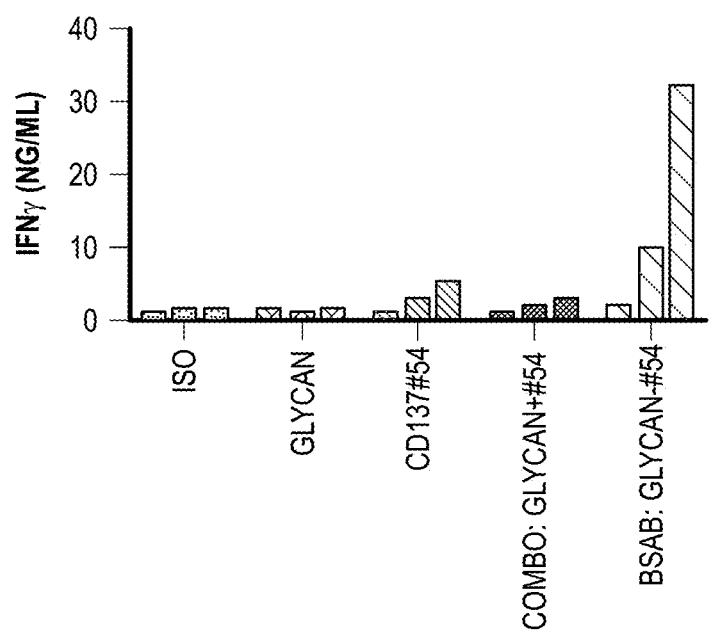

Accordingly, the present invention provides a platform of target-dependent T-cell activation. In one aspect, the agonist activity of an anti-CD137 scFv is induced upon binding to tumor-specific antigens such as PD-L1, for example, as shown in FIGS. 19 and 20. Anti-CD137 agonist activity can also be activated by binding to other tumor-specific antigens, such as Her2 and tumor-specific glycans, as shown in FIGS. 21 and 22.

In some aspects, bispecific antibodies provided herein further include a linker between the $V_H$ region and the $V_L$ region of the scFv. Any linker can be used. For example, linkers can include any amino acid sequence. Linkers can be of any length, such as one amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, 20 amino acids, or more amino acids. Linkers can also include multiples of an amino acid sequence. Any number of multiples of an amino acid sequence can be included in a linker. Exemplary linker sequences are provided in SEQ ID NO:28 and SEQ ID NO:29. In some aspects, the scFv includes an amino acid sequence of SEQ ID NO:33 or SEQ ID NO:34.

In some aspects, bispecific antibodies provided herein further include an Fc domain. In certain aspects, the Fc domain is an IgG domain, an IgE domain, an IgM domain, and IgD domain, an IgA domain, or an IgY domain. Fc domains of any sequence and from any species can be used, including human, ape, monkey, mouse, rabbit, goat, sheep, guinea pig, horse, and others. In some aspects, the IgG domain is an IgG domain, an IgG2 domain, an IgG3 domain, or an IgG4 domain. In one aspect, the IgG4 domain includes an amino acid sequence of SEQ ID NO:25. In another aspect, the IgG1 domain includes an amino acid sequence of SEQ ID NO:26. In one aspect, the Fc domain is human. Generally, human Fc domains are not immunogenic in humans and are therefore suitable for use in human therapeutics.

In some aspects, the scFv of bispecific antibodies provided herein is conjugated to the C-terminus of the Fc domain. In one aspect, a linker is included between the Fc domain and the scFv. In another aspect, a linker links the scFv to the Fc domain. Any linker can be used, such as G4S linkers provided herein.

In some aspects, the Fab of bispecific antibodies provided herein is linked to the N-terminus of the Fc domain. In one aspect, the Fab is linked directly to the N-terminus of the Fc domain via a peptide bond. In another aspect, the Fab domain is linked to the N-terminus of the Fc domain via a linker.

In some aspects, bispecific antibodies provided herein include a heavy chain sequence of SEQ ID NO:31 or SEQ ID NO:32. In another aspect, bispecific antibodies provided herein further include a light chain sequence of SEQ ID NO: 30. In one aspect, bispecific antibodies provided herein include a heavy chain sequence of SEQ ID NO:36. In another aspect, bispecific antibodies provided herein further include a light chain sequence of SEQ ID NO:35. In one aspect, bispecific antibodies provided herein include a heavy chain sequence of SEQ ID NO:38. In another aspect, bispecific antibodies provided herein further include a light chain sequence of SEQ ID NO:37. In one aspect, bispecific antibodies provided herein include a heavy chain sequence of SEQ ID NO:40. In another aspect, bispecific antibodies provided herein further include a light chain sequence of SEQ ID NO:39. Heavy chain sequences such as SEQ ID NO:31, SEQ ID NO:32, SEQ ID NO:36, SEQ ID NO:38, SEQ ID NO:40, and others, can include one or more G linkers (SEQ ID NO:28), one or more G4S linkers (SEQ ID NO:29), or any multiple of a G linker or G4S linker, although any other suitable linker can be used.

In some embodiments, provided herein are isolated amino acid sequences as set forth in SEQ ID NOs:30-40. Also provided herein, in some embodiments, are isolated nucleic acid sequences encoding any one of the amino sequences of SEQ ID NOs:30-40.

In some embodiments, provided herein are antibody-drug conjugates. Antibody-drug conjugates provided herein can include any antibody or antigen binding fragment thereof provided herein. For example, any antibody or antigen binding fragment thereof that specifically binds to CD137 can be included in antibody-drug conjugates. Any bispecific antibody or antigen binding fragment thereof provided herein can also be included in antibody-drug conjugates. In some aspects, antibody-drug conjugates provided herein include a therapeutic agent. Any therapeutic agent can be included in antibody-drug conjugates provided herein, including small molecules. In some aspects, the therapeutic agent has cytotoxic activity. Any chemotherapeutic agent that has cytotoxic activity can be included in antibody-drug conjugates. Exemplary chemotherapeutic agents include, but are not limited to, actinomycin, all-trans retinoic acid, anti-estrogens, azacitidine, azathioprine, bleomycin, bortezomib, carboplatin, capecitabine, cisplatin, chlorambucil, cyclophosphamide, cytarabine, dacarbazine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitomycin C, mitoxantrone, oxaliplatin, paclitaxel, pemetrexed, taxol, taxotere, tamoxifen, teniposide, tioguanine, topotecan, valrubicin, vemurafenib, vinblastine, vincristine, and vindesine.

In some aspects, antibody-drug conjugates provided herein are used for the treatment of cancer. For example, an antibody included in an antibody-drug conjugate binds to an antigen on tumor cells, thereby targeting a small molecule with cytotoxic activity or other therapeutic agent included in the antibody-drug conjugate to tumor cells. Upon binding of the antibody-drug conjugate to tumor cells, the small molecule or other therapeutic agent is internalized and released in tumor cells.

In some aspects, the therapeutic agent included in antibody-drug molecules provided herein is covalently linked to an antibody or antigen binding fragment thereof provided herein or to a bispecific antibody or antigen binding fragment thereof provided herein. A linker can be used to covalently link the therapeutic agent to the antibody or antigen binding fragment thereof or to the bispecific antibody or antigen binding fragment thereof. Any suitable linker can be used to covalently link a therapeutic agent to an antibody or antigen binding fragment thereof provided herein or to a bispecific antibody or antigen binding fragment thereof provided herein. In some aspects, the linker included in antibody-drug conjugates provided herein is stable outside of target cells, including in the circulation, and cleaved inside target cells to release the therapeutic agent. A therapeutic agent with cytotoxic activity, for example, can induce target cell death upon release. Accordingly, in some aspects, a therapeutic agent is selectively targeted to tumor cells. Selective targeting of a therapeutic agent to tumor cells generally results in reduced cytotoxicity to non-tumor cells and increased tolerability, for example.

Provided herein, in some embodiments, are pharmaceutical compositions that include a bispecific antibody provided herein. Any bispecific antibody provided herein can be included in a pharmaceutical composition. In one aspect, bispecific antibodies included in pharmaceutical compositions provided herein bind to CD137, PD-L1, or both CD137 and PD-L1. Antibody-drug conjugates provided herein can also be included in pharmaceutical compositions. In some aspects, pharmaceutical compositions are used for the treatment of cancer. Any cancer can be treated using a pharmaceutical composition provided herein. Exemplary cancers include prostate cancer, lung cancer, non-small cell lung cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, and leukemia.

In some embodiments, methods of treating cancer in a subject are provided herein. Methods of treating cancer include administering to a subject an amount of any bispecific antibody or an antigen binding fragment thereof provided herein, effective for treating the cancer. In some aspects, the cancer is prostate cancer, lung cancer, non-small cell lung cancer (NSCLC), melanoma, lymphoma, breast cancer, head and neck cancer, renal cell carcinoma (RCC), ovarian cancer, kidney cancer, urinary bladder cancer, uterine cancer, cervical cancer, ovarian cancer, liver cancer, stomach cancer, colon cancer, rectal cancer, oral cavity cancer, pharynx cancer, pancreatic cancer, thyroid cancer, skin cancer, brain cancer, bone cancer, hematopoietic cancer, or leukemia.

EXAMPLES

Example 1

This example illustrates antibody generation from an OmniMab library.

To generate therapeutic antibodies against CD137, selections with an OmniMab phagemid library were carried out. The phagemid library was built up by AP Biosciences Inc. (APBio Inc.) from a collection of peripheral blood mononuclear cells from over a hundred healthy donors. Pre-coated CD137-Fc recombinant protein was incubated with supernatant containing rescued phages for 1 hour and washed three with PBS containing 0.1% Tween-20. Bound phages were detected by HRP conjugated anti-M13 antibody (Roche) and TMB substrate was used for signal development. The OD450 readings were recorded.

Figure 2:
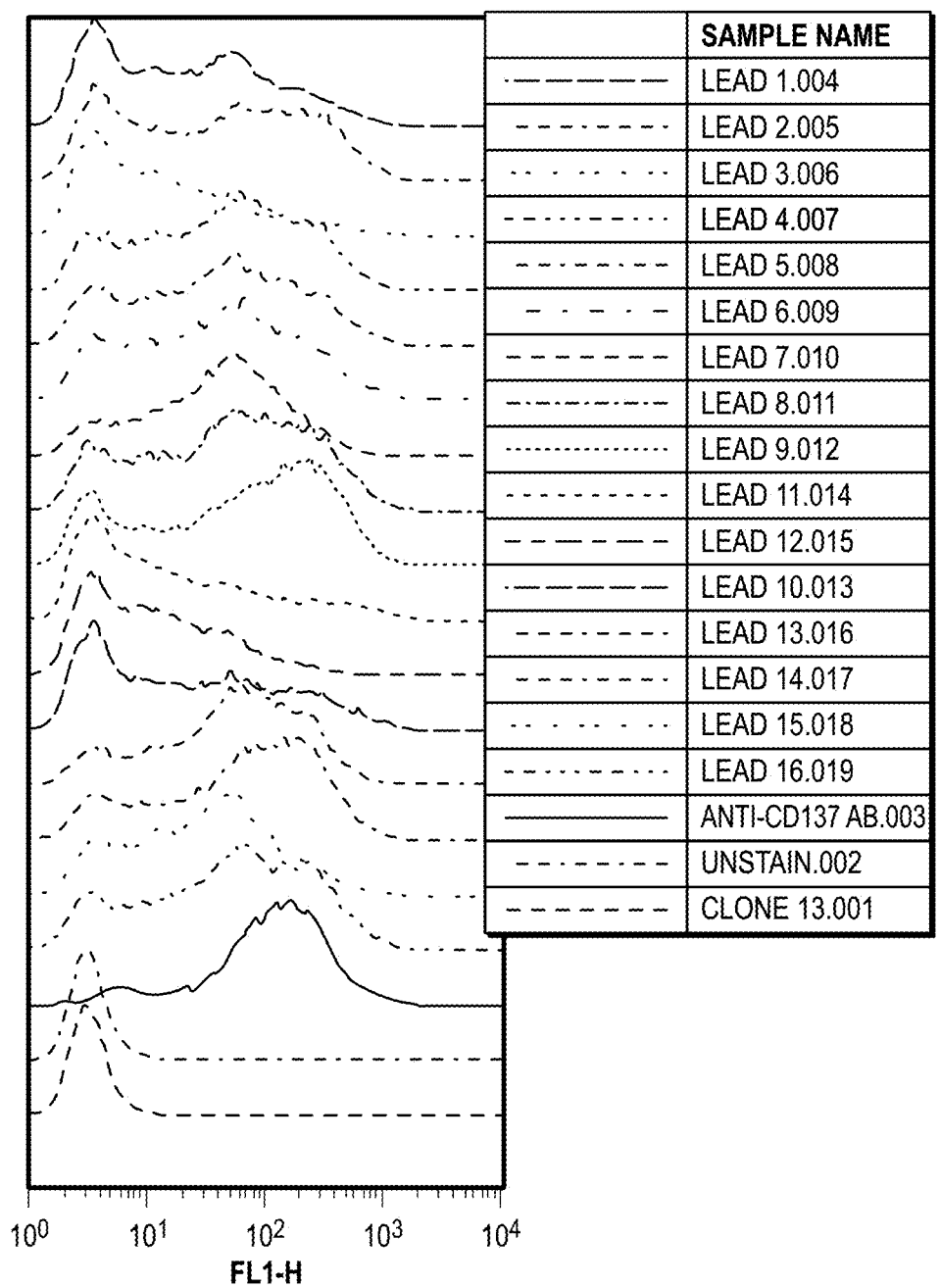
FIG. 2 shows the binding of phage clones targeted to CD137 on CD137-overexpressing HEK-293F cells by flow cytometry.
Figure 2:
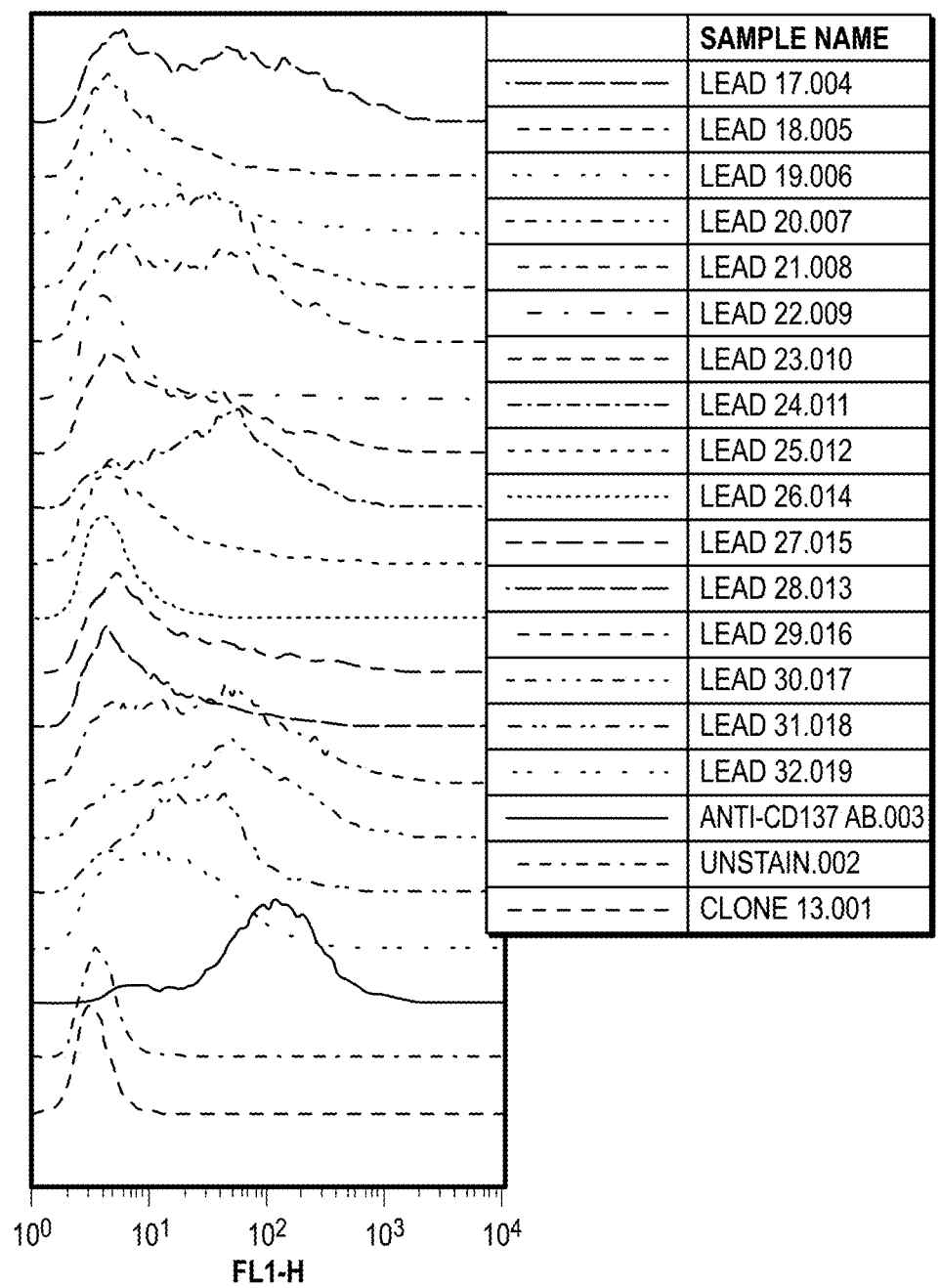
Figure 2:
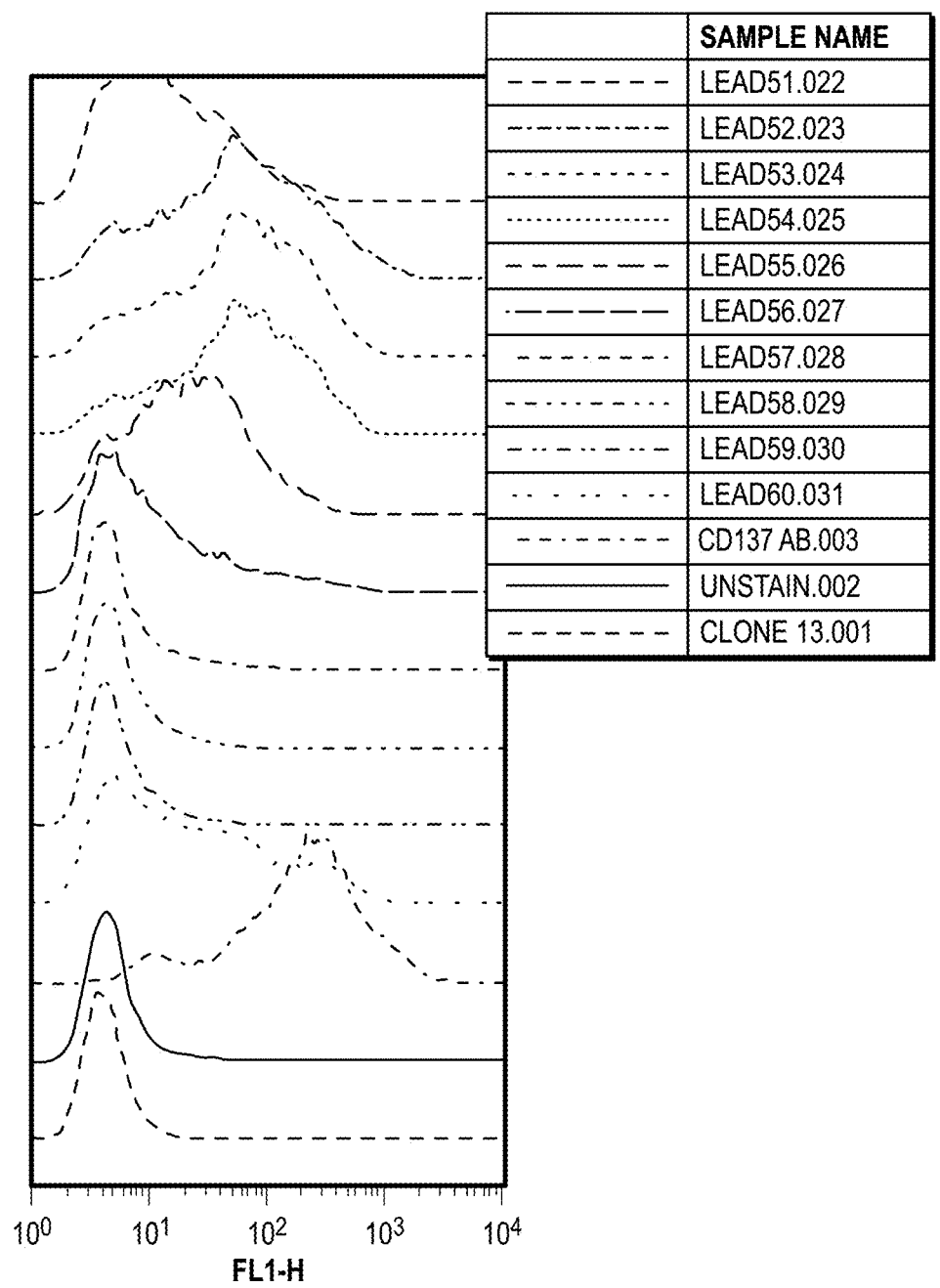

First round panning was performed using Hyperphage (M13K07ΔpIII, Progen, Heidelberg, Germany). Solid phase panning and cell panning against CD137 were used for CD137-specific binder selection and isolation from the OmniMab library. Solid phase panning was performed using recombinant human CD137-ECD-Fc (APBio Inc.) used in first-round selection. CD137-expressing HEK293 cells were used for second and third round enrichment. The specific CD137 binders were screened and isolated by direct ELISA and FACS after three rounds panning (FIG. 1 and FIG. 2). For FACS analysis, 293F cells stably expressing CD137 were stained with anti-CD137 phage supernatant (50 ul/well) to examine CD137 binding activity. 293F cells stably expressing CD137 were also incubated with 2.5 ug/ml anti-CD137 antibodies (Abs) as control on ice for 1 hr. The cells were washed three times with 1×PBS and then incubated with anti-M13 antibody (Progen) on ice for 1 hr. Cells were again washed three times with 1×PBS and then incubated with anti-mouse IgG-Alexa 488 (Invitrogen Inc.) on ice for an additional 1 hr. After staining, the cells were washed three times with 1×PBS, resuspended in 1×PBS before analysis by FACS Calibur (BD Biosciences, Inc.) and FlowJo (TreeStar, LLC). FACS analysis for 293F cells clone 13 stably expressing CD137 is shown in FIG. 2. Positive binders were isolated and sent for sequencing to confirm the sequence and diversity of the heavy chain. As shown in FIG. 1 and FIG. 2, several clones were isolated that specifically recognized CD137 antigen as compared with negative control.

These results show that phage clones obtained after three rounds of CD137-specific enrichment specifically recognize CD137.

Example 2

This example illustrates subcloning, expression, and purification of CD137-specific binding proteins in the form of IgGs.

To quickly screen for candidates with functionality in T cell activation, the heavy chains and light chains of positive CD137 or PD-L1 binders identified by ELISA were amplified, digested and subcloned into an IgG expression vector generated by APBio and carrying the IgG4 constant region (SEQ ID NO. 25). After sequence validation, plasmids were prepared and transfected into HEK293 cells for antibody expression using 293fectin transfection reagent (Invitrogen). After 4 days of culture, antibody secreted into serum-free medium was affinity purified from culture supernatant by Protein G chromatography. Purified antibody was concentrated, followed by dialysis in PBS buffer. The final concentration of dialyzed protein was determined using a Nano-Drop2000 spectrophotometer and the purity and integrity were determined by SDS-PAGE with or without reducing reagent.

Figure 3A:
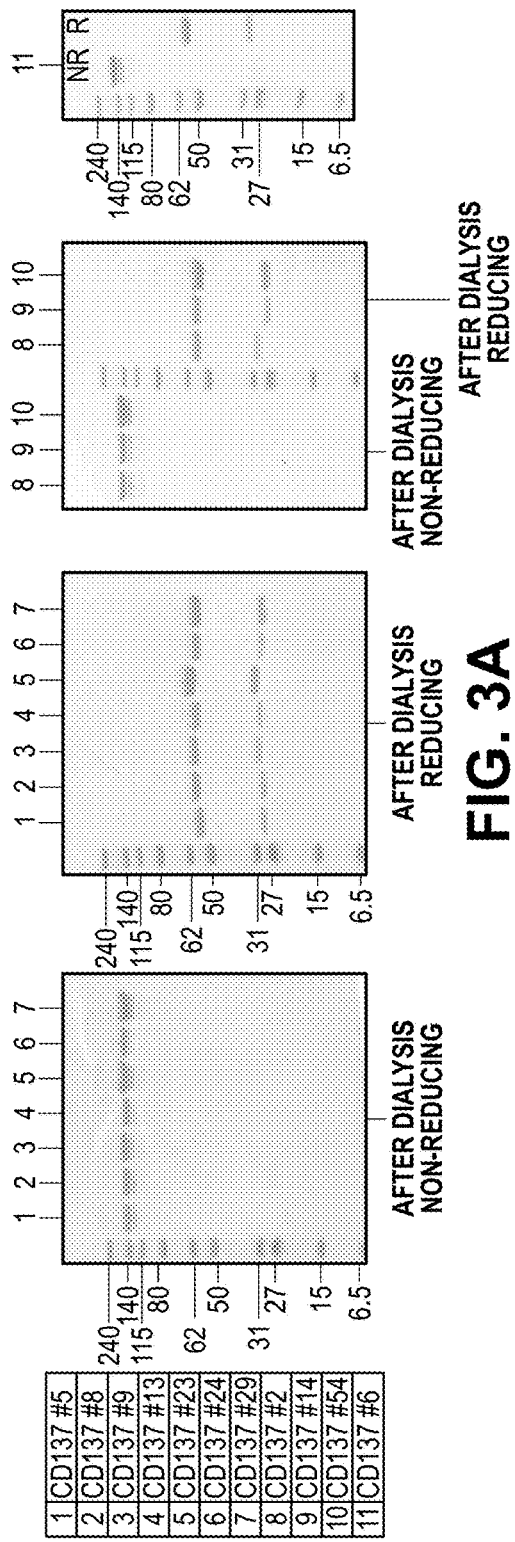
FIGS. 3A-3B show the integrity and purity of one-step Protein G-purified anti-CD137 antibody leads by PAGE. Results for two batches (top and bottom panels) are shown.
Figure 3B:
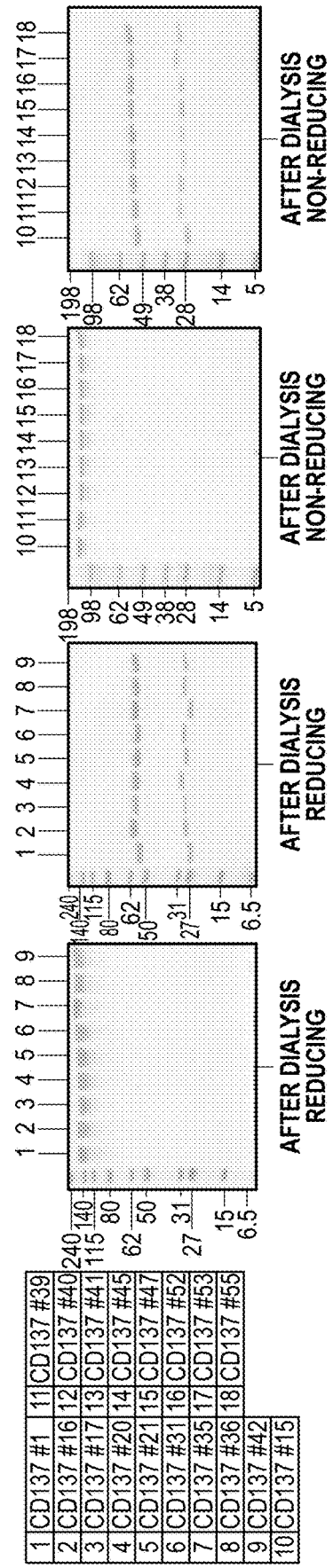

FIG. 3 shows representative PAGE gel analysis of a first batch (FIG. 3, top panels) and a second batch (FIG. 3, bottom panels) of purified anti-CD137 antibody leads. Culture supernatants from mammalian cells collected 4 days post-transfection were purified using Protein G chromatography (Thermo Fisher). The purified proteins were analyzed under reducing or non-reducing condition before loading on the gel (3 μg/lane). Results indicated that both proteins have a molecular weight of about 145 kDa under non-reducing conditions, and heavy chain and light chain have a molecular weight of ~55 kDa and ~25 kDa, respectively, under reducing conditions. More than 90% purity could be obtained by one step of Protein G chromatography.

These results show that the integrity of various purified antibody leads is normal in the HEK293 cells.

Example 3

This example illustrates binding of anti-CD137 antibody to Jurkat cells.

Figure 4:
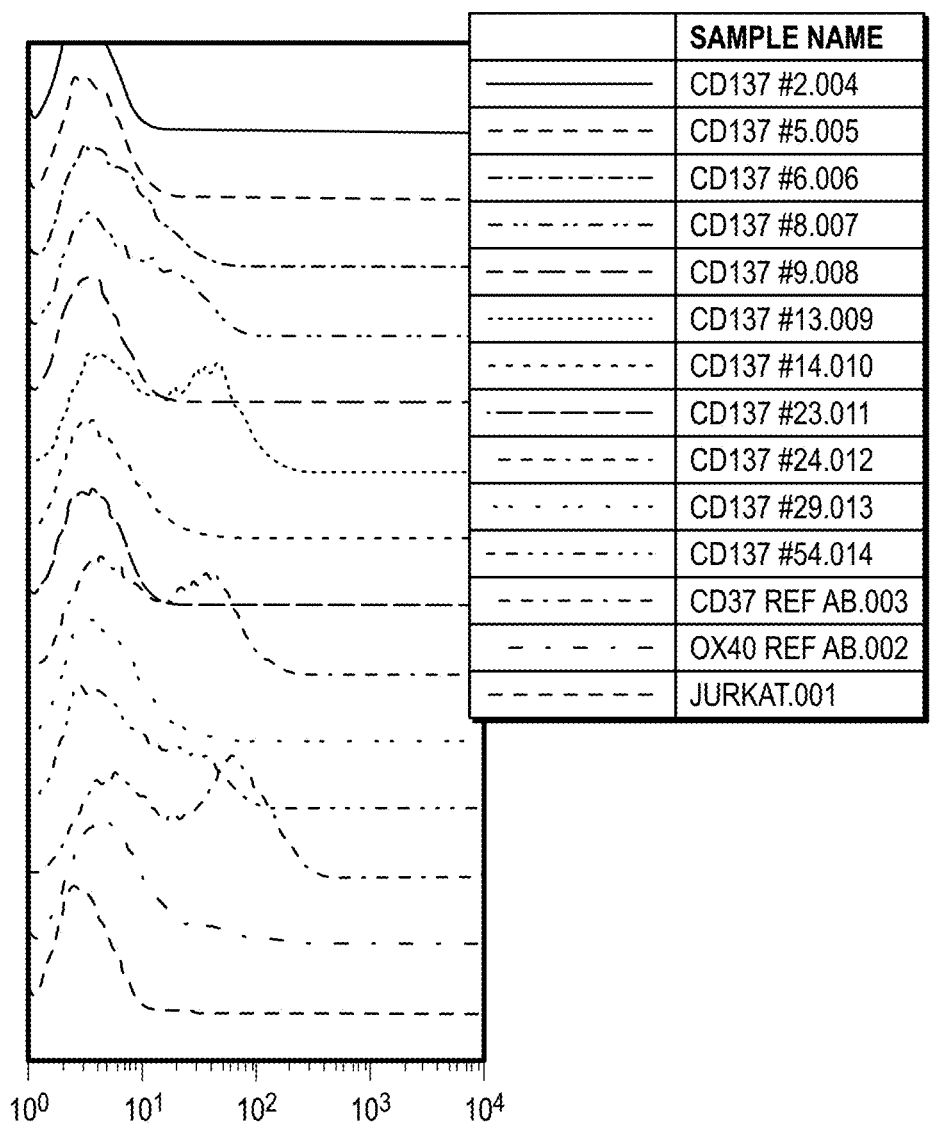
FIG. 4 shows the binding of anti-CD137 antibody leads on activated Jurkat cells by flow cytometry.

Purified anti-CD137 antibody leads were also applied to CD137-induced Jurkat cells to determine binding activity by FACS. Jurkat cells were treated with PMA (10 ng/ml) and ionomycin (1 μg/ml) to induce CD137 expression for 2 days. Stimulated cells were incubated with anti-CD137 (0.5 μg/ml) and reference (ref) Ab (0.5 μg/ml) as positive control for 1 hr on ice, left unstained or incubated with OX40 reference (ref) Ab as negative controls. The cells were washed three times with 1×PBS and then incubated with Alexa-488-conjugated goat anti-human IgG (H+L) (Invitrogen Inc.) on ice for an additional 1 hr. After staining, the cells were washed three times with 1×PBS, resuspended in 1×PBS before being analyzed by FACS Calibur (BD Biosciences, Inc.) and FlowJo (TreeStar, LLC). Among CD137 antibody leads, several leads possessed binding activity comparable to the reference antibody, as shown in FIG. 4.

These results show binding of anti-CD137 antibody leads to activation of Jurkat cells, as seen by flow cytometry.

Example 4

This example illustrates determination of anti-CD137 antibody binding activity by ELISA.

To perform a direct ligand binding assay of anti-CD137 antibody binding to CD137, recombinant CD137/Fc (100 ng/ml) was used to prepare pre-coated wells. Briefly, purified human CD137-IgG4 Fc (APBio) was dialyzed in Phosphate Buffered Saline (PBS), adjusted to 1 mg/ml and then diluted with PBS to a final concentration of 1 g/ml. Nunc-Immuno Maxisorp 96 well plates were pre-coated with 0.1 ml per well of recombinant CD137 protein, leaving empty wells for nonspecific binding controls, and incubated at 4° C. overnight. The CD137 recombinant protein solution was removed and the plates were washed three times with 0.4 ml of wash buffer (0.1% Tween-20 in PBS). 0.4 ml blocking buffer (5% low-fat milk powder in PBS) was added to all wells and incubated at room temperature for 1 hour. The blocking buffer was removed and washed three times with 0.4 ml wash buffer.

Figure 5:
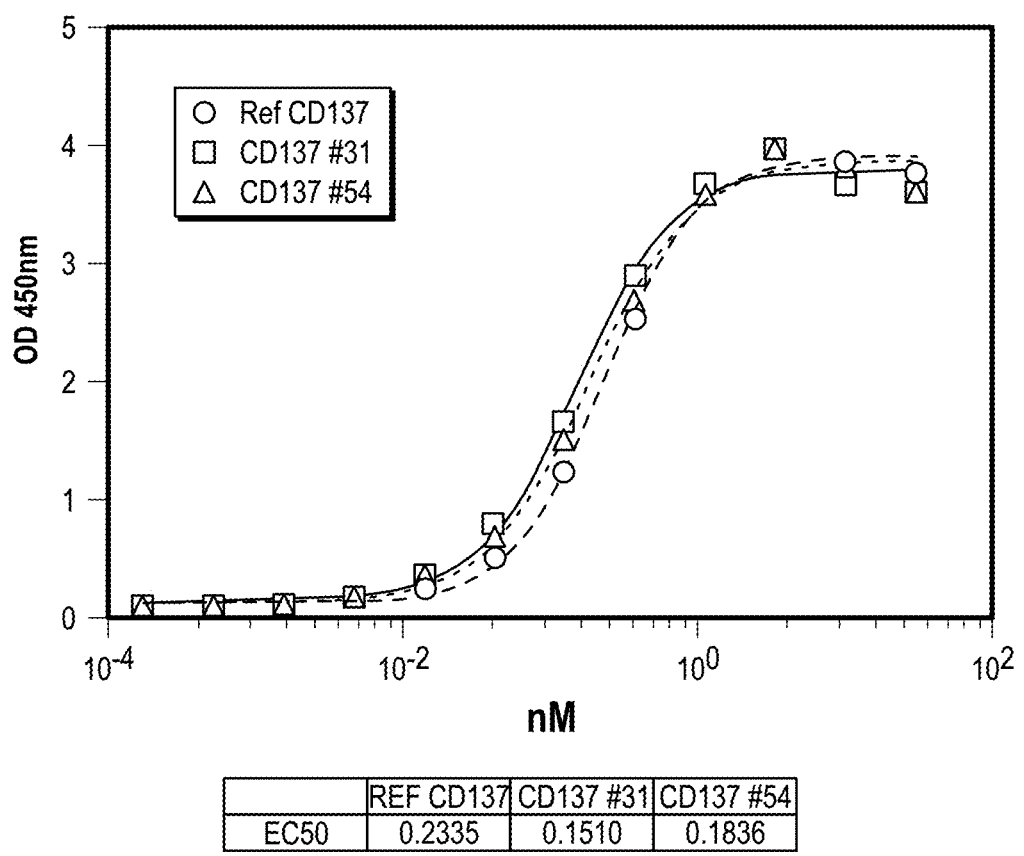
FIG. 5 shows the binding activity ($EC_{50}$) of anti-CD137 antibody leads to recombinant human CD137 by ELISA.

Pre-coated wells were incubated with serial dilutions of purified anti-CD137 antibodies. Serial dilutions of the CD137 antibodies were prepared in PBS and 0.1 ml added into each well. Plates were incubated for 1 hour at room temperature. The antibody solution was removed and the plates were washed three times with 0.4 ml wash buffer. HRP-conjugated goat anti-human IgG, F(ab')2 specific F(ab')2 antibody (Jackson Immunoresearch #109-036-097) was diluted 1:2000 with PBS and added at 0.1 ml per well. The plates were incubated for 1 hour at room temperature and washed three times with 0.4 ml wash buffer per well. Plates were developed with 0.1 ml TMB reagent (Invitrogen) and incubated for 1 to 5 minutes at room temperature. 0.05 ml 1N HCl was added to stop the reaction and absorbances were read at 450 nm on a Bio-Tek Spectra. OD450 readings were plotted against anti-CD137 concentrations, and 50% effective concentration ($EC_{50}$) values of anti-CD137 antibody binding to CD137/Fc were calculated. $EC_{50}$ values were calculated using GraphPad Prism (GraphPad Software, San Diego, Calif.). Calculated $EC_{50}$ values for anti-CD137 antibody clone 31 and clone 54 showed comparable binding activity to the reference antibody. Calculated $EC_{50}$ values for anti-CD137 specific antibody leads showed good binding activity compared to reference antibody (FIG. 5).

Anti-PD-L1 antibodies were detected with HRP-conjugated anti-human IgG1 Fab antibody before color development, with OD450 reading plotted against anti-PD-L1 concentrations.

Example 5

This example illustrates evaluation of protein aggregation of highly concentrated anti-CD137 antibody leads by SEC-HPLC.

Figure 6:
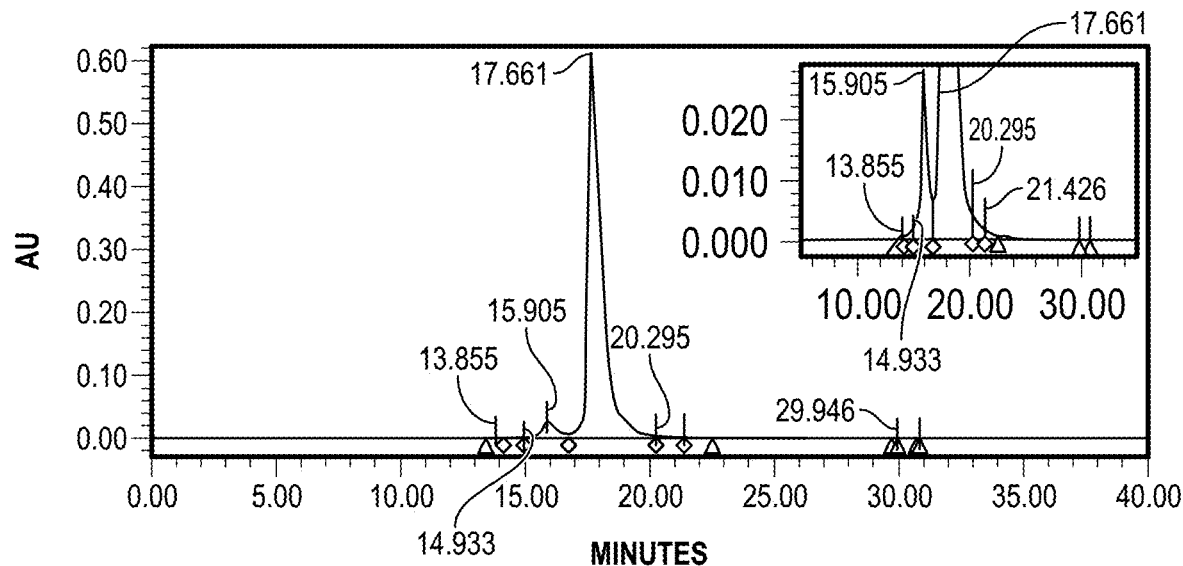
FIG. 6 shows protein aggregation of highly-concentrated anti-CD137 antibody clone 31 and clone 54 by SEC-HPLC.
Figure 6:
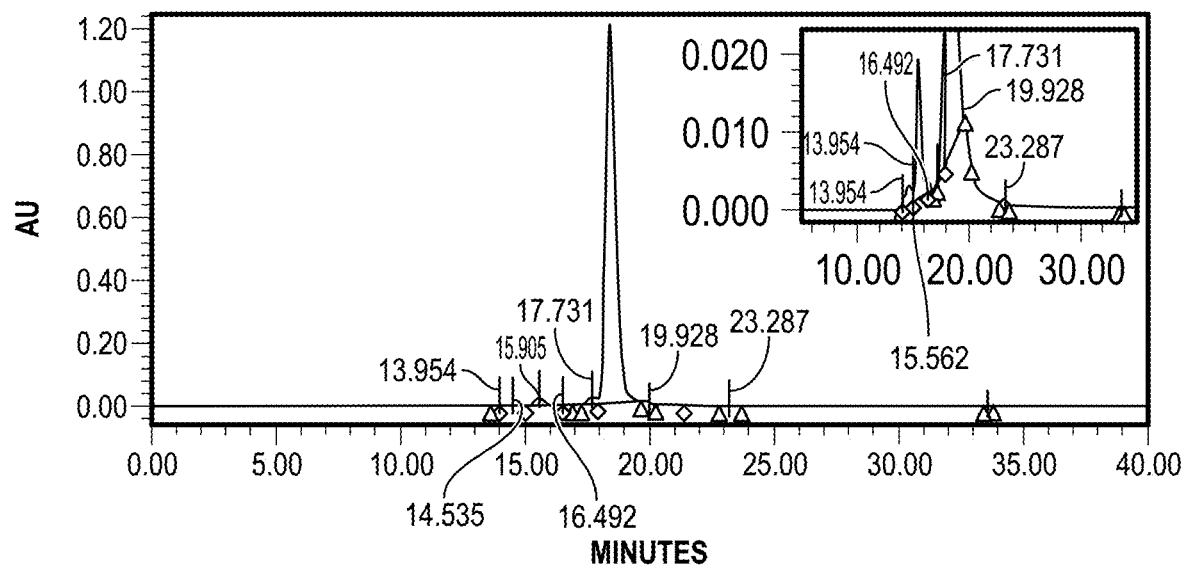

SEC-HPLC was performed using a Waters Alliance Separation Module 2695 with a Waters 2996 Photodiode Array detector. Samples were loaded onto a XBridge Protein BEH SEC Column (Waters, Cat #176007640) with isocratic 25 mM sodium phosphate, 200 mM NaCl, pH 6.8 as mobile phase buffer for SEC separation. The flow rate was 0.4 mL/min and the sample injection volume was 10 μL. Peaks were detected by absorbance at 280 nm. Before injection onto the SEC column, all samples were filtered with a 0.22 μm filter (Millipore, Cat #SLGP003RB) to remove any precipitated protein material. Data were analyzed by Empower 2 software. The main peak percentages of the highly concentrated-anti-CD137 antibody clone 31 and clone 54 were greater than 90%, as shown in the FIG. 6, with no obvious protein aggregates.

These results show that a high concentration anti-CD137 antibodies does not result in the formation of aggregates.

Example 6

This example illustrates agonistic activity of anti-CD137 antibodies.

Figure 7:
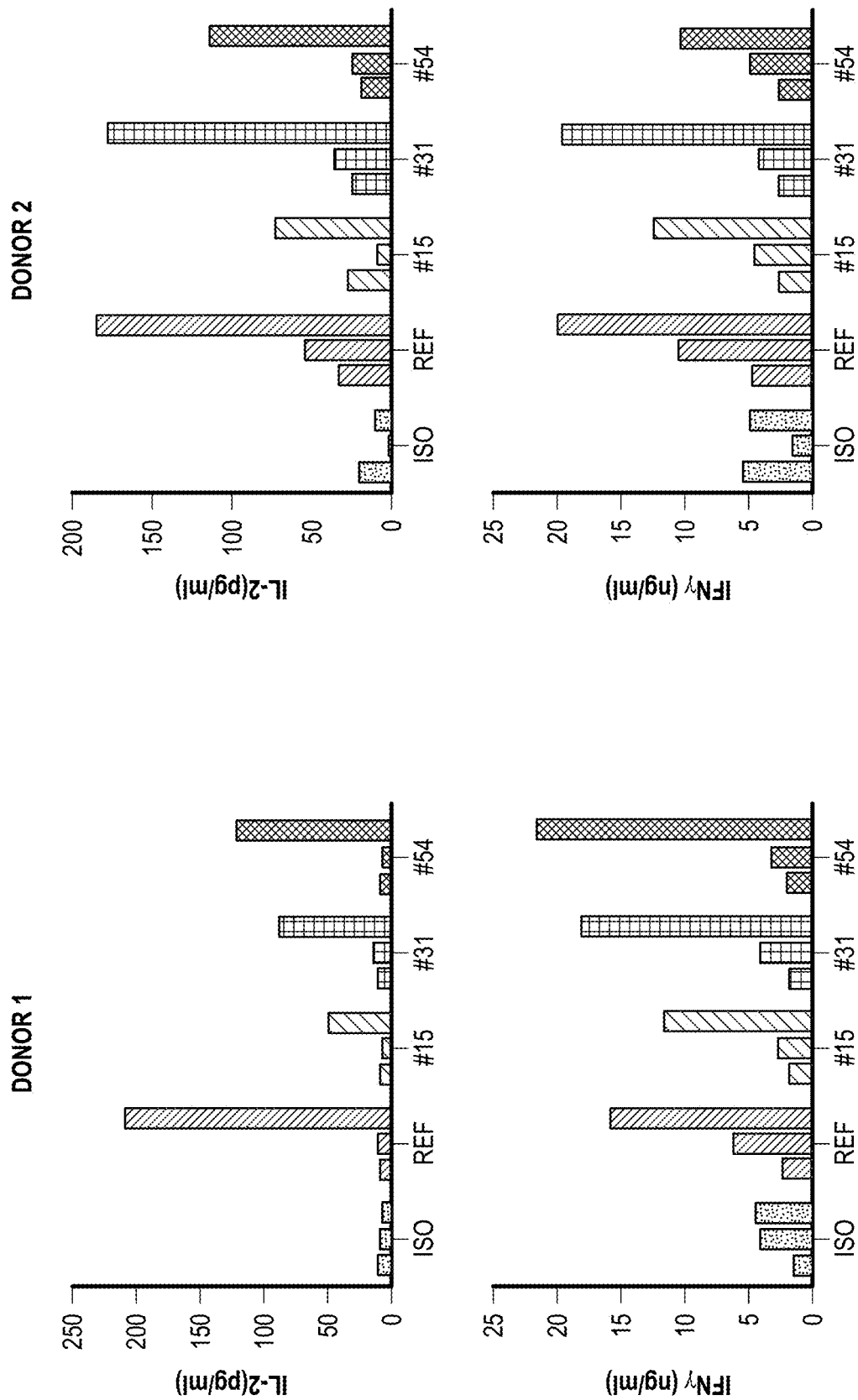
FIG. 7 shows cytokine production of T cells in the presence of the agonistic activity of anti-CD137 antibody leads.
Figure 7:
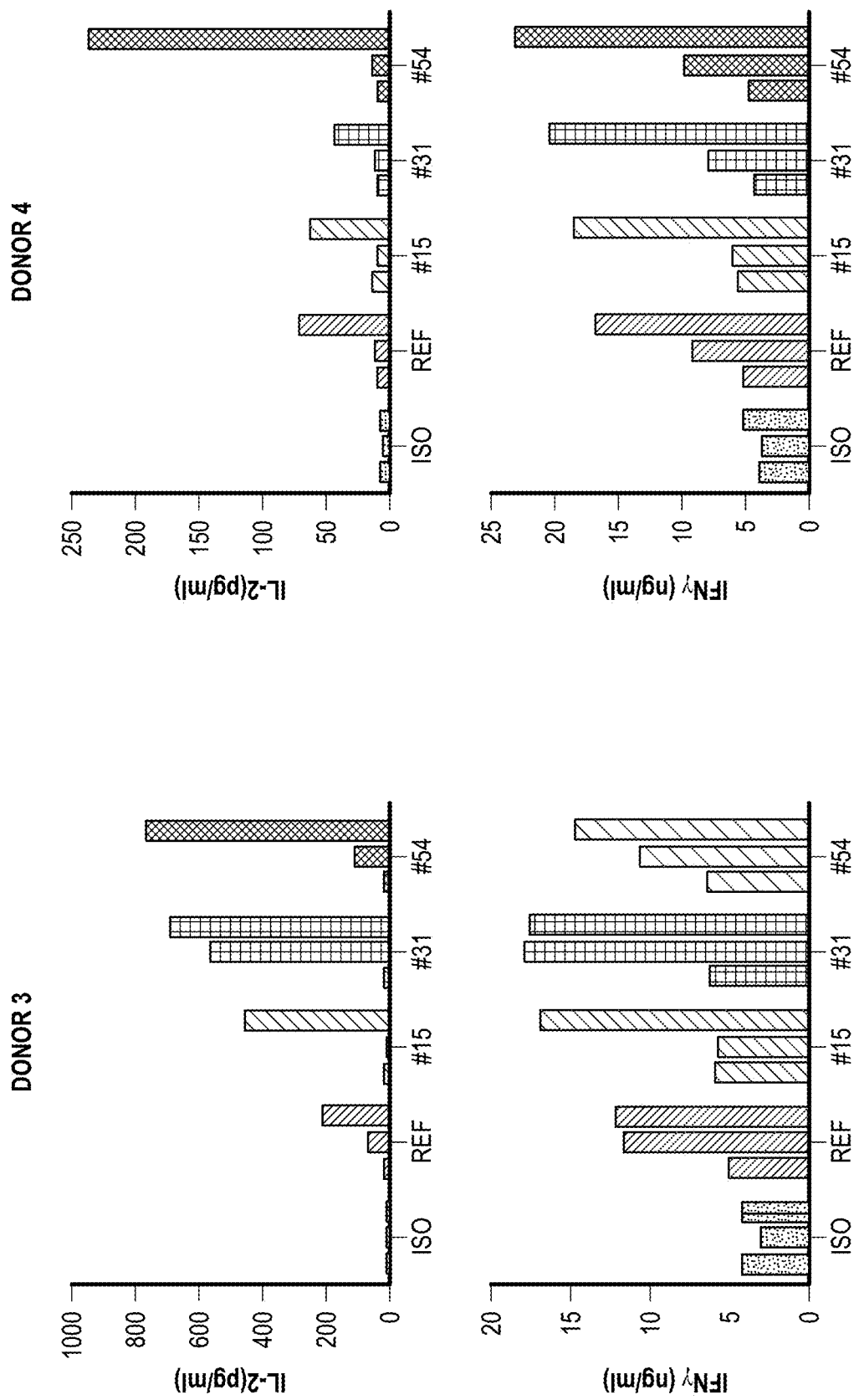
Figure 8:
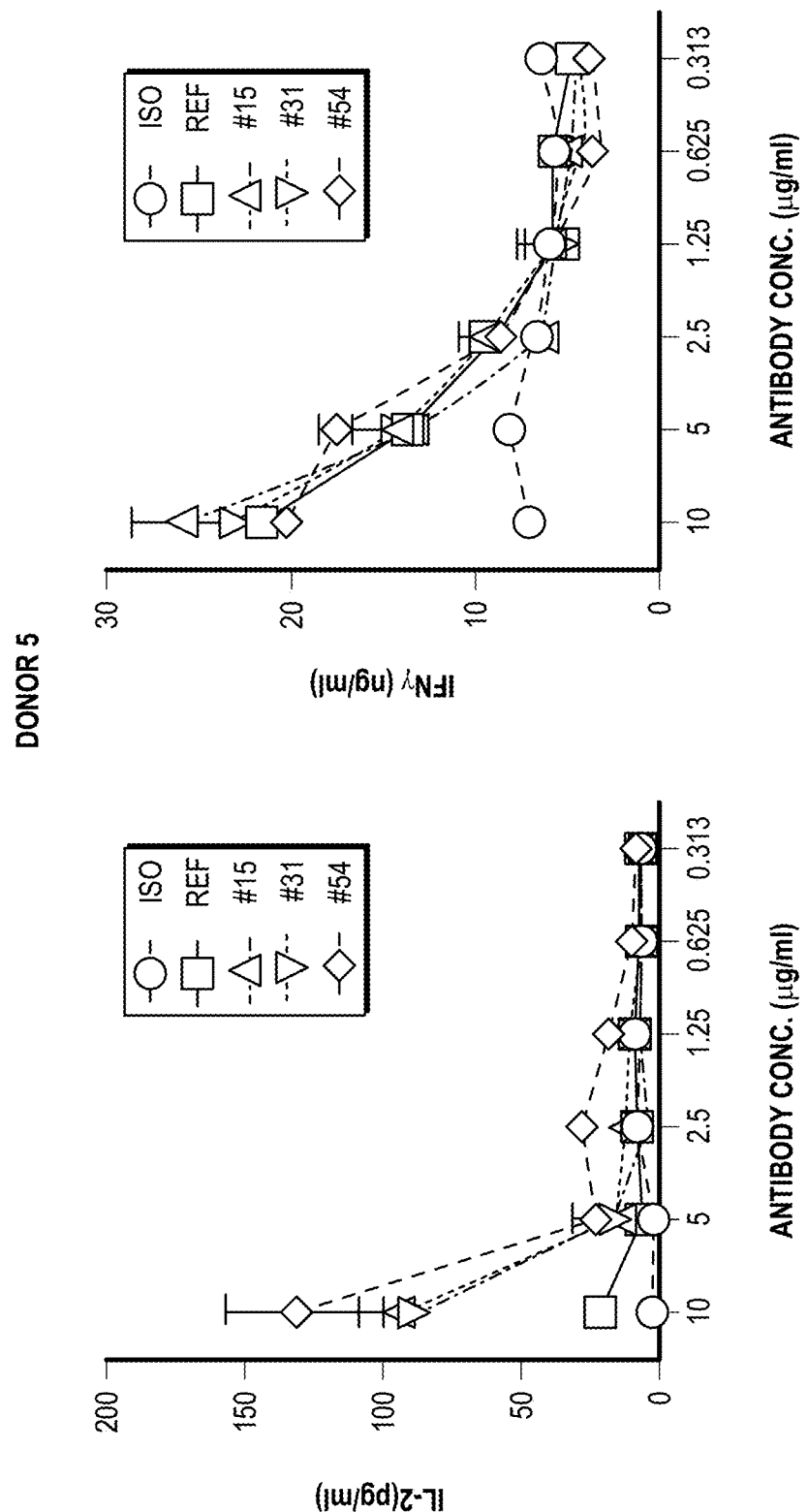
FIG. 8 shows dose-dependent induction of human T cell cytokine production by anti-CD137 antibody lead clones in primary human T cells.
Figure 8:
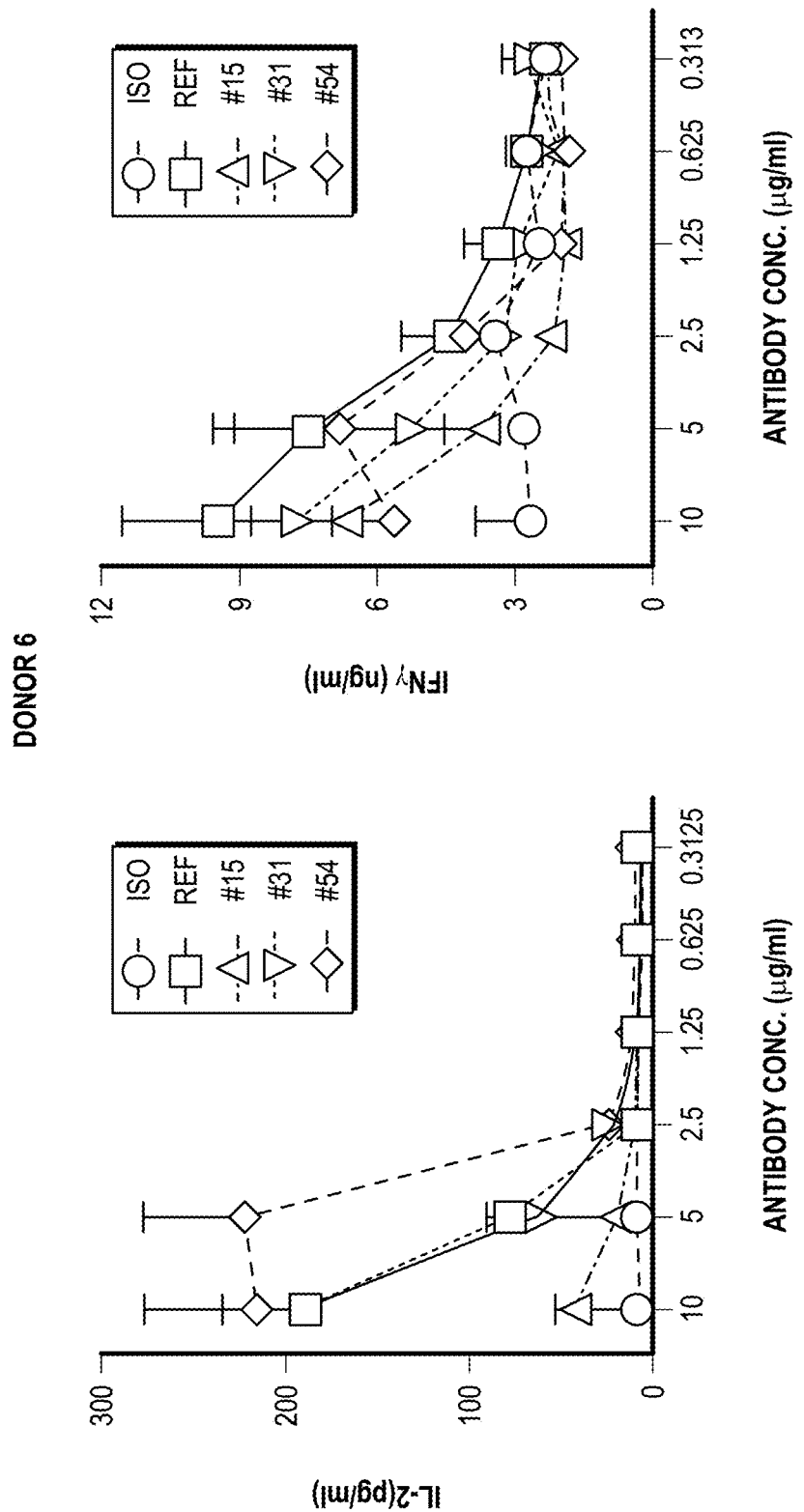

Purified antibody leads were functionally screened for their ability to enhance activation of human CD3+ cells, as seen by enhanced cytokine production, proliferation, and induction of proliferation of human CD3+ T cells. Anti-CD3 antibody (1 ug/ml, OKT3, BioLegend Cat. No. 317304), anti-CD137 antibody leads or isotype antibody (1, 3, and 10 ug/ml) were coated on a Maxisorp 96-well plate. Human CD3+ T-cells were isolated from peripheral blood of heathy adult volunteers using the RosetteSep™ Human T Cell Enrichment Cocktail (STEMCELL Cat. No. 15061). Isolated CD3+ T cells were labeled with CFSE (CellTrace™ CFSE cell proliferation kit, Life Technologies, Cat. No. C34554) and seeded in pre-coated wells (1×10^5 cells per well) with RPMI1640 medium (containing 10% fetal bovine serum, 2.5 mM L-glutamine, 1× Penicillin/Streptomycin). Three days later, cell proliferation was analyzed by flow cytometry and cytokine production of IL-2 and INF-γ were analyzed by ELISA. As shown in FIG. 7 and FIG. 8, anti-CD137 antibody leads #15, #31, and #54, showed agonistic activity to enhance the CD3+ T cell activation in a dosage- and donor-dependent manner for at least two of four donors tested. Anti-CD137 clones #31 and #54 showed comparable or higher agonistic activity as seen by enhanced T cell activation as compared to reference antibody (Utomilumab; Chin et al., 2018; antibody sequence at kegg.jp/dbget-bin/www_bget?dr:D10997; see also U.S. Pat. No. 8,337,850). Therefore, clones #31 and #54 were chosen for bispecific antibody construction, as described below.

Example 7

This example illustrates combination treatment with anti-PD-L1 and anti-CD137 antibody in a mixed lymphocyte reaction.

Figure 9:
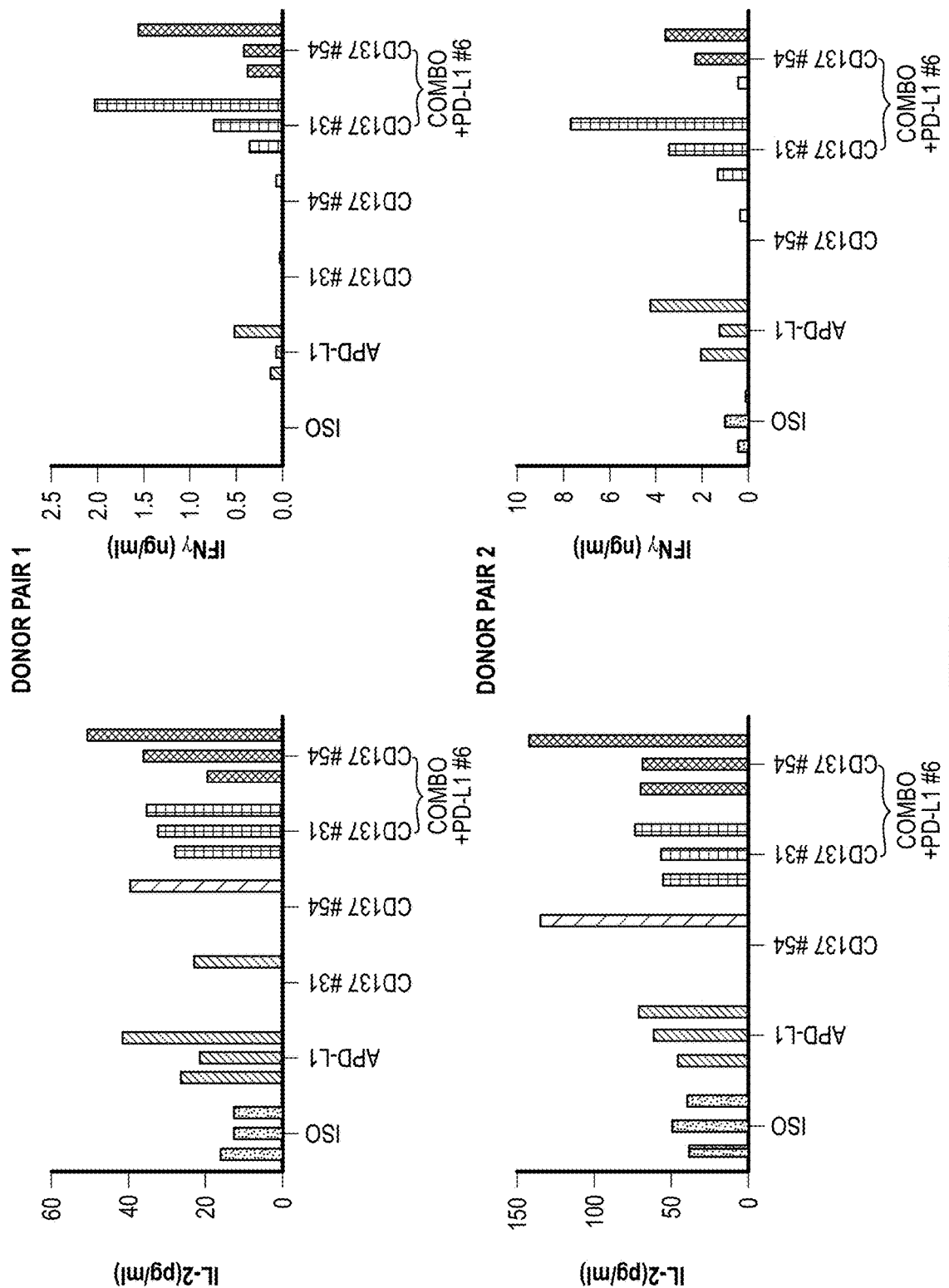
FIG. 9 shows that the combined treatment with anti-CD137 antibody boosts anti-PD-L1 antibody-mediated IFN-γ production by T cells in the mixed lymphocyte reaction.

Monocytes were isolated from peripheral blood of healthy donors by RosetteSep™ Human Monocyte Enrichment Cocktail (Cat. No. 15068) and cultured in RPMI1640 differentiation medium containing human GM-CSF and IL-4 (1000 U/ml each, R&D) for 6 days. Dendritic cell (DC) differentiation was verified by expression of DC-SIGN, CD14, CD80 or CD83 using flow cytometry. Differentiated DC were used as antigen-presenting cells (APCs) in mixed lymphocyte reactions (MLRs). Allogenic CD4+ T cells were isolated from human peripheral blood using RosetteSep™ Human CD4+ T Cell Enrichment Cocktail (Cat. No. 15062). The purity of CD4+ T cells was about 95% based on CD3 and CD4 expression. CFSE-labeled CD4+ T cells were co-cultured with DCs in the presence of antibody leads (0.4, 2, and 10 μg/ml) for 3 and 5 days. CD4+ T cell proliferation was analyzed by flow cytometry and cytokine production of IL-2 and IFN-γ in the culture medium was detected by ELISA. IL-2 and INF-γ production increased significantly in the presence of anti-PD-L1 antibody in MLRs as compared to isotype control antibody. Interestingly, anti-CD137 antibody, such as clone #31, for example, further boosted anti-PD-L1 antibody-mediated IFN-γ production in MLRs with two distinct donor pairs, as shown in FIG. 9.

Example 8

This example illustrates the effects of anti-CD137 antibodies on CD137-CD137L interaction.

Figure 10:
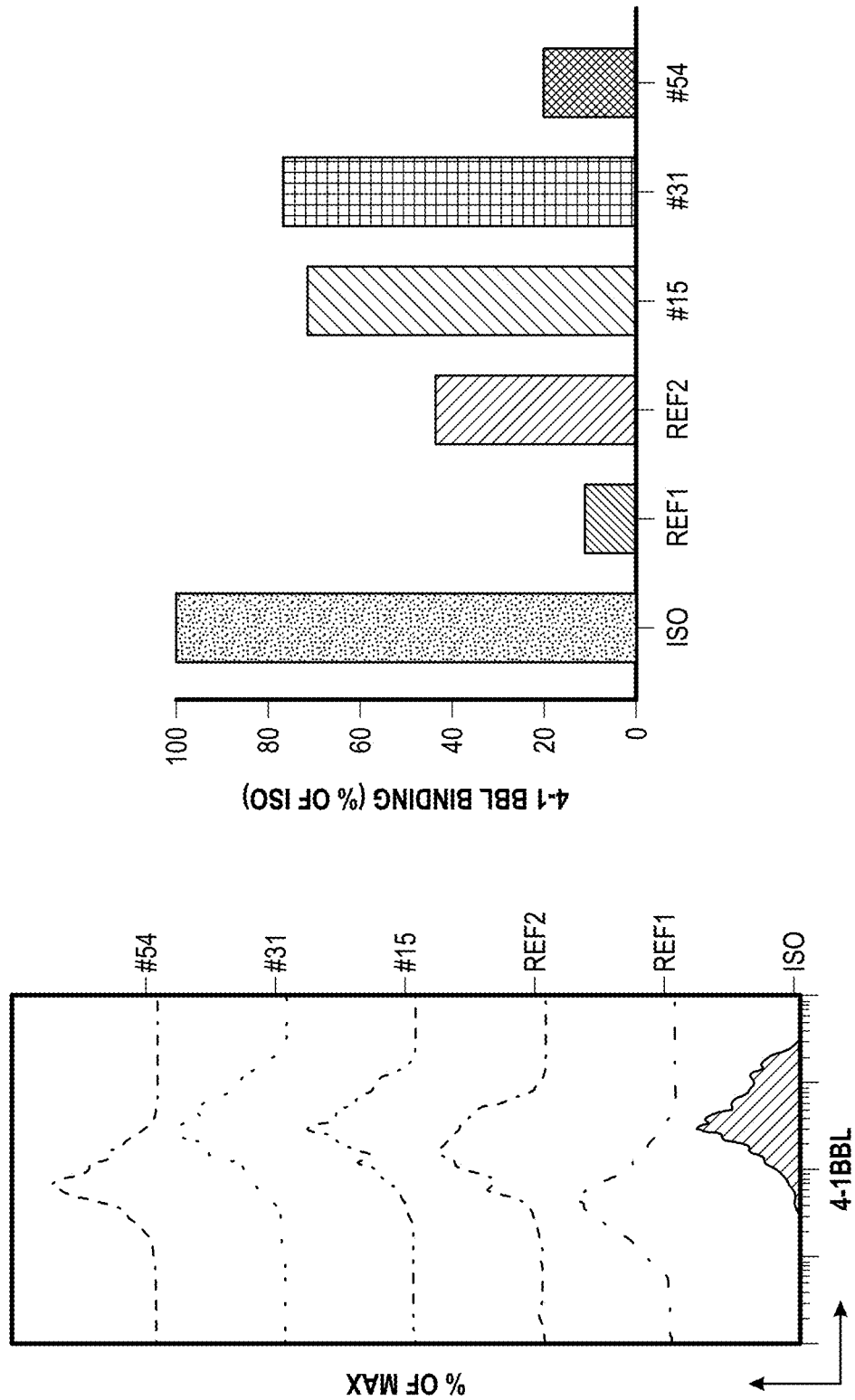
FIG. 10 shows distinct effects of anti-CD137 antibody clones on CD137-CD137L interaction.

HEK-293F/CD137 cells were incubated with isotype control and anti-CD137 antibodies (50 μg/ml) for 30 mins on ice, washed twice with PBS/2% FBS (PBS2), and incubated with His-tagged 4-1BBL (0.5 μg/ml, Acro BIOSYSTEMS) for 20 mins on ice. After washing twice with PBS2, the presence of anti-CD137 antibody and 4-1BBL on HEK-293F/CD137 cells was detected using anti-human Fc-A488 (Jackson ImmunoResearch) and anti-His antibody-APC (Biolegend), respectively, followed by analysis using a Calibur flow cytometer (BD). Except for incubation with isotype control, almost all cells were A488-positive. Mean fluorescence intensity (MFI) of the APC channel was calculated using FlowJo (TreeStar, LLC) and values shown as a histogram (FIG. 10). As shown in FIG. 10, the reference antibody 1 (ref1) and clone #54 efficiently blocked CD137-CD137L interaction, while the reference antibody 2 (ref2), clone #15, and clone #31 were less efficient or inefficient at blocking CD137-CD137L interaction.

Example 9

This example illustrates pharmacokinetics of anti-CD137 antibody leads in vivo.

Figure 11:
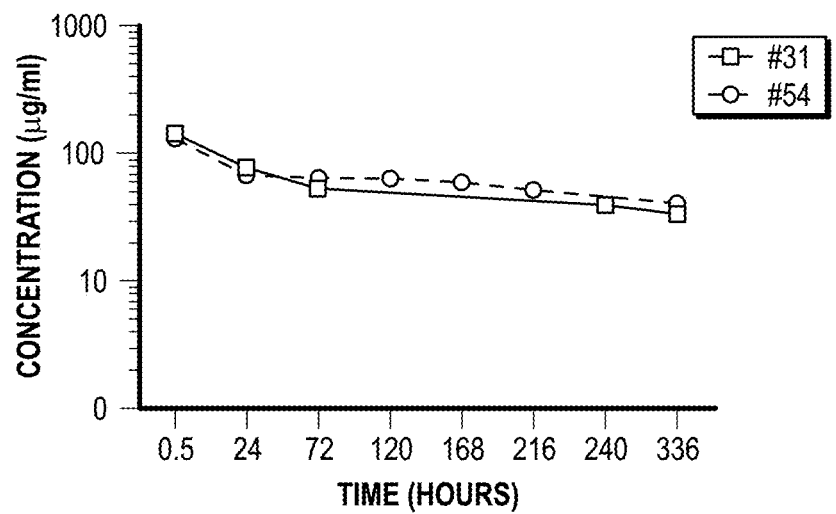
FIG. 11 shows the pharmacokinetic profiles of anti-CD137 antibody clone #31 and #54 in vivo.

Antibodies were administered at a dose of 5 mg per kg body weight by intravenous bolus injection into SCID-beige mice. Peripheral blood was collected at the indicated time points post injection. Antibody plasma concentrations were detected by ELISA as described below. CD137-human Fc (1 μg/mL) pre-coated wells were incubated with titrated concentrations of purified anti-CD137 IgG4 antibody to prepare a standard curve to calculate antibody concentrations in the plasma (using fresh preparations in blocking solution). Samples collected at different time points were also applied to pre-coated CD137-human Fc wells for detection. After washing with 0.1% Tween-20 in PBS, bound antibodies were detected using HRP-conjugated anti-human Fab antibody (0.4 μg/mL) before color development. Antibody plasma concentrations were calculated by the interpolation method. PK parameters were calculated using PKSolver software (Zhang, Huo, Zhou, & Xie, 2010). Antibodies showed a good $t_{1/2}$ of about 176 hours and an AUC of about 7800 ug/ml*h (FIG. 11).

Example 10

This example illustrates crosslinking-dependent agonistic activity of anti-CD137 antibody leads.

Figure 12:
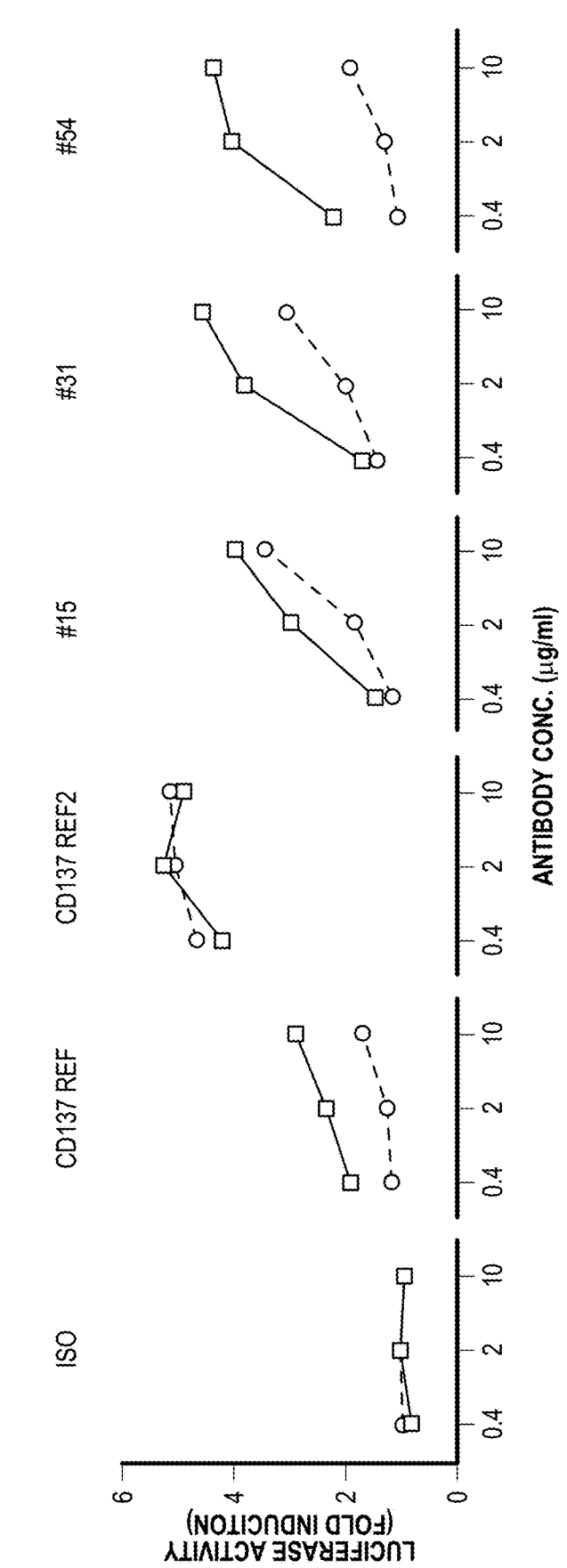
FIG. 12 shows different requirements of crosslinking for agonistic activity of anti-CD137 antibody clones compared to Utomilumab (CD137 ref) and Urelumab (CD137 ref 2).
Figure 13:
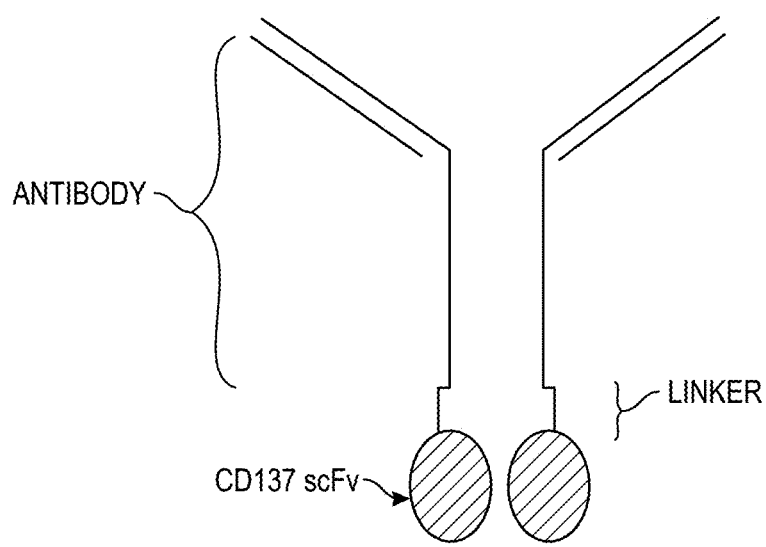
FIG. 13 shows the symmetric format of an anti-PD-L-CD137 bispecific antibody (bsAb).

Stable clones of CD137 reporter cells were generated by transfecting HEK293 cells with NF-κB-driven luciferase and full-length CD137, followed by selection with hygromycin and G418, respectively. For agonistic activity assays, anti-CD137 antibodies (10, 2, and 0.4 μg/ml) alone or crosslinked with goat anti-human IgG (5 µg/ml, Jackson ImmunoResearch, Catalog No. 109-006-008) were added to the reporter cells and incubated for 5 hours. Luciferase activity was detected using the ONE-Glo™ Luciferase Assay System (Promega, Cat. No. E6120). Consistent with previous reports, Utomilumab (CD137 ref, FIG. 12) showed crosslinking-dependent agonist activity, while Urelumab (CD137 ref2, FIG. 12) showed crosslinking-independent agonist activity that may cause the severe hepatotoxicity observed in clinical trials. Compared to Utomilumab, CD137 #54 showed greater agonistic activity upon crosslinking while agonist activity in the absence of crosslinking was moderate and similar to agonistic activity of Utomilumab (FIG. 12). Without being limited by theory, this characteristic of CD137 #54 may induce target-dependent T-cell activation when included in bispecific antibodies with tumor-specific binders.

In summary, these results show different cross-linking dependencies of anti-CD137 #15, anti-CD137 #31, anti-CD137 #54 agonist activity.

Example 11

This example illustrates construction, expression, and purification of anti-PD-L1-CD137 bispecific antibodies.

Anti-PD-L1 antibody clone 6 was used in IgG form without ADCC, and anti-CD137 antibody was used in scFv format and fused to the C-terminus of the anti-PD-L1 clone 6 antibody Fc region. Bispecific antibody constructs that include an anti-PD-L1 antibody Fc region fused with CD137 scFv are shown in Table 1 below (Sequences), with a schematic shown in FIG. 10. A short flexible peptide linker (GGGGS)2 (SEQ ID NO: 29) was placed between the anti-PD-L1 antibody heavy chain C-terminus of the Fc region (SEQ ID NO: 25 or SEQ ID NO:26) and the N-terminal module of the anti-CD137 scFv to ensure correct folding and minimize steric hindrance. The amino acid sequences of anti-PD-L1-CD137 scFv heavy chains are shown in SEQ ID NO:31 and SEQ ID NO:32. Antibody Fc fusion protein constructs were expressed using the Gibco ExpiCHO Expression System and purified from the cell culture supernatant of transfected cells via 1-step Protein G chromatography.

In addition to a bispecific anti-PD-L1 antibody Fc fused with anti-CD137 scFv described above, antibodies fused to anti-CD137 scFv can include anti-inhibitory immune checkpoint antibodies, such as anti-PD-1, anti-CTLA-4, anti-LAG3, and others, or immune stimulatory antibodies, such as anti-CD28, anti-CD40, anti-CD137, anti-CD27, anti-ICOS, and others. For each bispecific antibody, a linker can be placed between the antibody Fc domain and anti-CD137 scFv to generate the bispecific antibody.

Figure 14:
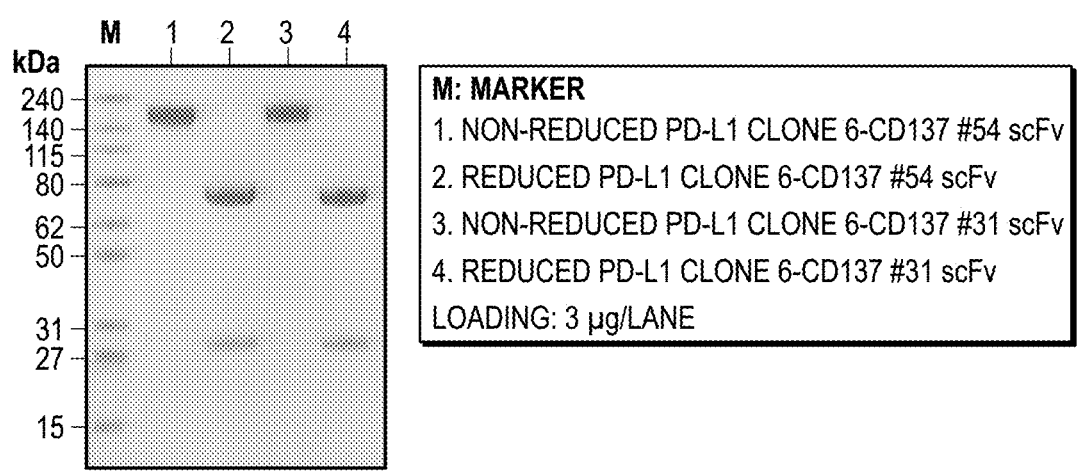
FIG. 14 shows the purity and integrity of protein G-purified anti-PD-L1-CD137 bsAbs by SDS-PAGE. More than 90% can be obtained by one step of Protein G chromatography.
Figure 15:
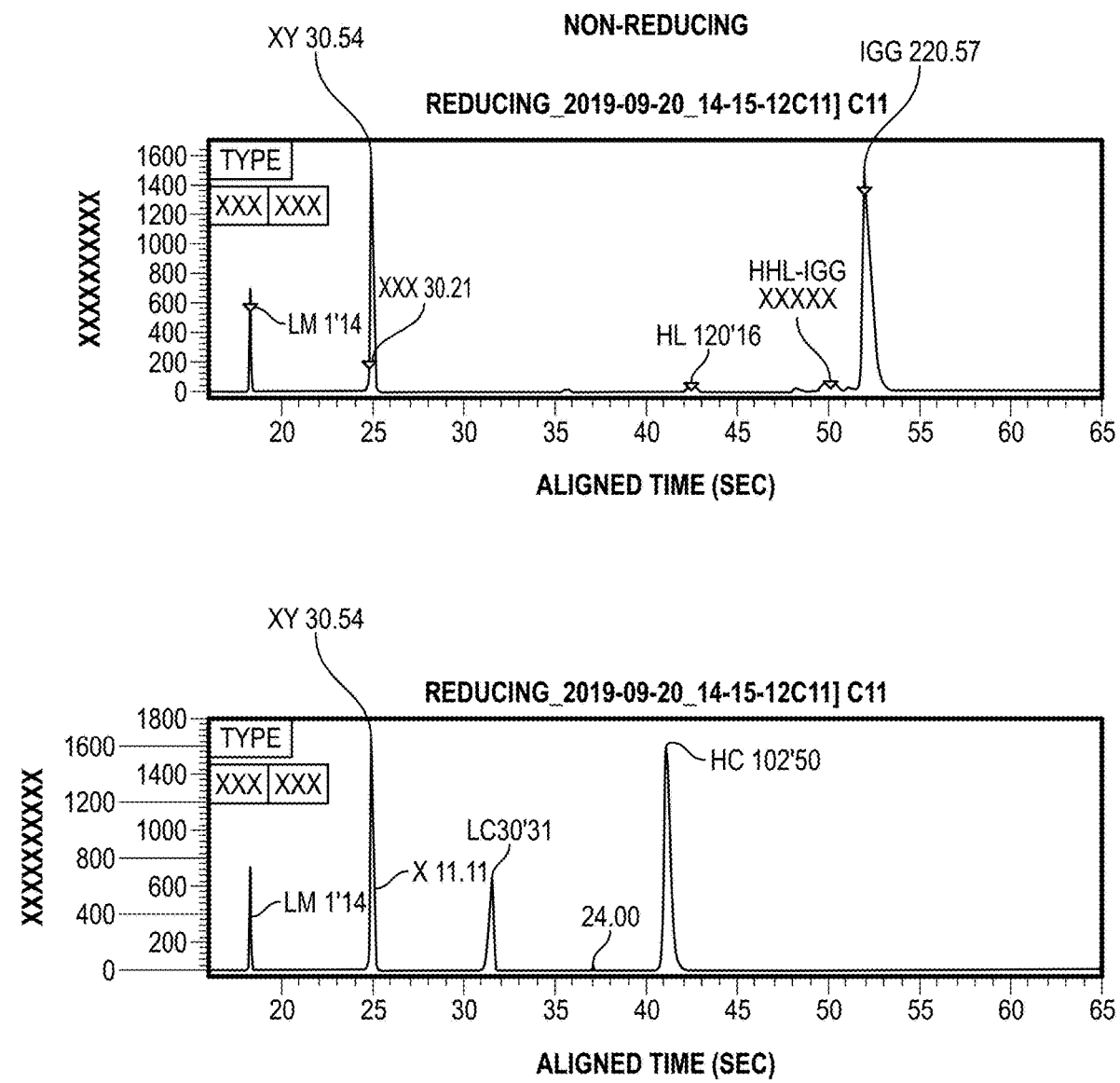
FIG. 15 shows the purity and integrity of protein A-purified anti-PD-L1-CD137 bsAbs by μCE-SDS.

The purity of bispecific antibodies was greater than 90% (FIG. 14 and FIG. 15). Purities greater than 90% were obtained in a single step purification process, consistent with purified fusion proteins having the correct molecular weight (Mw=220 kD). FIG. 14 shows a representative PAGE gel analysis of purified anti-PD-L-CD137 bispecific antibodies (bsAbs). Culture supernatants from mammalian cells collected 4 days post-transfection were purified using Protein G chromatography (Thermo Fisher). The purified proteins were analyzed under reducing or non-reducing condition before loading on the gel (3 µg/lane). Results indicated that both proteins have molecular weights of about 220 kDa under non-reducing conditions, and heavy chain-CD137 scFv and light chain have molecular weights of ~85 kDa and ~25 kDa under reducing condition, respectively. FIG. 15 shows the purity and integrity of one-step Protein A-purified anti-PD-L1 #6-CD137 #54 bsAb by µCE-SDS.

Example 12

This example illustrates antigen recognition by anti-PD-L-CD137 bispecific antibodies.

Binding activities of the anti-PD-L1-CD137 bispecific antibodies were determined by ForteBio® (Menlo Park, Calif.) biosensor analysis. His-tagged CD137 (ACROBiosystems) was loaded on a HIS1K (Anti-Penta-HIS) biosensor (Cat #18-5120) at 5 µg/mL in DPBS with 0.02% Tween-20 and 0.1% BSA for 5 minutes. Sensors were then exposed to the antibody as indicated at 100 nM using the same buffer for 5 minutes, followed by association with 100 nM of second antigen (PD-L1 fused to a mouse Fc domain) for another 5 minutes. The binding chart shown in FIG. 16 was then prepared using Octet Data Acquisition and Analysis Software as described by the manufacturer. Compared to control antibody, both bispecific antibodies (anti-PD-L1 #6-CD137 #31 and anti-PD-L1 #6-CD137 #54) could recognize first CD137 and then PD-L1 as well, demonstrating that bispecific antibodies could target PD-L1 and CD137 simultaneously.

In summary, these results show that anti-PD-L-CD137 bispecific antibodies simultaneously recognize PD-L1 and CD137, as determined by ForteBio® biosensor analysis.

Example 13

This example illustrates enhancement of T cell activation by anti-PD-L1 antibody and anti-PD-L1-CD137 scFv bispecific antibody (bsAb) in an allogenic mixed lymphocyte reaction.

Figure 17:
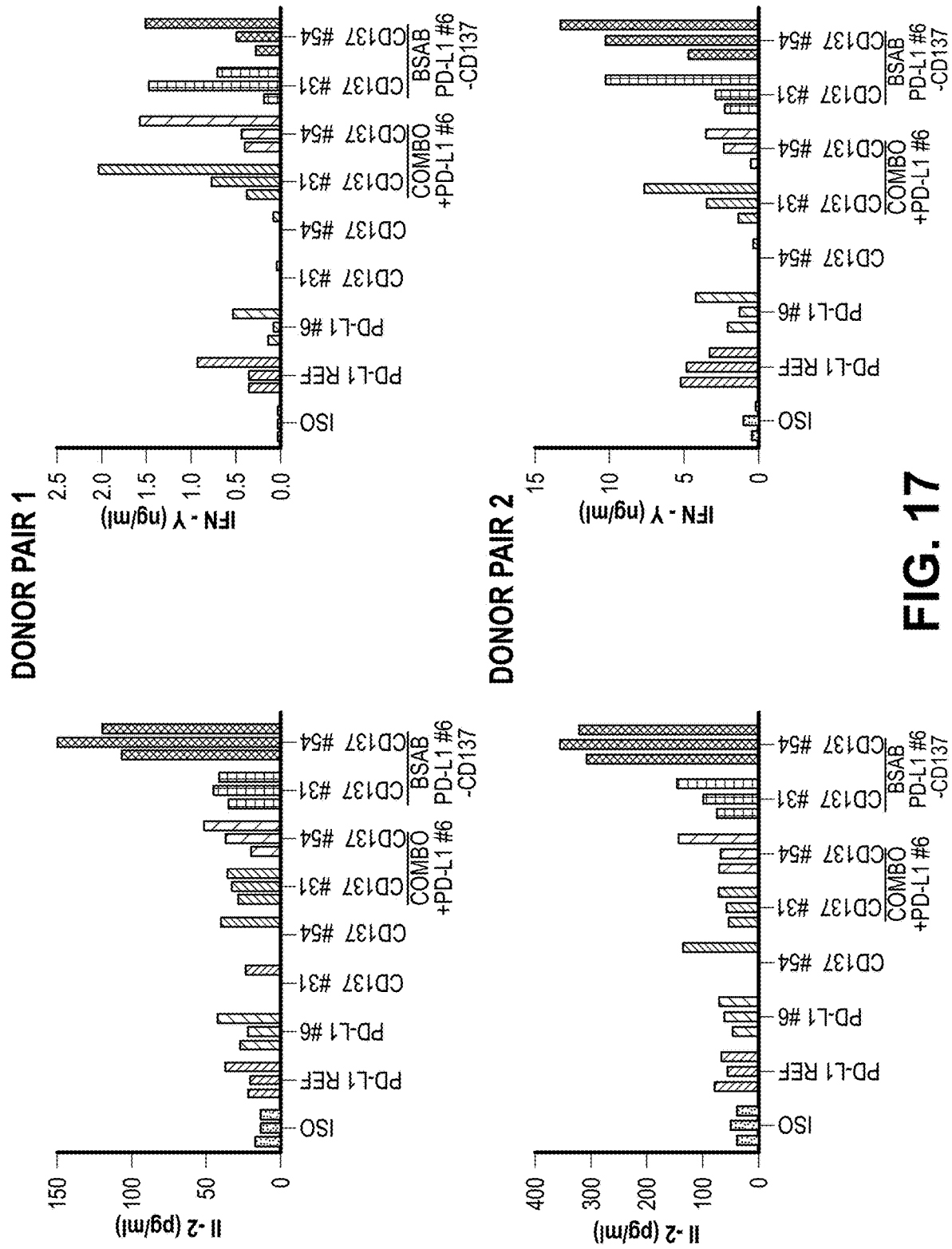
FIG. 17 shows that anti-PD-L1 #6-CD137 #54 bsAb induces synergistic T cell activation compared to monotreatment, combination treatment, or treatment with anti-PD-L1 #6-CD137 #31 bsAb in the mixed lymphocyte reaction.

Monocytes were isolated from peripheral blood of healthy donors by RosetteSep™ Human Monocyte Enrichment Cocktail (Cat. No. 15068) and cultured in RPMI1640 differentiation medium containing human GM-CSF and IL-4 (1000 U/ml each, R&D) for 6 days. Allogenic CD4+ T cells were isolated from human peripheral blood by RosetteSep™ Human CD4+ T Cell Enrichment Cocktail (Cat. No. 15062). The purity of CD4+ T cells was about 95% based on CD3 and CD4 expression. CFSE-labeled CD4+ T cells were co-cultured with DCs in the presence of antibody leads (1, 3, and 10 g/ml) for 3 and 5 days. CD4+ T cell proliferation was analyzed by flow cytometry and cytokine production of IL-2 and IFN-γ in the culture medium was detected by ELISA. Compared to the mono-treatment and combination treatment with anti-PD-L1 and anti-CD137 antibodies, anti-PD-L1 #6-CD137 #54 strikingly enhanced activation of T cells (FIG. 17, showing results for two donor pairs).

These results show that anti-PD-L1 #6-CD137 #54 bsAb induced a more potent T-cell activation in mixed lymphocyte reactions compared to the mono-treatment or combination treatment with anti-PDL-1 and anti-CD137 antibodies and compared to treatment with anti-PD-L1 #6-CD137 #31 bsAb.

Example 14

This example illustrates boosting of antigen-specific T-cell activation by anti-PD-L1-CD137 scFv bispecific antibody leads.

Human memory CD4 and CD8 T cells were isolated using an EasySep™ Human Memory CD4+ T Cell Enrichment Kit (STEMCELL, Cat. No. 19157) and a Human CD8+ T Cell Isolation Kit (STEMCELL, Cat. No. 17953), respectively.

Figure 18A:
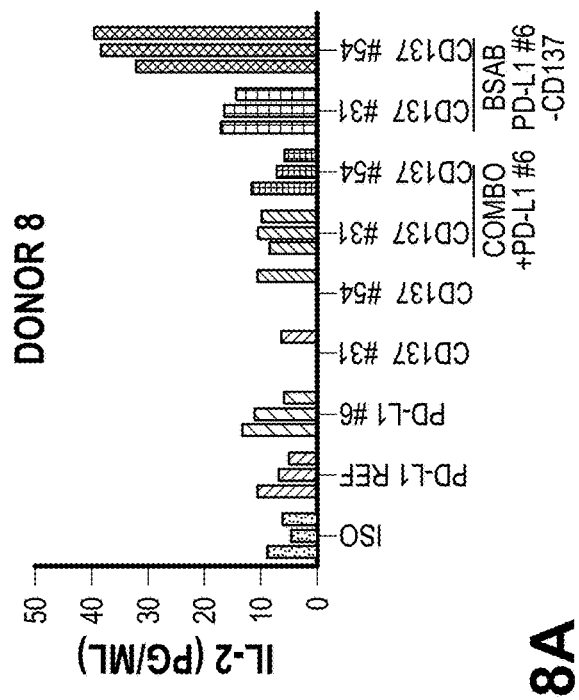
FIGS. 18A-18B show that the antigen-specific recall responses of memory CD4 (A) and memory CD8 (B) T cells are strikingly boosted by the anti-PD-L1 #6-CD137 #54 bsAb.
Figure 18B:
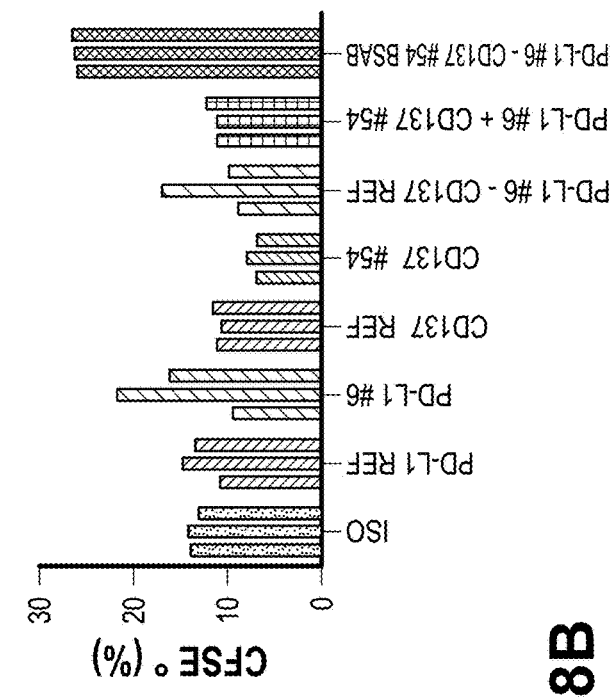

Cocultures of memory CD4-T cells and autologous immature DCs were stimulated with a CEFX Ultra SuperStim Pool MHC-II subset (1 ug/ml, JPT) in the presence of antibodies (0.4, 2, and 10 g/ml) for 7 days. For cocultures with CD8-T cells, TLR-DC generated as immature DCs were matured for 24 hours by adding IL-1β (10 ng/ml, PeproTech), TNF-α (10 ng/ml, PeproTech), IFN-γ (5000 IU/ml, PeproTech), PGE2 (250 ng/ml, Sigma), poly IC (10 µg/ml, Sigma), and R848 (5 µg/ml, Sigma) to the differentiation medium. Cocultures of CD8 T cells and autologous TLR-DCs were stimulated with a CEFX Ultra SuperStim Pool (1 µg/ml, JPT) in the presence of antibodies (0.4, 2, and 10 µg/ml) for 7 days. Similar to results observed in the MLR of Example 12, anti-PD-L1 #6-CD137 #54 bsAb boosted recall responses of memory CD4 T cells (FIG. 18, panel A) and CD8 T cells (FIG. 18, panel B) compared to monotreatment with anti-PD-L1 or anti-CD137 monoclonal antibody or combination treatment with anti-PD-L1 and anti-CD137 monoclonal antibodies (FIGS. 18A-B).

In summary, results shown in FIGS. 17 (Example 13) and 18 (this Example) show that anti-PD-L1 #6-CD137 #54 bsAb strikingly enhanced T-cell activation that was more robust than T-cell activation seen upon treatment with anti-PD-L1 and anti-CD137 monoclonal antibodies either alone or in combination. Moreover, T-cell activation seen upon treatment with anti-PD-L1 #6-CD137 #54 bsAb was antigen-dependent, as seen in recall response assays with CD4 and CD8 T cells. Without being limited by theory, the greater potency of T-cell activation seen with anti-PD-L1 #6-CD137 #54 bsAb as compared to anti-PD-L1 #6-CD137 #31 bsAb indicates that the anti-CD137 #54 arm of the bispecific antibody may bind to a unique CD137 epitope without steric hindrance resulting from binding to PD-L1 by the anti-PD-L1 arm of the bispecific antibody.

Example 15

This example illustrates anti-PD-L1-CD137 bispecific antibody-induced target-dependent T-cell activation.

Human T cells were isolated using a RosetteSep™ Human T Cell Enrichment Cocktail (STEMCELL Cat. No. 15061). Purified T cells were activated by plate-bound anti-CD3 (OKT3, 1 µg/ml) and cocultured with PD-L1-overexpressing or parental HEK293 cells under the indicated antibody treatments (FIG. 19). Compared to monotreatment or combination treatment with anti-PD-L1 and anti-CD137 monoclonal antibodies, anti-PD-L1-CD137 bispecific antibodies greatly boosted T cell activation upon coculture with PD-L1-overexpressing, but not the PD-L1-negative parental cells, as shown in FIG. 19.

In summary, these results show that target-dependent T-cell activation was only induced by anti-PD-L1 #6-CD137 bsAb when cocultured with PD-L1-overexpessing HEK-293 cells, but not parental HEK293 cells, in the presence plate-bound anti-CD3 (OKT3).

Example 16

This example illustrates tumor antigen-dependent T cell activation induced by anti-tumor antigen-specific CD137 #54 bispecific antibodies.

Human CD8-T cells were isolated by positive selection as described above (Example 15). Purified CD8-T cells were cocultured with PD-L1-positive tumor cells (NCI-H1975, PC-3, and MDA-MD-231) in the presence of anti-CD3 (OKT3)-coated polybeads at a 1:1 ratio. Three days later, T cell activation was assayed based on IFN-γ production as measured by ELISA, and tumor cell cytotoxicity was detected by CytoTox 96® Cytotoxicity Assay (Promega, Cat. #G1780).

More robust IFN-γ production was induced by anti-PD-L1 #6-CD137 #54 bsAb compared to the mono- or combination therapy with anti-PD-L1 #6 and anti-CD137 #54 antibodies (FIG. 20). Higher tumor cell cytotoxicity of CD8 T cells was observed in coculture with PC-3 cells (FIG. 20B). In addition to PD-L1-positive tumors, Her2-positive (SKBR-3 and MDA-MB-361) and glycan-positive (MCF-7 and NCI-N87) tumor cells targeted by anti-Her2 (Trastuzumab or #3-7) and anti-tumor glycan antibodies conjugated to CD137 #54 scFv also resulted in much stronger IFN-γ production (FIGS. 21A-B and FIGS. 22A-B) and tumor cell cytotoxicity (FIG. 22A) of CD8 T cells compared to mono- or combination therapy.

These results show that target-dependent T-cell activation was specifically induced by tumor-targeted CD137 #54 bsAb.

Example 17

This example illustrates induction of CD137 internalization by anti-PD-L1 #6-CD137 #54 bispecific antibody.

To test whether CD137 internalization is also induced by anti-PD-L1 #6-CD137 #54 bispecific antibody as well as the reference antibodies Urelumab and Utoliumab, an internalization assay was carried out with CD137 expressing HEK293 cells (FIG. 23). 5×10^3 CD137 expressing cells per well were pre-seeded on a black 96-well plate with Dulbecco's Modified Eagle Medium (Invitrogen) containing 10% fetal bovine serum (Gibco) and incubated overnight at 37° C., 5% $CO_2$. Antibodies as indicated were labeled with pHAb Amine Reactive dye (Promega Corp.) according to the manufacturer's protocol and then prepared as a 3-fold serial dilution from 100 nM in medium. The medium of pre-seeded cells was then replaced with medium containing labeled antibodies and cells were cultured for another 24 hours in the incubator. After incubation, cells were rinsed and kept in PBS for fluorescence recording by SpectraMax iD3. The EC50 value was calculated using GraphPad Prism. As shown in FIG. 23, stronger CD137 internalization induction was observed with anti-PD-L1 #6-CD137 #54 bispecific antibody treatment compared to treatment with reference anti-CD137 antibodies. Without being limited by theory, the level of CD137 internalization may reduce CD137 activation if the bispecfic Ab binds to the T cell through CD137 engagement alone. Accordingly, a lower toxicity may be seen with the bispecific antibody compared to reference antibodies, and especially compared to Urelumab, upon administration of the bispecific antibody in vivo.

Example 18

This example illustrates rescue of Treg cell-mediated inhibition of T cell proliferation by anti-PD-L1 #6-CD137 #54 bispecific antibody.

Figure 24A:
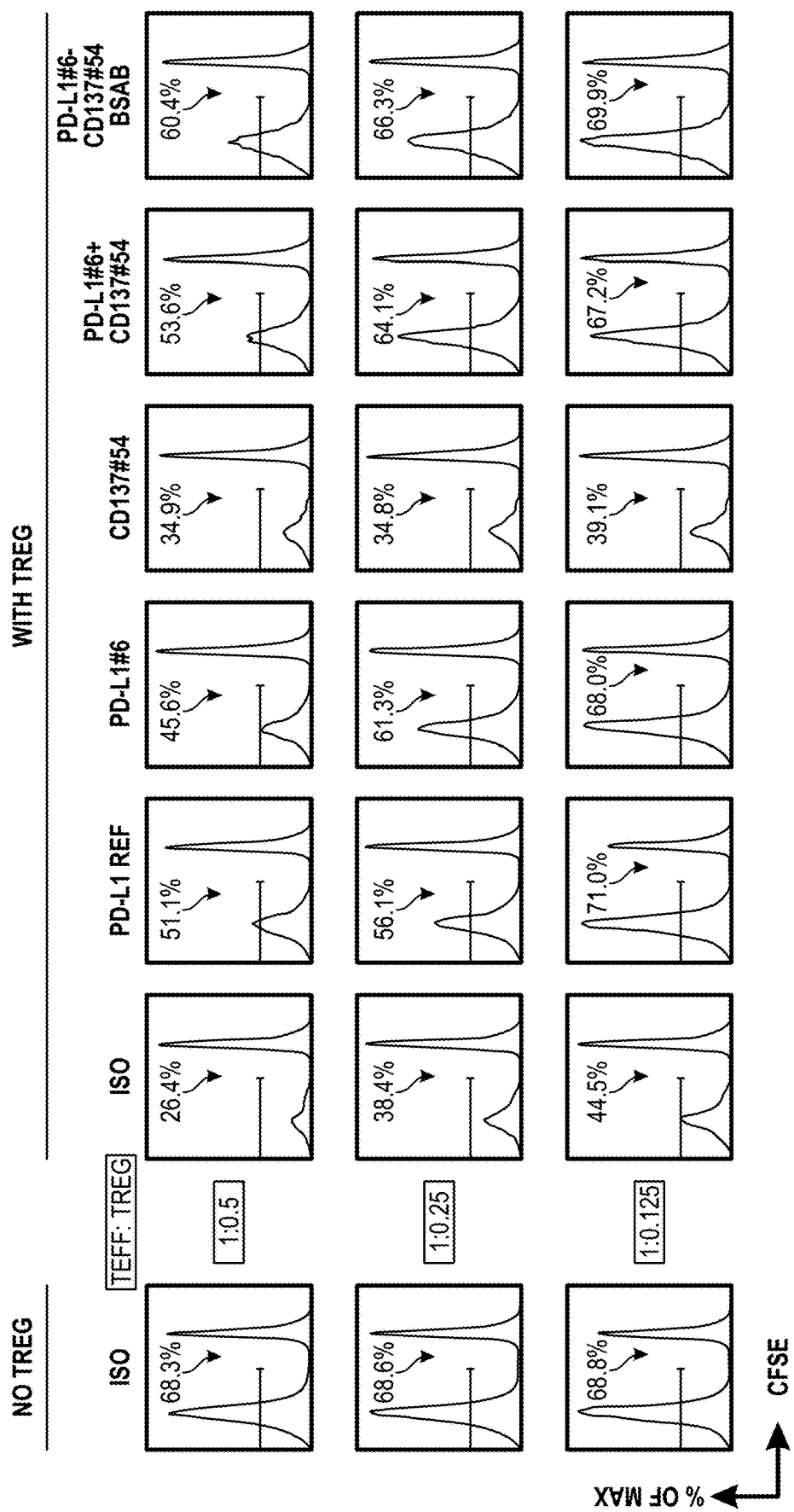
FIGS. 24A-24B show that anti-PD-L1 #6-CD137 bsAb rescued T-cell proliferation (A) and cytokine production (B) in the presence of Treg cells.
Figure 24B:
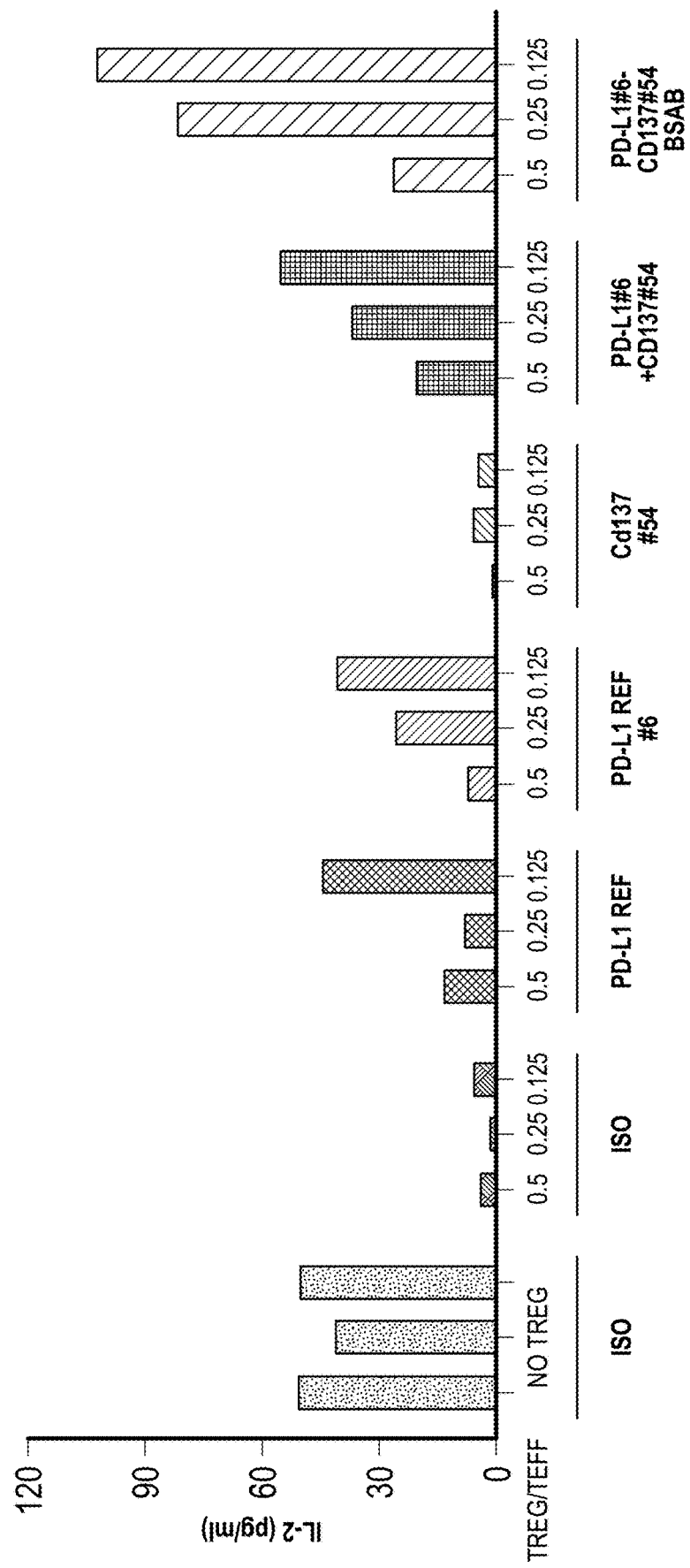

A Treg suppression assay was established using a mixed lymphocyte reaction as described in Example 12. Treg cells were isolated from peripheral blood using an EasySep™ Human $CD4^+CD127^{low}CD25^+$ Regulatory T Cell Isolation Kit (STEMCELL, Catalog no. 18063) and expanded using Dynabeads® Human Treg Expander (Gibco, Catalog no. 11129D). Expanded Treg cells greatly suppressed the proliferation and IL-2 production of CD4 T cells. The suppressive activity of Treg cells was abolished by adding anti-PD-L1 #6-CD137 #54 bsAb to the culture (FIGS. 24A-B).

Anti-PD-L1 #6-CD137 #54 bsAb rescued both T-cell proliferation (FIG. 24, panel A) and cytokine production (FIG. 24, panel B) in the presence of Treg cells. These results show that anti-PD-L1 #6-CD137 #54 bsAb was able to rescue T-reg mediates suppression of T-cell activation.

Example 19

This example illustrates inhibition of tumor growth by anti-PD-L1 #6-CD137 #54 bispecific antibody in vivo.

Figure 25B:
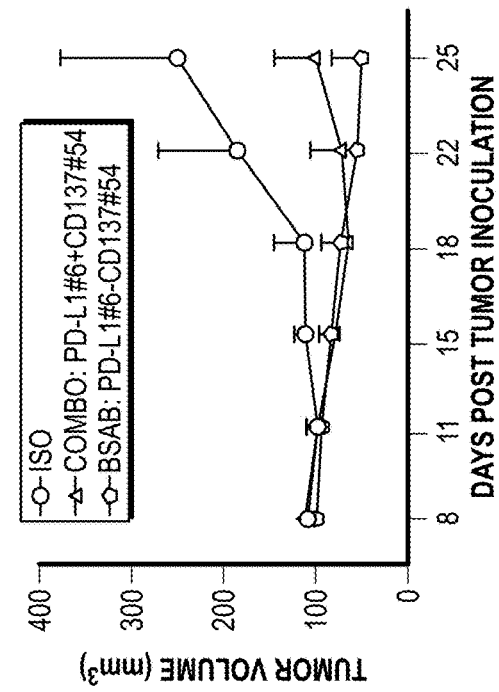
FIGS. 25A-25C show that anti-PD-L1 #6-CD137 #54 bsAb results in greater tumor growth inhibition compared to combination treatment with anti-PD-L1 #6 and anti-CD137 #54 antibodies in humanized mice xenografted with PD-L-positive (A) NCI-H292, (B) NCI-H1975, and (C) BxPC-3 tumor cells.
Figure 25A:
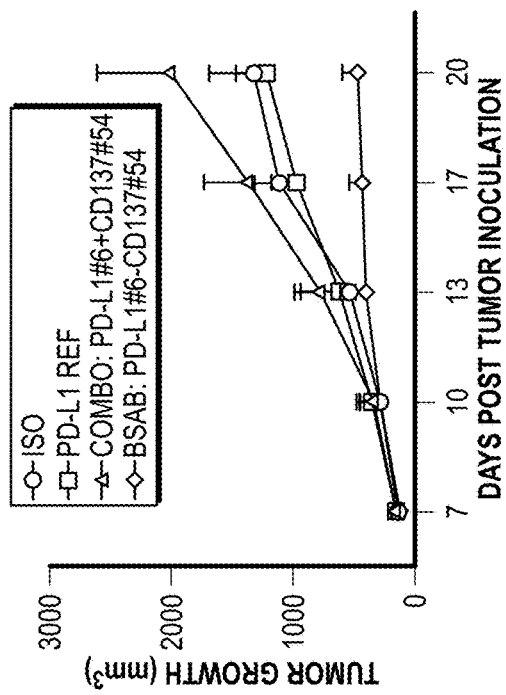
Figure 25C:
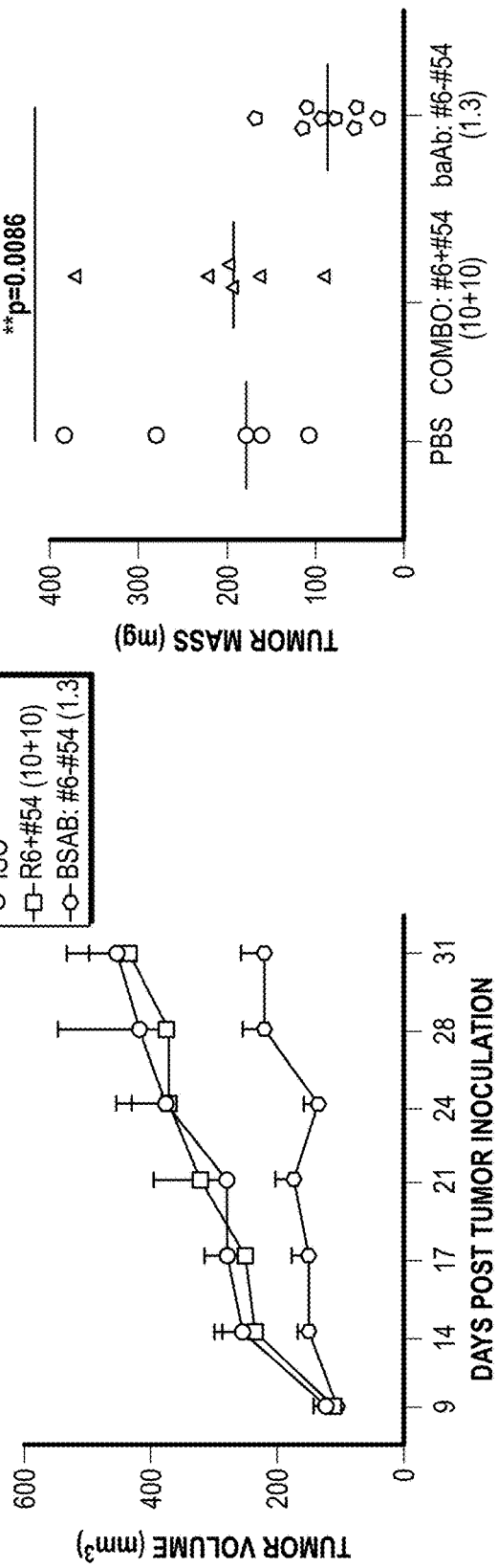

To validate the anti-tumor activity of anti-PD-L1 #6-CD137 #54 bsAb, which does not cross-react with mouse PD-L1 and mouse CD137, human tumor cells (NCI-H292, NCI-H1975 and BxPC-3) were premixed with human PBMC and xenografted subcutaneously to SCID-beige mice to evaluate anti-cancer activity in vivo. Seven days post tumor inoculation, equal moles of mAb (M.W.150 kDa, 1 mg/kg) and bsAb (M.W. 195 kDa, 1.3 mg/kg) were intraperitoneally injected twice per week. Tumor sizes (mm³) were measured twice per week and calculated as (length×width×width)/2. The tumor growth inhibition index (TGI) of anti-PD-L1 #6-CD137 #54 bsAb (TGI: 67.5%) was greater than that of MPDL-3280a (TGI: 44.3%) and the combination of PD-L1 #6+CD137 #54 (TGI: −18.77%) in the NCI-H292 tumor model (FIG. 25, panel A). Similarly, the TGI of anti-PD-L1 #6-CD137 #54 bsAb (TGI: 80%) was greater than that of the combination of PD-L1 #6+CD137 #54 (TGI: 67.2%) in the NCI-H1975 tumor model (FIG. 25, panel B). In addition to lung cancers, anti-PD-L1 #6-CD137 #54 bsAb also showed greater anti-tumor activity (TGI of 1.3 mg/kg was 43%) compared to combination therapy (TGI of 10 mg/ml each: −9.2%) in the BxPC-3 pancreatic cancer model (FIG. 25, panel C). Thus, anti-PD-L1 #6-CD137 #54 bsAb showed anti-tumor activity in two different cancer models in vivo.

In summary, these results show greater inhibition of tumor growth upon treatment with anti-PD-L1 #6-CD137 #54 bsAb compared to combination treatment with anti-PD-L1 and anti-CD137 antibodies in xenograft tumor models in mice.

Example 20

This example illustrates cytokine release in the presence of bispecific antibodies in vitro.

Figure 26:
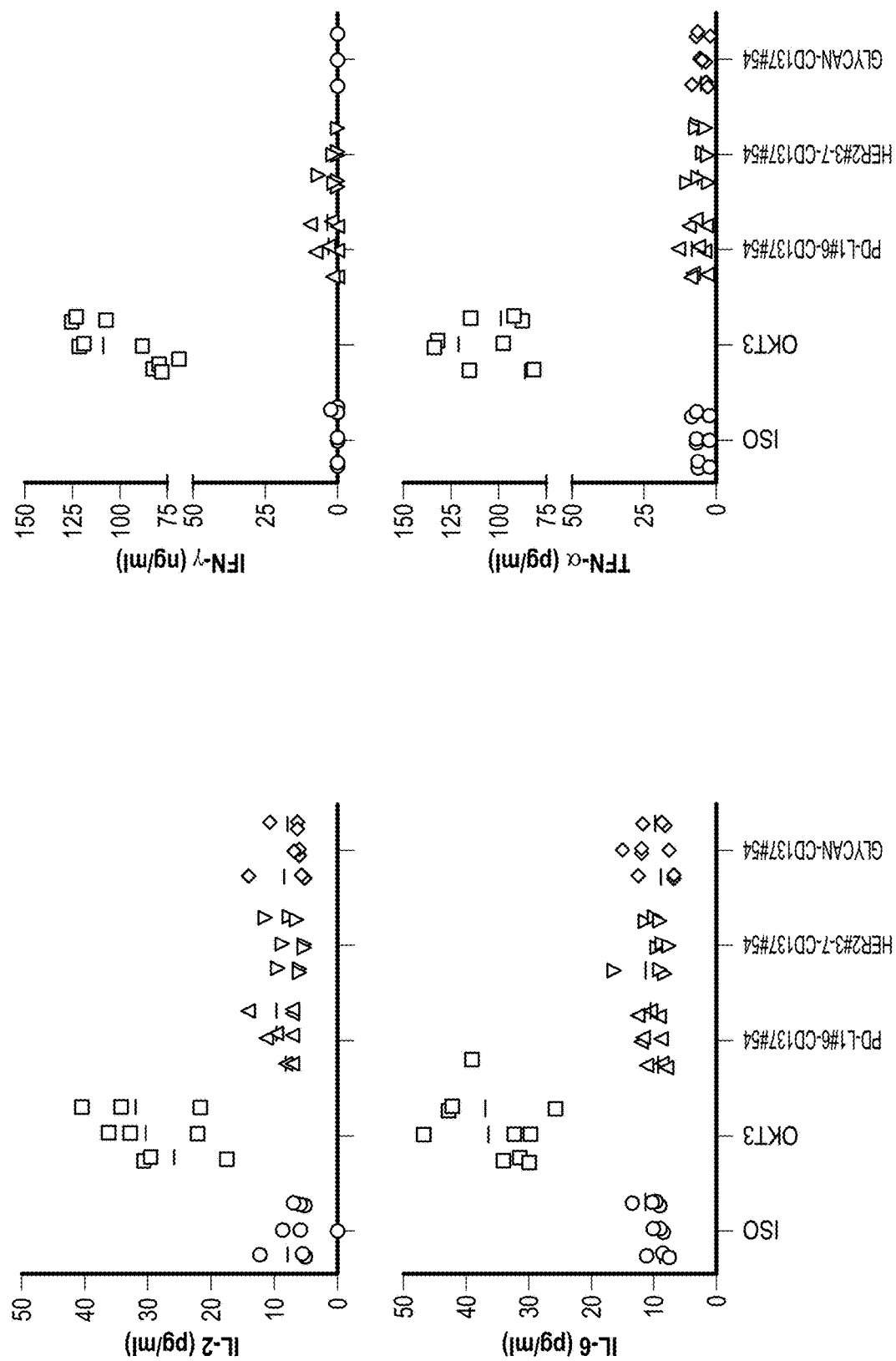
FIG. 26 shows that PD-L1 #6-CD137 #54, Her2 #3-7-CD137 #54 and glycan-CD137 #54 bsAbs do not induce noticeable cytokine release in human PBMC.
Figure 26:
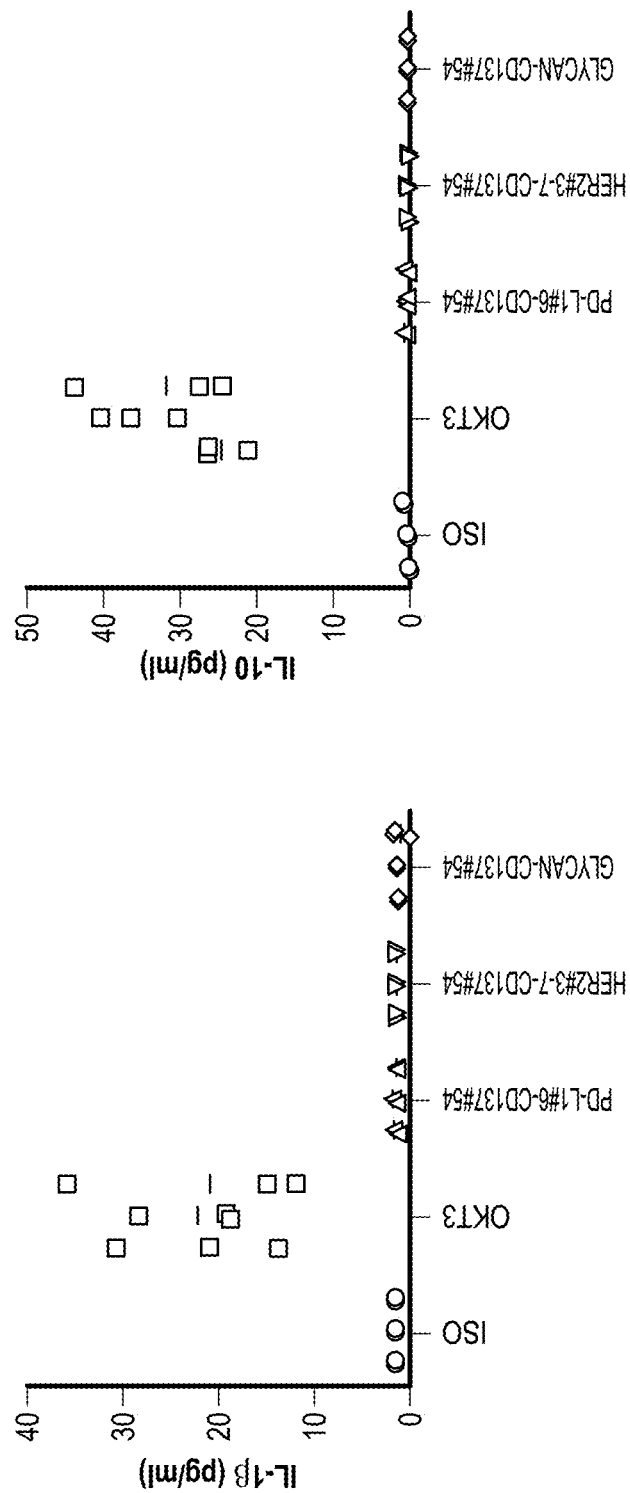

Human PBMCs from three donors were incubated with isotype, anti-CD3 antibody (OKT3, as positive control), and three bispecific antibodies (anti-PD-L1 #6, anti-Her2 #3-7, and anti-glycan conjugated to CD137 #54 scFv) at 0.67, 6.67, and 66.67 nM for 24 hours. Cytokines released into the culture medium were detected by the multiplex ProcartaPlex Immunoassay (ThermoFisher Scientific). A profound cytokine release was induced by OKT3, while the three bispecific antibodies did not induce cytokine release (FIG. 26).

These results show that, compared to OKT3, PD-L1 #6-CD137 #54, Her2 #3-7-CD137 #54 and glycan-CD137 #54 bsAbs did not induce noticeable cytokine release above background when incubated with human PBMC.

Example 21

This example illustrates pharmacokinetic parameters of an anti-PD-L1 #6-CD137 #54 bispecific antibody in rhesus monkeys.

Figures 27A, 27B:
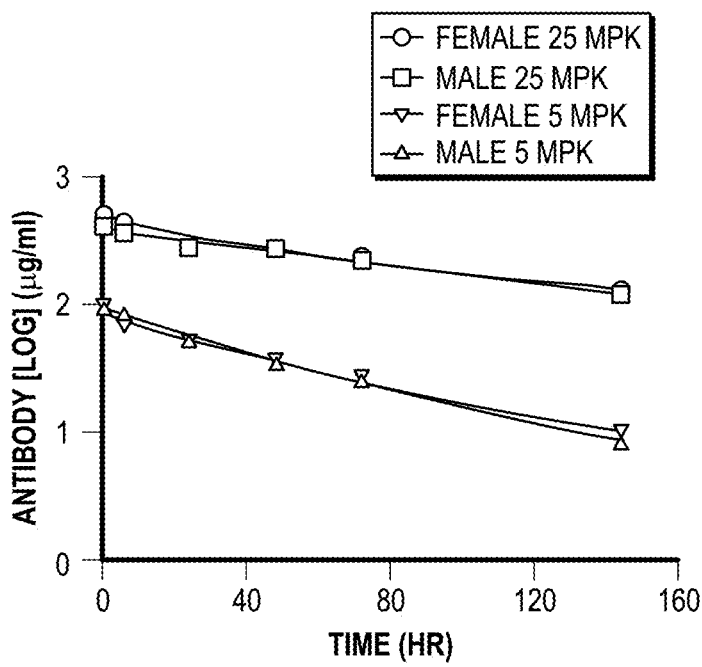
FIGS. 27A-27B show PK parameters of anti-PD-L1 #6-CD137 #54 bsAb in monkeys as (A) a graph and (B) in tabular form.

The bispecific anti-PD-L1 #6-CD137 #54 antibody (5 and 25 mg per kg body weight) was administered via an intravenous bolus injection to two groups (one male and one female per group) of rhesus monkeys. Peripheral blood was collected at 0.5, 6, 24, 48, 72, and 144 hours post injection. Plasma concentrations of the antibody were determined by ELISA. MaxiSorp plates (Invitrogen) were coated with CD137-Fc fusion protein (AP Biosciences, 1 μg/mL), followed by application of serially-diluted plasma samples and anti-PD-L1 #6-CD137 #54 bsAb as the standard curve. Bound antibodies were detected by biotinylated PD-L1-Fc fusion protein (AP Biosciences) and HRP-conjugated streptavidin using TMB substrate. Plasma antibody concentrations were calculated by the interpolation method. PK parameters were calculated using PKSolver software (Zhang, Huo, Zhou, & Xie, 2010). The $t_{1/2}$ of anti-PD-L1 #6-CD137 #54 bsAb were about 87 and 49 hours in the 25 mg/kg- and 5 mg/kg-injected groups, respectively (FIGS. 27A-B), and no elevated levels of ALT/AST were observed during the experimental period (not shown).

SEQUENCES
SEQ ID NO 1: Anti-CD137 clone 15 heavy chain
QVQLVQSGAEVKKPGSSVKVSCKASGGTFSSYAISWVRQAPGQGLEWMG

RIIPILGIANYAQKFQGRVTITADKSTSTAYMELSSLRSEDTAVYYCAS

DLYQLLFPYYYGMDVWGQGTTVTVSS

SEQ ID NO 2: Anti-CD137 clone 15 light chain
QLVLTQPPSASASLGASVTLTCTLSSGYSNYKVDWYQQRPGKGPRFVMR

VGTGGIVGSKGDGIPDRFSVLGSGLNRYLTIKNIQEEDESDYHCGADHG

SGSNLFWVFGGGTKLTVLGQPKAAPSVTLFPPSSEELQANKATLVCLIS

DFYPGAVTVAWKADSSPVKAGVETTTPSKQSNNKYAASSYLSLTPEQWK

SHRSYSCQVTHEGSTVEKTVAPTECS

SEQ ID NO 3: CDR-H1 of anti-CD137 clone 15
GGTFSSY

SEQ ID NO 4: CDR-H2 of anti-CD137 clone 15
IPILGI

SEQ ID NO 5: CDR-H3 of anti-CD137 clone 15
DLYQLLFPYYYGMDV

SEQ ID NO 6: CDR-L1 of anti-CD137 clone 15
TLSSGYSNYKVD

SEQ ID NO 7: CDR-L2 of anti-CD137 clone 15
VGTGGIVGSKGD

SEQ ID NO 8: CDR-L3 of anti-CD137 clone 15
GADHGSGSNLFWV

SEQ ID NO 9: Anti-CD137 clone 31 heavy chain
QVQLVQSGAEVKKPGASVKVSCKASGYTFTGYYMHWVRQAPGQGLEWMG

WINPNSGGTNYAQKFQGRVTMTRDTSISTAYMELSRLRSDDTAVYYCAR

DLRGAFDPWGQGTTVTVSS

SEQ ID NO 10: Anti-CD137 clone 31 light chain
QSALTQPASVSGSPGQSITISCTGTSSDVGAYNFVSWYQQRPGKAPELM

IYDVSDRPSGVSNRFSGSKSGNTASLTISGLQTEDEADYYCSSYTSSIT

RYVFGTGTKVTVLGQPKANPTVTLFPPSSEELQANKATLVCLISDFYPG

AVTVAWKADGSPVKAGVETTKPSKQSNNKYAASSYLSLTPEQWKSHRSY

SCQVTHEGSTVEKTVAPTECS

SEQ ID NO 11: CDR-H1 of anti-CD137 clone 31
GYTFTGY

SEQ ID NO 12: CDR-H2 of anti-CD137 clone 31
NPNSGG

SEQ ID NO 13: CDR-H3 of anti-CD137 clone 31
DLRGAFDP

SEQ ID NO 14: CDR-L1 of anti-CD137 clone 31
TGTSSDVGAYNFVS

SEQ ID NO 15: CDR-L2 of anti-CD137 clone 31
DVSDRPS

SEQ ID NO 16: CDR-L3 of anti-CD137 clone 31
SSYTSSITRYV

SEQ ID NO 17: Anti-CD137 clone 54 heavy chain
QVQLVQSGAEVKKPGSTVKVSCKASGGTFSSYAISWVRQAPGQGLEWMG
RIIPILGIANYAQKFQGRVTITADKSTSTAYMELSSLRSEDTAVYYCAS
PPYYDSSGYYPLGAFDIWGQGTMVTVSS SEQ ID NO 18: Anti-CD137 clone 54 light chain
SYELTQPPSVSVSPGQTASITCSGDKLGEKYASWYQQKAGQSPILVIYQ
DSKRPSGIPERFSGSNSGNTATLTISGLQAGDEADYYCQAWDGSSTYVF
GTGTKVTVFGQPKANPTVTLFPPSSEELQANKATLVCLISDFYPGAVTV
AWKADGSPVKAGVETTKPSKQSNNKYAASSYLSLTPEQWKSHRSYSCQV
THEGSTVEKTVAPTECS SEQ ID NO 19: CDR-H1 of anti-CD137 clone 54
GGTFSSY SEQ ID NO 20: CDR-H2 of anti-CD137 clone 54
IPILGI SEQ ID NO 21: CDR-H3 of anti-CD137 clone 54
PPYYDSSGYYPLGAFDI SEQ ID NO 22: CDR-L1 of anti-CD137 clone 54
SGDKLGEKYAS SEQ ID NO 23: CDR-L2 of anti-CD137 clone 54
QDSKRPS SEQ ID NO 24: CDR-L3 of anti-CD137 clone 54
QAWDGSSTYV SEQ ID NO 25: constant domain in heavy chain
(IgG4)
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESKYGPPCPPCPAPEFLGGPSVFLFPPKPKDTLMISRTPEVTCVVVDVS
QEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDK
SRWQEGNVFSCSVMHEALHNHYTQKSLSLSLGK SEQ ID NO 26: constant domain in heavy chain
(engineered IgG1)
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYASTYRVVSVLTVLHQDW
LNGKEYKCAVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPG

SEQ ID NO 27: SP1
METDTLLLWVLLLWVPGSTG

SEQ ID NO 28: GS linker
GGGGS

SEQ ID NO 29: (G4S)2 linker
GGGGSGGGGS

SEQ ID NO 30: Anti-PD-L1#6 Light Chain
QSVLTQPPSASGTPGQRVTISCSGSSSNIGSNTVNWYQQLPGTAPKLLI
YSNNQRPSGVPDRFSGSKSGTSASLAISGLQSEDEADYYCATWDLSLNA
WVVFGGGTKLTVLGQPKAAPSVTLFPPSSEELQANKATLVCLISDFYPG
AVTVAWKADSSPVKAGVETTTPSKQSNNKYAASSYLSLTPEQWKSHRSY
SCQVTHEGSTVEKTVAPTECS SEQ ID NO 31: Anti-PD-L1 #6-CD137 #31 bsAb Heavy
Chain
QVQLVQSGAEVKKPGSSVKVSCKASGGTFRRYSISWVRQAPGQGLEWMG
GIIPVFGAAKYAQKFQGRVTITADEFTSTAYMELSSLTSEDTAVYYCAL
SGDSDAFDIWGQGTMVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYASTYRVVSVLTVLHQDWLNGKEYKCAVSNKALPAPIEKTISKAKGQ
PREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKS
LSLSPGGGGSGGGGQSALTQPASVSGSPGQSITISCTGTSSDVGAYNF
VSWYQQRPGKAPELMIYDVSDRPSGVSNRFSGSKSGNTASLTISGLQTE
DEADYYCSSYTSSITRYVFGTGTKVTVLGGGGSGGGGSGGGGSQVQLVQ
SGAEVKKPGASVKVSCKASGYTFTGYYMHWVRQAPGQGLEWMGWINPNS
GGTNYAQKFQGRVTMTRDTSISTAYMELSRLRSDDTAVYYCARDLRGAF
DPWGQGTTVTVSSA SEQ ID NO 32: Anti-PD-L1#6-CD137 #54 bsAb Heavy
Chain
QVQLVQSGAEVKKPGSSVKVSCKASGGTFRRYSISWVRQAPGQGLEWMG
GIIPVFGAAKYAQKFQGRVTITADEFTSTAYMELSSLTSEDTAVYYCAL
SGDSDAFDIWGQGTMVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPRE
EQYASTYRVVSVLTVLHQDWLNGKEYKCAVSNKALPAPIEKTISKAKGQ
PREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKS
LSLSPGGGGSGGGGSQVQLVQSGAEVKKPGSTVKVSCKASGGTFSSYA
ISWVRQAPGQGLEWMGRIIPILGIANYAQKFQGRVTITADKSTSTAYME LSSLRSEDTAVYYCASPPYYDSSGYYPLGAFDIWGQGTMVTVSSAGGGG
SGGGGSGGGGSGGGGSSYELTQPPSVSVSPGQTASITCSGDKLGEKYAS
WYQQKAGQSPILVIYQDSKRPSGIPERFSGSNSGNTATLTISGLQAGDE
ADYYCQAWDGSSTYVFGTGTKVTVLG SEQ ID NO 33: CD137#31-scFv
QSALTQPASVSGSPGQSITISCTGTSSDVGAYNFVSWYQQRPGKAPELM
IYDVSDRPSGVSNRFSGSKSGNTASLTISGLQTEDEADYYCSSYTSSIT
RYVFGTGTKVTVLGGGGSGGGGSGGGGSQVQLVQSGAEVKKPGASVKVS
CKASGYTFTGYYMHWVRQAPGQGLEWMGWINPNSGGTNYAQKFQGRVTM
TRDTSISTAYMELSRLRSDDTAVYYCARDLRGAFDPWGQGTTVTVSSA SEQ ID NO 34: CD137#54-scFv
QVQLVQSGAEVKKPGSTVKVSCKASGGTFSSYAISWVRQAPGQGLEWMG
RIIPILGIANYAQKFQGRVTITADKSTSTAYMELSSLRSEDTAVYYCAS
PPYYDSSGYYPLGAFDIWGQGTMVTVSSAGGGGSGGGGSGGGGSGGGGS
SYELTQPPSVSVSPGQTASITCSGDKLGEKYASWYQQKAGQSPILVIYQ
DSKRPSGIPERFSGSNSGNTATLTISGLQAGDEADYYCQAWDGSSTYVF
GTGTKVTVLG SEQ ID NO 35: Trastuzumab Light Chain
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID NO 36: Trastuzumab-CD137 #54 bsAb Heavy
Chain
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYASTYRVVSVLTVLHQDWLNGKEYKCAVSNKALPAPIEKTISKAK
GQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQ
KSLSLSPGGGGSGGGGSQVQLVQSGAEVKKPGSTVKVSCKASGGTFSS
YAISWVRQAPGQGLEWMGRIIPILGIANYAQKFQGRVTITADKSTSTAY
MELSSLRSEDTAVYYCASPPYYDSSGYYPLGAFDIWGQGTMVTVSSAGG
GGSGGGGSGGGGSSYELTQPPSVSVSPGQTASITCSGDKLGEKY
ASWYQQKAGQSPILVIYQDSKRPSGIPERFSGSNSGNTATLTISGLQAG
DEADYYCQAWDGSSTYVFGTGTKVTVLG SEQ ID NO 37: Anti-Her2 #3-7 Light Chain
QTVVTQEPSFSVSPGGTVTLTCGLSSGSVSTSYYPSWYQQTPGQAPRTL
IYSSTNTRSSGVPDRFSGSILGNKAALTITGAQADDESDYYCVLYMGSGI

WVFGGGTKLTVLGQPKAAPSVTLFPPSSEELQANKATLVCLISDFYPGA
VTVAWKADSSPVKAGVETTTPSKQSNNKYAASSYLSLTPEQWKSHRSYS
CQVTHEGSTVEKTVAPTECS

SEQ ID NO 38: Anti-Her2 #3-7-CD137 #54 bsAb Heavy
Chain
EVQLVQSGAEVKKPGESLKISCKGSGYSFTSYWIGWVRQMPGKGLEWMG
IIYPGDSDTRYSPSFQGQVTISADKSISTAYLQWSSLKASDTAMYYCAR
QDNWNHGPYDAFDIWGQGTMVTVSSASTKGPSVFPLAPSSKSTSGGTAA
LGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAK
TKPREEQYASTYRVVSVLTVLHQDWLNGKEYKCAVSNKALPAPIEKTIS
KAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNH
YTQKSLSLSPGGGGSGGGGSQVQLVQSGAEVKKPGSTVKVSCKASGGT
FSSYAISWVRQAPGQGLEWMGRIIPILGIANYAQKFQGRVTITADKSTS
TAYMELSSLRSEDTAVYYCASPPYYDSSGYYPLGAFDIWGQGTMVTVSS
AGGGGSGGGGSGGGGSGGGGSSYELTQPPSVSVSPGQTASITCSGDKLG
EKYASWYQQKAGQSPILVIYQDSKRPSGIPERFSGSNSGNTATLTISGL
QAGDEADYYCQAWDGSSTYVFGTGTKVTVLG SEQ ID NO 39: Anti-Glycan Light Chain
EIVLTQSPSTLSLSPGERATLSCQASEDVSYMHWYQQKPGQAPQPWIYG
TSNKASGVPSRFSGSGSGTDFTLTISSLQPEDVATYYCQQWSRRPFTFG
QGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVT
HQGLSSPVTKSFNRGEC SEQ ID NO 40: Anti-Glycan-CD137 #54 bsAb Heavy
Chain
QITLQESGPTLVKPTQTLTFSGFSLYRFDMGVGWIRQPPGQGLEWLAHI
WWDDDKYYNPALKSRLTISKDTSKNQVVLTMTNMDPVDTATYYCARVRG
LHDYYYYFAYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYASTYRVVSVLTVLHQDWLNGKEYKCAVSNKALPAPIEKTISKAKG
QPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQK
SLSLSPGGGGSGGGGSQVQLVQSGAEVKKPGSTVKVSCKASGGTFSSY
AISWVRQAPGQGLEWMGRIIPILGIANYAQKFQGRVTITADKSTSTAYM
ELSSLRSEDTAVYYCASPPYYDSSGYYPLGAFDIWGQGTMVTVSSAGGG
GSGGGGSGGGGSGGGGSSYELTQPPSVSVSPGQTASITCSGDKLGEKYA
SWYQQKAGQSPILVIYQDSKRPSGIPERFSGSNSGNTATLTISGLQAGD
EADYYCQAWDGSSTYVFGTGTKVTVLG -continued SEQ ID NO 41: CDR-H1 of anti-Her2#3-7
GYSFTSY SEQ ID NO 42: CDR-H2 of anti-Her2#3-7
YPGDSD SEQ ID NO 43: CDR-H3 of anti-Her2#3-7
QDNWNHGPYDAFDI SEQ ID NO 44: CDR-L1 of anti-Her2#3-7
GLSSGSVSTSYYPS SEQ ID NO 45: CDR-L2 of anti-Her2#3-7
STNTRSS SEQ ID NO 46: CDR-L3 of anti-Her2#3-7
VLYMGSGIWV

TABLE 1

Sequences of Defined CDR Regions of Monoclonal Antibodies and Single Chain Variable Fragments (scFv) of Bispecific Antibodies.

| Name | Sequences | | |
|---|---|---|---|
| | CDR1 | CDR2 | CDR3 |
| CD137#15-H | GGTFSSY (SEQ ID NO: 3) | IPILGI (SEQ ID NO: 4) | DLYQLLFPYYYGMDV (SEQ ID NO: 5) |
| CD137#15-L | TLSSGYSNYKVD (SEQ ID NO: 6) | VGTGGIVGSKGD (SEQ ID NO: 7) | GADHGSGSNLFW (SEQ ID NO: 8) |
| CD137#31-H | GYTFTGY (SEQ ID NO: 11) | NPNSGG (SEQ ID NO: 12) | DLRGAFDP (SEQ ID NO: 13) |
| CD137#31-L | TGTSSDVGAYNFVS (SEQ ID NO: 14) | DVSDRPS (SEQ ID NO: 15) | SSYTSSITRYV (SEQ ID NO: 16) |
| CD137#54-H | GGTFSSY (SEQ ID NO: 19) | IPILGI (SEQ ID NO: 20) | PPYYDSSGYYPLGAFDI (SEQ ID NO: 21) |
| CD137#54-L | SGDKLGEKYAS (SEQ ID NO: 22) | QDSKRPS (SEQ ID NO: 23) | QAWDGSSTYV (SEQ ID NO: 24) |
| Her2#3-7-H | GYSFTSY (SEQ ID NO: 41) | YPGDSD (SEQ ID NO: 42) | QDNWNHGPYDAFDI (SEQ ID NO: 43) |
| Her2#3-7-L | GLSSGSVSTSYYPS (SEQ ID NO: 44) | STNTRSS (SEQ ID NO: 45) | VLYMGSGIWV (SEQ ID NO: 46) |
| CD137#31-scFv | QSALTQPASVSGSPGQSITISCTGTSSDVGAYNFVSWYQQRPGKAPELMIYDVSDRPSGVSNRFSGSKSGNTASLTISGLQTEDEADYYCSSYTSSITRYVFGTGTKVTVLGGGGSGGGGSGGGGSQVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARDLRGAFDPWGQGTTVTVSSA (SEQ ID NO: 33) | | |
| CD137#54-scFv | QVQLVQSGAEVKKPGSTVKVSCKASGGTFSSYAISWVRQAPGQGLEWMGRIIPILGIANYAQKFQGRVTITADKSTSTAYMELSSLRSEDTAVYYCASPPYYDSSGYYPLGAFDIWGQGTMVTVSSAGGGGSGGGGSGGGGSGGGGSSYELTQPPSVSVSPGQTASITCSGDKLGEKYASWYQQKAGQSPILVIYQDSKRPSGIPERFSGSNSGNTATLTISGLQAGDEADYYCQAWDGSSTYVFGTGTKVTVLG (SEQ ID NO: 34) | | |

Chin, S M. et al. (2018). Structure of the 4-1BB/4-1BBL complex and distinct binding and functional properties of utomilumnab and urelunmab. Nature Communications 9:4679. DOI: 10.1038/s41467-018-07136-7

As used in this specification and the appended claims, the singular forms "a", "an" and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure.

Ranges: throughout this disclosure, various aspects of the invention can be presented in a range format. It should be understood that the description in range format is merely for

REFERENCES

Kwon, B. S., & Weissman, S. M. (1989). DNA sequences of two inducible T-cell genes. Proc Natl Acad Sci USA, 86(6), 1963-1967.

Zhang, Y., Huo, M., Zhou, J., & Xie, S. (2010). PKSolver: An add-in program for pharmacokinetic and pharmacodynamic data analysis in Microsoft Excel. *Comput Methods Programs Biomed,* 99(3), 306-314. doi: 10.1016/j.cmpb.2010.01.007 convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.1, 2.2, 2.7, 3, 4, 5, 5.5, 5.75, 5.8, 5.85, 5.9, 5.95, 5.99, and 6. This applies regardless of the breadth of the range.

Although the invention has been described with reference to the above examples, it will be understood that modifications and variations are encompassed within the spirit and scope of the invention. Accordingly, the invention is limited only by the following claims.

What is claimed is:

1. An antibody or an antigen binding fragment thereof comprising:
   (i) a $V_H$ region comprising complementarity-determining region (CDR)-H1, CDR-H2, and CDR-H3, wherein CDR-H1 is the amino acid sequence of SEQ ID NO: 19, CDR-H2 is the amino acid sequence of SEQ ID NO:20, and CDR-H3 is the amino acid sequence of SEQ ID NO:21 and/or a VH region having the amino acid sequence of SEQ ID NO: 17; and
   (ii) a $V_L$ region comprising CDR-L1, CDR-L2, and CDR-L3, wherein CDR-L1 is the amino acid sequence of SEQ ID NO:22, CDR-L2 is the amino acid sequence of SEQ ID NO:23, and CDR-L3 is the amino acid sequence of SEQ ID NO:24 and/or a VL region having the amino acid sequence of SEQ ID NO: 18, wherein the antibody or antigen binding fragment binds to CD137.

2. The antibody or antigen binding fragment of claim 1, wherein the antibody comprises an Fc domain.

3. The antibody or antigen binding fragment of claim 2, wherein the Fc domain is an IgG domain, an IgE domain, an IgM domain, and IgD domain, an IgA domain, or an IgY domain.

4. The antibody or antigen binding fragment of claim 3, wherein the IgG domain is an IgG1 domain, an IgG2 domain, an IgG3 domain, or an IgG4 domain.

5. The antibody or antigen binding fragment of claim 4, wherein the IgG1 domain comprises an amino acid sequence of SEQ ID NO:26.

6. The antibody or antigen binding fragment of claim 4, wherein the IgG4 domain comprises an amino acid sequence of SEQ ID NO:25.

7. The antibody or antigen binding fragment of claim 1, wherein the antigen binding fragment comprises an scFv, an F(ab)2, or an Fab.

8. The antibody or antigen binding fragment of claim 7, wherein the scFV comprises the amino acid sequence of SEQ ID NO:34.

9. A pharmaceutical composition comprising the antibody or antigen binding fragment of claim 1 and a pharmaceutically acceptable carrier.

10. The pharmaceutical composition of claim 9, wherein the pharmaceutically acceptable carrier is conjugated to a C-terminus of one or more polypeptides of the antibody or antigen binding fragment.

11. An antibody-drug conjugate comprising the antibody or antigen binding fragment of claim 1 and a further therapeutic agent.

12. The antibody-drug conjugate of claim 11, wherein the further therapeutic agent is covalently linked to the antibody or antigen binding fragment via a linker.

* * * * *